US012473541B2

(12) United States Patent
Svendsen et al.

(10) Patent No.: US 12,473,541 B2
(45) Date of Patent: *Nov. 18, 2025

(54) VARIANTS AND COMPOSITIONS COMPRISING VARIANTS WITH HIGH STABILITY IN PRESENCE OF A CHELATING AGENT

(71) Applicant: Novozymes A/S, Bagsvaerd (DK)

(72) Inventors: Allan Svendsen, Hoersholm (DK); Annette Helle Johansen, Bagsvaerd (DK); Mads Bjoernvad, Virum (DK); Frank W. Rasmussen, Roskilde (DK); Michael Skjoet, Roskilde (DK); Signe Eskildsen Larsen, Lyngby (DK); Jens Oebro, Copenhagen (DK); Svend Kaasgaard, Skovlunde (DK); Lars Beier, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/337,257

(22) Filed: Jun. 19, 2023

(65) Prior Publication Data

US 2023/0365953 A1 Nov. 16, 2023

Related U.S. Application Data

(63) Continuation of application No. 17/821,297, filed on Aug. 22, 2022, now Pat. No. 11,959,107, and a continuation of application No. 17/204,244, filed on Mar. 17, 2021, now Pat. No. 11,453,868, which is a continuation of application No. 16/834,010, filed on Mar. 30, 2020, now abandoned, which is a continuation of application No. 16/362,955, filed on Mar. 25, 2019, now Pat. No. 10,655,116, which is a continuation of application No. 15/708,669, filed on Sep. 19, 2017, now Pat. No. 10,240,135, which is a continuation of application No. 13/024,770, filed on Feb. 10, 2011, now Pat. No. 9,896,673.

(60) Provisional application No. 61/303,345, filed on Feb. 11, 2010.

(30) Foreign Application Priority Data

Feb. 10, 2010 (EP) .................................... 10153180

(51) Int. Cl.
*C12N 9/28* (2006.01)

(52) U.S. Cl.
CPC ................................ *C12N 9/2417* (2013.01)

(58) Field of Classification Search
None
See application file for complete search history.

(56) References Cited

U.S. PATENT DOCUMENTS

| | | | |
|---|---|---|---|
| 6,093,562 A | 7/2000 | Bisgård-Frantzen et al. | |
| 6,197,565 B1 | 3/2001 | Svendsen et al. | |
| 6,204,232 B1 | 3/2001 | Borchert et al. | |
| 6,361,989 B1 | 3/2002 | Svendsen et al. | |
| 6,410,295 B1 | 6/2002 | Andersen et al. | |
| 6,528,298 B1 | 3/2003 | Svendsen et al. | |
| 8,343,907 B2 | 1/2013 | Bianchetti et al. | |
| 9,896,673 B2 | 2/2018 | Svendsen et al. | |
| 10,017,752 B2 | 7/2018 | Andersen et al. | |
| 10,030,239 B2 | 7/2018 | Gjermansen | |
| 10,240,135 B2 | 3/2019 | Svendsen et al. | |
| 10,655,116 B2 | 5/2020 | Svendsen et al. | |
| 11,453,868 B2 | 9/2022 | Svendsen et al. | |
| 11,959,107 B2 * | 4/2024 | Svendsen | C12N 9/2417 |
| 2008/0193999 A1 | 8/2008 | Andersen et al. | |
| 2013/0059315 A1 | 3/2013 | Svendsen et al. | |
| 2020/0270593 A1 | 8/2020 | Svendsen et al. | |
| 2021/0317431 A1 | 10/2021 | Svendsen et al. | |
| 2023/0002748 A1 | 1/2023 | Svendsen et al. | |
| 2023/0365953 A1 * | 11/2023 | Svendsen | C12N 9/2417 |

FOREIGN PATENT DOCUMENTS

| | | | |
|---|---|---|---|
| CN | 1278298 | A | 12/2000 |
| CN | 1367824 | A | 9/2002 |
| CN | 1529752 | C1 | 9/2004 |
| CN | 1550549 | A | 12/2004 |
| CN | 1624124 | A | 6/2005 |
| CN | 101010429 | A | 8/2007 |
| EP | 2534233 | A2 | 8/2011 |
| JP | 11503003 | A | 3/1999 |
| JP | 2001520006 | A | 10/2001 |
| JP | 2001521739 | A | 11/2001 |
| JP | 2002540784 | A | 12/2002 |
| JP | 2002540785 | A | 12/2002 |
| JP | 2002540786 | A | 12/2002 |
| JP | 2008504811 | A | 2/2008 |
| JP | 2012552988 | B2 | 5/2013 |
| JP | 2013519757 | A | 5/2013 |
| JP | 2015199964 | A | 11/2015 |
| WO | 1995026397 | A1 | 10/1995 |
| WO | 1996023873 | A1 | 8/1996 |
| WO | 1999019467 | A1 | 4/1999 |
| WO | 1999023211 | A1 | 5/1999 |
| WO | 2000060058 | A2 | 10/2000 |
| WO | 2000060060 | A2 | 10/2000 |
| WO | 2001088107 | A2 | 11/2001 |
| WO | 2002010355 | A2 | 2/2002 |
| WO | 2002092797 | A2 | 11/2002 |
| WO | 2006002643 | A2 | 1/2006 |
| WO | 2009061379 | A2 | 5/2009 |
| WO | 2011100410 | A2 | 8/2011 |

OTHER PUBLICATIONS

Anonymous, IP.com, 2005, PCTDK2005000469, pp. 1-63.

(Continued)

*Primary Examiner* — Hope A Robinson
(74) *Attorney, Agent, or Firm* — Yoshimi D. Barron

(57) ABSTRACT

The present invention relates to variants of an alpha-amylase having improved stability to chelating agents relative to its parent enzyme, compositions comprising the variants, nucleic acids encoding the variants, methods of producing the variants, and methods for using the variants.

16 Claims, No Drawings

Specification includes a Sequence Listing.

(56) References Cited

OTHER PUBLICATIONS

Declerck et al., 2000, J. Mol. Biol., vol. 301, pp. 1041-1057.
Tsukamoto et al., 1988, Biochem and Biophys Res Comm, vol. 151, No. 1, pp. 25-31.
WO2002010355A2—EBI Access No. ABB76644.

* cited by examiner

VARIANTS AND COMPOSITIONS COMPRISING VARIANTS WITH HIGH STABILITY IN PRESENCE OF A CHELATING AGENT

CROSS-REFERENCE TO RELATED APPLICATIONS

This application is a continuation of U.S. application Ser. No. 17/821,297 filed Aug. 22, 2022, now U.S. Pat. No. 11,959,107, which is a continuation of U.S. application Ser. No. 17/204,244 filed Mar. 17, 2021, now U.S. Pat. No. 11,453,868, which is a continuation of U.S. application Ser. No. 16/834,010 filed Mar. 30, 2020, now abandoned, which is a continuation of U.S. application Ser. No. 16/362,955 filed Mar. 25, 2019, now U.S. Pat. No. 10,655,116, which is a continuation of U.S. application Ser. No. 15/708,669 filed Sep. 19, 2017, now U.S. Pat. No. 10,240,135, which is a continuation of U.S. application Ser. No. 13/024,770 filed Feb. 10, 2011, now U.S. Pat. No. 9,896,673, which claims priority or the benefit under 35 U.S.C. 119 of European application no. 10153180.4 filed Feb. 10, 2010 and U.S. provisional application No. 61/303,345 filed Feb. 11, 2010. The disclosure of each application is fully incorporated herein by reference.

REFERENCE TO A SEQUENCE LISTING

This application contains a Sequence Listing in computer readable form, which is incorporated herein by reference. The Sequence Listing was created on Jun. 19, 2023, is named SQ.xml, and has 50,620 bytes.

FIELD OF THE INVENTION

The present invention relates to variants of an alpha-amylase having improved stability to chelating agents relative to its parent enzyme, compositions comprising the variants, nucleic acids encoding the variants, methods of producing the variants, and methods for using the variants.

BACKGROUND OF THE INVENTION

Alpha-amylases (alpha-1,4-glucan-4-glucanohydrolases, E.C. 3.2.1.1) constitute a group of enzymes, which catalyses hydrolysis of starch and other linear and branched 1,4-gluosidic oligo- and polysaccharides.

There is a long history of industrial application of alpha-amylases in, e.g., detergent, baking, brewing, starch liquefaction and saccharification such as in preparation of high fructose syrups or as part of ethanol production from starch. Many of these and other applications of alpha-amylases utilize alpha-amylases derived from microorganisms, in particular bacterial alpha-amylases.

Among the first bacterial alpha-amylases to be used were an alpha-amylase from *B. licheniformis*, also known as Termamyl, which has been extensively characterized and the crystal structure has been determined for this enzyme. Alkaline amylases, such as the alpha-amylase derived from *Bacillus* sp. as disclosed in WO 95/26397, form a particular group of alpha-amylases that have found use in detergents. Many of these known bacterial amylases have been modified in order to improve their functionality in a particular application.

Termamyl and many highly efficient alpha-amylases required calcium for activity. The crystal structure for Termamyl was found that four calcium atoms were bound in the alpha-amylase structure coordinated by negatively charged amino acid residues. In other alpha-amylases, the amount of calcium ions bound in the structure might be different. This requirement for calcium is a disadvantage in applications where strong chelating compounds are present, such as in detergents or during ethanol production from whole grains.

As mentioned above it is well known that a number of enzymes are dependent on calcium or other metal ions such as magnesium or zinc for both activity and stability, hence it is a challenge to develop enzymes which are both stable and show good performance in compositions comprising a chelating agent, e.g., detergents containing chelating agents or compositions for use in the production of biofuel wherein the plant material or the starch-containing material has a natural content of chelating agents such as, e.g., phytic acid. Chelating agents are, e.g., added or incorporated to reduce the water hardness during wash, protect bleaching agents that may also be present, and chelating agents also have a direct effect on the removal of some stains. The stability of a calcium dependent enzyme in a detergent can sometimes be improved by addition of calcium to the detergent, but often this will then destroy the stain removing effect. Furthermore, addition of calcium to a liquid detergent may present problems with the formulation, i.e., the physical stability of the detergent.

SUMMARY OF THE INVENTION

It would therefore be beneficial to provide compositions and variants of alpha-amylases which are stable towards chelating agents and which preferably have retained or increased wash performance compared to the parent alpha-amylase.

Thus, a first aspect of the invention relates to a composition comprising a variant of a parent alpha-amylase, wherein the variant comprises a substitution at one or more positions selected from the group consisting of 195, 193, 197, 198, 200, 203, 206, 210, 212, 213 and 243, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0.

Another aspect relates to a composition comprising a variant of a parent alpha-amylase, wherein the variant comprises a substitution at one or more positions selected from the group comprising 195, 193, 197, 198, 200, 203, 206, 210, 212, 213 and 243, using the numbering according to SEQ ID NO:6, and further comprising at least one chelating agent wherein said chelating agent is capable of reducing the free calcium ion concentration from 2.0 mM to 0.10 mM at a chelating agent concentration less than 0.9 times the concentration of citrate capable of reducing the free calcium ion concentration from 2.0 mM to 0.10 mM, when measured at 21° C. and pH 8.0.

The invention further relates to a method for preparing a polypeptide comprising:

(a) providing an amino acid sequence of a parent polypeptide having amylase activity;
(b) selecting one or more amino acids occupying one or more positions corresponding to positions 195, 197, 198, 200, 203, 206, 210, 212, 213, 243 and further selecting one or more position corresponding to positions 116, 118, 129, 133, 142, 146, 147, 149, 151, 152, 169, 174, 186, 235, 244, 303, 320, 339, 359, 418, 431, 434, 447, 458 of the mature polypeptide of SEQ ID NO:6;

(c) modifying the sequence by substituting or deleting the selected amino acid residue or inserting one or more amino acid residues adjacent to the selected amino acid residue;

(d) producing a variant polypeptide having the modified sequence;

(e) testing the variant polypeptide for amylase activity and stability; and (f) selecting a variant polypeptide having amylase activity and increased stability relative to the parent polypeptide in the presence of a chelating agent wherein said chelating agent at a concentration below 10 mM is capable of reducing the concentration of free calcium ions from 2.0 mM to 0.10 mM at 21° C. and pH 8.0.

In a preferred aspect the invention relates to a variant of a parent alpha-amylase comprising an alteration at one or more positions corresponding to positions selected from the group consisting of 195, 197, 198, 200, 203, 206, 210, 212, 213 and 243 and further comprising an alteration at one or more positions corresponding to positions selected from the group consisting of 116, 118, 129, 133, 142, 146, 147, 149, 151, 152, 169, 174, 186, 235, 244, 303, 320, 339, 359, 418, 431, 434, 447 and 458 wherein (a) the alteration(s) are independently (i) an insertion of an amino acid immediately downstream and adjacent of the position, (ii) a deletion of the amino acid which occupies the position, and/or (iii) a substitution of the amino acid which occupies the position, (b) the variant has alpha-amylase activity; and (c) each position corresponds to a position of the amino acid sequence of the enzyme having the amino acid sequence of SEQ ID NO: 6.

In another aspect the invention relates to a variant of a parent alpha-amylase comprising at least one, at least two, or at least three deletions in amino acid region of 181, 182, 183, or 184 and further comprising an alteration at one or more positions selected from the group consisting of 195, 197, 198, 200, 203, 206, 210, 212, 213 and 243 and further comprising an alteration at one or more positions selected from the group consisting of 116, 118, 129, 133, 142, 146, 147, 149, 151, 152, 169, 174, 186, 235, 244, 303, 320, 339, 359, 418, 431, 434, 447 and 458 wherein (a) the alteration(s) are independently (i) an insertion of an amino acid immediately downstream and adjacent of the position, (ii) a deletion of the amino acid which occupies the position, and/or (iii) a substitution of the amino acid which occupies the position, (b) the variant has alpha-amylase activity; and (c) each position corresponds to a position of the amino acid sequence of the enzyme having the amino acid sequence of SEQ ID NO: 6.

The invention further relates to an isolated nucleotide sequence encoding the variant of the invention and recombinant host cell comprising the nucleotide sequence encoding the variants according to the invention.

DETAILED DESCRIPTION OF THE INVENTION

Definitions

Alpha-Amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides. Alpha-amylases are known derived from a wide selection of organisms including Bacteria, such as from species of the genus *Bacillus* e.g. *Bacillus licheniformis*; from species of fungi, such as *Aspergillus oryzae* (TAKA-amylase) or *Aspergillus niger*; from plants such as barley and from mammals.

Wild-Type Enzyme: The term “wild-type” alpha-amylase denotes an alpha-amylase expressed by a naturally occurring microorganism, such as a bacterium, yeast or filamentous fungus found in nature. The terms “wild-type enzyme” and “parent enzyme” can be used interchangeably when the parent enzyme is not a variant enzyme.

Variant Enzyme: The term “variant” is defined herein as a polypeptide having alpha-amylase activity comprising an alteration, such as a substitution, insertion, and/or deletion, of one or more (or one or several) amino acid residues at one or more (or one or several) specific positions of the parent or wild type alpha-amylase. Preferably less than 50 modifications, more preferred less than 30 modifications. The altered alpha-amylase is obtained through human intervention by modification of the parent alpha-amylase.

Parent Enzyme: The term “parent” alpha-amylase as used herein means an alpha-amylase to which modifications are made to produce the variant alpha-amylases of the present invention. This term also refers to the polypeptide with which a variant of the invention is compared. The parent may be a naturally occurring (wild type) polypeptide, or it may even be a variant thereof, prepared by any suitable means. For instance, the parent protein may be a variant of a naturally occurring polypeptide which has been modified or altered in the amino acid sequence. Thus, the parent alpha-amylase may have one or more (or one or several) amino acid substitutions, deletions and/or insertions. Thus the parent alpha-amylase may be a variant of a parent alpha-amylase. A parent may also be an allelic variant which is a polypeptide encoded by any of two or more alternative forms of a gene occupying the same chromosomal locus.

Improved property: The term “improved property” is defined herein as a characteristic associated with a variant that is improved compared to the parent alpha-amylase. Such improved properties include, but are not limited to, increased amylolytic activity, e.g., when measured in EnzChek assay or the PNP-G7 assay as described in Examples section herein, increased wash performance such as soil performance, e.g., performance to starch containing soils, stain removal, anti-greying, stability, e.g., thermostability, pH stability, or stability in the presence of builders, incl. chelants, stability in powder, liquid or gel detergent formulations or dishwashing compositions, altered temperature-dependent performance and activity profile, pH activity, substrate specificity, product specificity, and chemical stability. Wash performance and/or dish wash performance may be measured as described below under “Materials and Methods” in the present application. Preferably the variants of the invention include a combination of improved properties such as improved stability, improved wash performance, improved dish wash performance and/or improved activity in detergent. Improved stability includes both stability during storage in a concentrated detergent product and stability in the diluted detergent during wash. The improved property includes improved wash or dish wash performance at low temperature.

Activity: In the present context the term “activity” is the amylolytic activity measured by the number of 1,4-alpha-D-glycosidic linkages hydrolysed in polysaccharides containing three or more 1,4-alpha-linked D-glucose units as, e.g., in starch per unit of time and per unit of enzyme protein at specified conditions, e.g., the activity obtained at specified conditions per mL of an enzyme sample of g of an enzyme protein. The activity can be measured in, e.g., EnzChek assay or a PNP-G7 assay as described below under "Material and Methods". In the present application the term "activity" is used interchangeably with "amylolytic activity". The term "specific activity" is often used to describe the maximal activity obtained per mL (or g) of an enzyme protein.

Improved chemical stability: The term "improved chemical stability" is defined herein as a variant enzyme displaying retention of enzymatic activity after a period of incubation in the presence of a chemical or chemicals, either naturally occurring or synthetic, which reduces the enzymatic activity of the parent enzyme. Improved chemical stability may also result in variants better able to catalyze a reaction in the presence of such chemicals. In a particular aspect of the invention the improved chemical stability is an improved stability in a detergent, in particular in a liquid detergent. The improved detergent stability is in particular an improved stability of the alpha-amylase activity when an alpha-amylase variant of the present invention is mixed into a liquid detergent formulation comprising a chelating agent, the liquid also includes gels or a paste. The liquid detergent formulation may refer to concentrated detergent which is added during a laundry or automated dish wash process or a dilute detergent such as a wash solution, i.e., an aqueous solution to which the concentrated detergent is added.

In the present invention liquid detergents are particular useful as liquid laundry detergents.

Stability: The term "stability" includes storage stability and stability during use, e.g., during a wash process or another industrial process, and reflects the stability of the amylase as a function of time, e.g., how much activity is retained when the amylase is kept in solution in particular in a detergent solution. For example, the alpha-amylase variant may have a residual activity, i.e., how much activity is retained, above 70% after 18 hours at 31° C. The stability is influenced by many factors, e.g., pH, temperature, detergent composition, e.g., amount and type of builder, surfactants etc. The amylase stability is measured using either the EnzCheck assay or the PNP-G7 assay described in under "Materials and Methods".

Improved stability: The term "improved stability" is defined herein as a variant enzyme displaying an increased stability which is higher than the stability of the parent alpha-amylase, e.g., by having a residual activity above 70% or having at least 10 pp improvement in residual activity relative to parent after 18 hours at pH 8 in the presence of 1.5% (w/v) DTPA at 31° C. when measured in the EnzCheck assay as described under "Materials and Methods". The percentage point (pp) improvement in residual activity of the variant relative to the parent is calculated as the difference between the residual activity of the variant and that of the parent as described under "Materials and Methods".

Builder: Builders may be classified by the test described by Nagarajan et al., 1984 JAOCS 61(9): 1475-1478 to determine the minimum builder level required to lower the water hardness at pH 8 from 2.0 mM (as $CaCO_3$) to 0.10 mM in a solution. The builder may particularly be chelating agent that forms water-soluble complexes with, e.g., calcium and magnesium ions.

Chelating agents or chelators are chemicals which form molecules with certain metal ions, inactivating the ions so that they cannot react with other elements thus a binding agent that suppresses chemical activity by forming chelates. Chelation is the formation or presence of two or more separate bindings between a ligand and a single central atom. The ligand may be any organic compound, a silicate or a phosphate. In the present context the term "chelating agents" comprises chelants, chelating agent, chelating agents, complexing agents, or sequestering agents that forms water-soluble complexes with metal ions such as calcium and magnesium. The chelate effect describes the enhanced affinity of chelating ligands for a metal ion compared to the affinity of a collection of similar nonchelating ligands for the same metal. Chelating agents having binding capacity with metal ions, in particular calcium ($Ca^{2+}$) ions, and has been used widely in detergents and compositions in general for wash, such as laundry or dish wash. Chelating agents have however shown themselves to inhibit enzymatic activity. The term chelating agent is used in the present application interchangeably with "complexing agent" or "chelating agent" or "chelant".

Since most alpha-amylases are calcium sensitive the presence of chelating agents these may impair the enzyme activity. The calcium sensitivity of alpha-amylases can be determined by incubating a given alpha-amylase in the presence of a strong chelating agent and analyze the impact of this incubation on the activity of the alpha-amylase in question. A calcium sensitive alpha-amylase will lose a major part or all of its activity during the incubation.

Characterizing chelating agents: As mentioned the chelate effect or the chelating effect describes the enhanced affinity of chelating ligands for a metal ion compared to the affinity of a collection of similar nonchelating ligands for the same metal. However, the strength of this chelate effect can be determined by various types of assays or measure methods thereby differentiating or ranking the chelating agents according to their chelating effect (or strength).

In a preferred assay the chelating agents may be characterized by their ability to reduce the concentration of free calcium ions ($Ca^{2+}$) from 2.0 mM to 0.10 mM or less at pH 8.0, e.g., by using a test based on the method described by M. K. Nagarajan et al., JAOCS, Vol. 61, no. 9 (September 1984), pp. 1475-1478. An example of characterization of chelating agents using the Nagarajan et. al. based method is described in example 2a. Preferably, a the chelating agent according to the invention encompass chelating agents able to reduce the concentration of free calcium ions from 2.0 mM to 0.1 mM or less at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM, when measured in pH 8.0 at 21° C.

Preferably, the chelating agent according to the invention encompasses chelating agents able to reduce the concentration of free calcium ions from 2.0 mM to 0.1 mM at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM, when measured in 80 mM potassium chloride and 49 mM EPPS ((4-(2-hydroxyethyl)

piperazine-1-propanesulfonic acid)), at pH 8 at 21° C. In a particular preferred embodiment, the chelating agent is able to reduce the concentration of free calcium ions from 2.0 mM to 0.1 mM when measured in 80 mM potassium chloride and 49 mM EPPS, at pH 8 and 21° C. and using a calcium ion selective electrode for the determination of the free calcium concentration, as described under "Materials and Methods". Thus, preferably, the chelating agents encompass chelating agents which are able to reduce the concentration of free calcium ions from 2.0 mM to 0.10 mM at a concentration below 10 mM, preferably below 9.5 mM, preferably below 9.0 mM, preferably below 8.5 mM, preferably below 8.0 mM, preferably below 7.5 mM, preferably below 7.0 mM, preferably below 6.5 mM, preferably below 6.0 mM, preferably below 5.5 mM, preferably, preferably below 5.0 mM, preferably below 4.5 mM, below 4.0 mM, preferably below 3.5 mM, preferably below 3.0 mM, preferably below 2.5 mM, preferably below 2.0 mM, preferably below 1.5 mM or preferably below 1.0 mM when tested at pH 8.0 and 21° C., as described under "Materials and Methods".

In a particularly preferred embodiment the chelating agents is able to reduce the concentration of free calcium ions from 2.0 mM to 0.10 mM when measured in 80 mM potassium chloride and 49 mM EPPS at pH 8 and 21° C. at a concentration of 9 mM to 0.5 mM, preferably 9 mM to 1 mM, preferably 8 mM to 1 mM, preferably 7 mM to 1 mM, preferably 6 mM to 1 mM, preferably 5 mM to 1 mM, preferably 4 mM to 1 mM, preferably 3 mM to 1 mM, preferably 2 mM to 1 mM, preferably 9.0 mM to 1.5 mM, preferably 8.0 mM to 1.5 mM, preferably 7.0 mM to 1.5 mM, preferably 6.0 mM to 1.5 mM, preferably 5.0 mM to 1.5 mM, preferably 4.0 mM to 1.5 mM, preferably 3.0 to 1.5 mM, preferably 2.5 mM to 1.0 mM, preferably 2.0 mM to 1.1 mM, preferably 1.85 mM to 1.0 mM.

The reduction in free calcium ion concentration from 2.0 mM $Ca^{2+}$ to 0.10 mM, corresponds to reducing the water hardness from 200 ppm (as $CaCO_3$, in the form of $Ca(HCO_3)_2$ in the presence of acidic $CO_2$) to 10 ppm. The minimum builder level is calculated from the sodium salt of the chelant and on a 100% dry chelant basis.

The chelating effect of the chelating agent can also be measured relative to citrate. The concentration of the citrate able to reduce the amount of free calcium ion concentration from 2.0 mM to 0.10 mM is assigned the value of 1 and the results of the chelating agents are compared to this value. The preferred chelating agent according to the invention is capable of reducing the free calcium concentration from 2.0 mM to 0.10 mM at a concentration below 0.9, such as below 0.8, such as below 0.7, such as below 0.6, such as below 0.5, such as below 0.4, such as below 0.3, such as below 0.2, such as below 0.1 times lower compared to the concentration of citrate, when measured at pH 8.0 and 21° C. The preferred chelating agent according to the invention is capable of reducing the free calcium concentration from 2.0 mM to 0.10 mM at a concentration below 0.9, such as below 0.8, such as below 0.7, such as below 0.6, such as below 0.5, such as below 0.4, such as below 0.3, such as below 0.2, such as below 0.1 times lower compared to the concentration of citrate, when measured in pH 8.0 at 21° C. using a calcium ion selective electrode for the determination of the free calcium concentration when measured in 80 mM potassium chloride and 49 mM EPPS at 21° C. and pH 8.0.

In a particularly preferred embodiment the chelating agent is able to reduce the concentration of free calcium ions from 2.0 mM to 0.10 mM at a chelating agent concentration below 1.0 to 0.1, such as below 0.9 to 0.1, such as below 0.8 to 0.1, such as below 0.7 to 0.1, such as below 0.6 to 0.1, such as below 0.5 to 0.1, such as below 0.4 to 0.1, such as below 0.35 to 0.1, such as below 0.3 to 0.1 times lower compared to the concentration of citrate able to reduce the concentration of free calcium ions from 2.0 mM to 0.10 mM, when measured at pH 8.0 and 21° C.

Thus, a preferred embodiment of the invention concerns a composition comprising a variant of a parent alpha-amylase wherein the variant comprise a substitution at one or more positions in the range 193 to 213, using the numbering according to SEQ ID NO: 6, and further comprising at least one chelating agent wherein said chelating agent is capable of reducing the free calcium ion concentration from 2.0 mM to 0.10 mM at a chelating agent concentration less than 0.9 times the concentration of citrate capable of reducing the free calcium ion concentration from 2.0 mM to 0.10 mM, when measured at 21° C. and pH 8.

A further embodiment of the invention relates to a composition comprising a variant of a parent alpha-amylase wherein the variant alpha-amylase comprises a substitution at one or more positions selected from the group consisting of 193, 195, 197, 198, 200, 203, 206, 210, 212 and 213, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0.

A further embodiment of the invention relates to a composition comprising a variant of a parent alpha-amylase wherein the variant alpha-amylase comprises a substitution at one or more positions selected from the group consisting of 193, 195, 197, 198, 200, 203, 206, 210, 212 and 213, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0, and optionally a cleaning adjunct.

A further embodiment of the invention relates to a composition comprising a variant of a parent alpha-amylase wherein the variant alpha-amylase comprises an amino acid sequence which is at least 70% identical to SEQ ID NO: 6 and further comprises a substitution at one or more positions selected from the group consisting of 193, 195, 197, 198, 200, 203, 206, 210, 212 and 213, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0.

Thus, the chelating agent according to the invention is able to reduce the free calcium ion concentration from 2.0 mM to 0.10 mM at a concentration lower than the concentration of citrate necessary to reduce the free calcium ion concentration from 2.0 mM to 0.10 mM at the same conditions.

Alternatively, the strength of the complex formed between the chelating agent and metal ions such as calcium and/or magnesium, is expressed as the log K value (equilibrium or binding or dissociating or stability constant). This constant may be measured at a given pH, at a given temperature and at a given ionic strength.

As mentioned above the strength of the complex formed between the chelating agent and the metal ions, e.g., calcium and/or magnesium may be expressed as the log K value (equilibrium or binding or dissociating or stability constant), the constant may be measured by isothermal titration calorimetry (ITC) as described in A. Nielsen et al., Anal. Biochem. Vol. 314, (2003), pp 227-234 and from the K value, the log K can be calculated as the logarithm of the K value (base 10). The log K value measured by this method will depend on the temperature, pH, ion strength, so it is important when comparing log K values, that they are determined at similar, preferably the same, conditions. Furthermore, by introducing a standard as reference, such as citrate, impacts from variations in the experiments can be reduced. Preferably log K is determined as described under "Materials and Methods" of the present application thus in one embodiment of the invention the chelating agent in the composition according to the invention has a log K of at least 3, such as at least 4, such as at least 5, such as at least 6, such as at least 7, such as at least 8, such as at least 9, such as at least 10, such as at least 11, when the log K is measured at pH 10 and 19° C. as described under "Materials and Methods". The log K value of the chelating agent in the compositions according to the invention may also be in the range 3-11, such as 3-10, such as 3-9, such as 3-8, such as 4-11, such as 5-11 such as 6-11, such as 4-10, such as 5-10, such as 4-9, such as 5-9, such as 4-8, in particularly 5-8. Preferably, the log K of the chelating agent in the composition according to the invention is a factor of at least 1, such as at least 1.33, such as at least 1.67, such as at least 2, such as at least 2.33, such as at least 2.67, such as at least 3, such as at least 3.33, such as at least 3.67 times the log K of citrate determined as described under "Materials and Methods". The chelating agent in the compositions according to the invention may also be in the range of a factor 1-3.67, such as 1-3.33, such as 1-3.00, such as 1-2.67, such as 1.33-3.67, such as 1.33-3.33, such as 1.33-3.00, such as 1.33-2.67, such as 1.67-3.67, such as 1.67-3.33, such as 1.67-3, in particular 1.67-2.67 times the log K of citrate determined as described under "Materials and Methods".

Useful chelating agents may be, but are not limited to, the following: N-(1,2-dicarboxy-ethyl)-D,L-aspartic acid (IDS), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA), sulfomethyl-N,N-diacetic acid (SMDA), N-(hydroxyethyl)-ethylidenediaminetriacetate (HEDTA), diethanolglycine (DEG), aminotris(methylenephosphonic acid) (ATMP).

The preferred chelating agent may contain an amino group and may be, e.g., an amino-polycarboxylate or a phosphonate. It may be a monomeric molecule comprising one, two or three amino groups (typically secondary or tertiary amino groups), and it may contain two, three, four or five carboxyl groups or even more carboxyl groups. The chelating agents may be phosphorus containing or without phosphor. There are many ways of grouping chelating agents one way might be as follows:

Chelating agents may be carboxylates or be based on carboxylate groups like EDTA (ethylene diamine tetraacetate), NTA (2,2',2"-nitrilotriacetate), citrate, 2-hydroxypropan-1,2,3-tricarboxylate, DTPA (diethylenetriaminepentaacetic acid), MGDA (methylglycinediacetic acid or N,N'-bis(carboxymethyl)alanine), EGTA (ethylene glycol tetraacetic acid), EDDS (ethylenediamine-N,N'-disuccinic acid), GLDA (L-Glutamic acid, N,N-diacetic acid), Polycarboxylates such as PAA [poly(acrylic acid)], PAA/PMA [copoly(acrylic acid/maleic acid)].

Chelating agents containing phosphorous may be polyphosphates or phosphonates, such as Sodium tripolyphosphate (STP), HEDP (1-Hydroxyethylidene-1,1-Diphosphonic Acid), EDTMP [bis(phosphonomethyl)amino] methylphosphonic acid] or (ethylenediamine tetra(methylene phosphonic acid)), EDTMPA (ethylenediaminetetramethylenetetraphosphonic acid), DTPMP (diethylenetriamine penta (methylene phosphonic acid), DTMPA (diethylenetriaminepenta(methylenehosphonic acid)). The chelating agents may contain nitrogen such as in EDTA, NTA, DTPA, PDTA, GLDA, MGDA, EDDS, EDTMP, EDTMPA, and DTPMP or ASMA, ASDA, ASMP, IDA, SMAS, SEAS, SMGL, SEGL, MIDA, α-ALDA, SEDA, ISDA, PHDA, ANDA, SLDA, TUDA, SMDA, HEDTA, DEG, ATMP, or mixtures thereof.

Thus, the preferred chelating agents may be but are not limited to the following: ethylene-diamine-tetra-acetic acid (EDTA), diethylene triamine penta methylene phosphonic acid (DTMPA, DTPMP), hydroxy-ethane diphosphonic acid (HEDP), ethylenediamine N,N'-disuccinic acid (EDDS), methyl glycine di-acetic acid (MGDA), diethylene triamine penta acetic acid (DTPA), propylene diamine tetraacetic acid (PDTA), 2-hydroxypyridine-N-oxide (HPNO), methyl glycine diacetic acid (MGDA), glutamic acid N,N-diacetic acid (N,N-dicarboxymethyl glutamic acid tetrasodium salt (GLDA) and nitrilotriacetic acid (NTA) or mixtures thereof. The chelating agents may be present in their acid form or a salt, preferably the chelating agents may be present as a sodium, ammonium or potassium salt.

Further chelating agents may be chelating agents which originate from plant material, such as, e.g., starch-containing material as described in detail below. Examples of such natural chelating agents are, but are not limited to, phytic acid (also known as Inositol hexaphosphoric acid (IP6), or phytin, or phytate when in salt for), Inositol diphosphoric acid, Inositol triphosphoric or Inositol pentaphosphoric acid.

Chelating agent may be present in the composition in an amount from 0.0001 wt % to 20 wt %, preferably from 0.01 to 10 wt %, more preferably from 0.1 to 5 wt %.

Parent alpha-amylase: The parent alpha-amylase may in principle be any alpha-amylase for which it is desired to prepare a variant having improved stability during storage or in use, e.g. during wash or in a starch hydrolyzing process. The improved stability may thus be observed as a reduced loss of amylolytic activity during storage or as an increased activity and performance during use. Known alpha-amylases are derived from a wide selection of organisms including Bacteria, such as from species of the genus *Bacillus* e.g. *Bacillus licheniformis*; from species of fungi, such as *Aspergillus oryzae* (TAKA-amylase) or *Aspergillus niger*; from plants such as barley and from mammals. The parent alpha-amylase may in principle be any such alpha-amylase irrespective of the origin.

It is well known that a number of alpha-amylases produced by *Bacillus* spp. are highly identical on the amino acid level. Because of the substantial identity found between these alpha-amylases, they are considered to belong to the same class of alpha-amylases, namely the class of "Termamyl-like alpha-amylases".

Accordingly, in the present context, the term "Termamyl-like" alpha-amylase" is intended to indicate an alpha-amylase, in particular *Bacillus* alpha-amylase, which, at the amino acid level, exhibits a substantial identity, i.e., at least 60% to the *B. licheniformis* alpha-amylase having the amino acid sequence shown in SEQ ID NO: 20 (Termamyl™), herein.

Termamyl-Like Alpha-Amylases

The identity of a number of known *Bacillus* alpha-amylases can be found in the below Table 1:

TABLE 1

| | SEQ | Percent identity | | | | | | | |
|---|---|---|---|---|---|---|---|---|---|
| | ID NO: | #707 | AP1378 | BAN | BSG | SP690 | SP722 | AA560 | Termamyl |
| #707 | 8 | 100.0 | 86.4 | 66.9 | 66.5 | 87.6 | 86.2 | 95.5 | 68.1 |
| AP1378 | 18 | 86.4 | 100.0 | 67.1 | 68.1 | 95.1 | 86.6 | 86.0 | 69.4 |
| BAN | 14 | 66.9 | 67.1 | 100.0 | 65.6 | 67.1 | 68.8 | 66.9 | 80.7 |
| BSG | 16 | 66.5 | 68.1 | 65.6 | 100.0 | 67.9 | 67.1 | 66.3 | 65.4 |
| SP690 | 12 | 87.6 | 95.1 | 67.1 | 67.9 | 100.0 | 87.2 | 87.0 | 69.2 |
| SP722 | 6 | 86.2 | 86.6 | 68.8 | 67.1 | 87.2 | 100.0 | 86.8 | 70.8 |
| AA560 | 10 | 95.5 | 86.0 | 66.9 | 66.3 | 87.0 | 86.8 | 100.0 | 68.3 |
| Termamyl | 20 | 68.1 | 69.4 | 80.7 | 65.4 | 69.2 | 70.8 | 68.3 | 100.0 |

For instance, the *B. licheniformis* alpha-amylase comprising the amino acid sequence shown in SEQ ID NO: 20 (commercially available as Termamyl™) has been found to be about 81% homologous with the *B. amyloliquefaciens* alpha-amylase comprising the amino acid sequence shown in SEQ ID NO: 14 (BAN) and about 65% homologous with the *B. stearothermophilus* alpha-amylase comprising the amino acid sequence shown in SEQ ID NO: 16 (BSG). Further homologous alpha-amylases include SP722 and SP690 disclosed in WO 95/26397 and further depicted in SEQ ID NO: 6 and SEQ ID NO: 12, respectively, herein. Other amylases are the AA560 alpha-amylase derived from *Bacillus* sp. and shown in SEQ ID NO: 10, and the SP707 or #707 alpha-amylase derived from *Bacillus* sp., shown in SEQ ID NO: 8 and described by Tsukamoto et al., 1988, Biochemical and Biophysical Research Communications 151: 25-31. Further homolog alpha-amylase is the KSM AP1378 alpha-amylase is disclosed in WO 97/00324 (from KAO Corporation) SEQ ID NO: 18. Yet another homolog alpha-amylase is the SP.7-7 alpha-amylase with SEQ ID NO: 22. Another suitable parent amylase is the K 38 SEQ ID NO: 2 or the *B. circulans* amylase with SEQ ID NO: 4 and SEQ ID NO: 24, described in WO 2005/001064.

Still further interesting alpha-amylases include the alpha-amylase produced by the *B. licheniformis* strain described in EP 0252666 (ATCC 27811), and the alpha-amylases identified in WO 91/00353 and WO 94/18314. Other commercial Termamyl-like alpha-amylases are comprised in the products sold under the following tradenames: OPTITHERM™ and TAKATHERM™ (Solvay); MAXAMYL™ (available from Gist-brocades/Genencor), SPEZYM® AA and SPEZYME® DELTA AA (available from Genencor), and KEISTASE™ (available from Daiwa), Dex Io, GC 521 (available from Genencor) and Ultraphlow (from Enzyme Biosystems), PURASTAR™ ST 5000E, PURASTAR™ HPAM L, POWERASE®, Spezyme FRED, GC358, CLEARFLOWO AA (from Danisco), or the alpha-amylase TS-23 (SEQ ID NO: 26 (Lin et al, J. App. Microbiol. 1997, 82, 325-334).

The non-Termamyl-like alpha-amylase may, e.g., be a fungal alpha-amylase, a mammalian or a plant alpha-amylase or a bacterial alpha-amylase (different from a Termamyl-like alpha-amylase). Specific examples of such alpha-amylases include the *Aspergillus oryzae* TAKA alpha-amylase, the *A. niger* acid alpha-amylase, the *Bacillus subtilis* alpha-amylase, the porcine pancreatic alpha-amylase and a barley alpha-amylase. All of these alpha-amylases have elucidated structures, which are markedly different from the structure of a typical Termamyl-like alpha-amylase as referred to herein.

The fungal alpha-amylases mentioned above, i.e., derived from *A. niger* and *A. oryzae*, are highly identical on the amino acid level and generally considered to belong to the same family of alpha-amylases. The fungal alpha-amylase derived from *Aspergillus oryzae* is commercially available under the trade name Fungamyl™.

Parent Hybrid Alpha-Amylases

The parent alpha-amylase may be a hybrid alpha-amylase, i.e., an alpha-amylase, which comprises a combination of partial amino acid sequences derived from at least two alpha-amylases.

The parent hybrid alpha-amylase may be one, which on the basis of amino acid homology and/or immunological cross-reactivity and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase from which a partial amino acid sequence derives may be any of those Termamyl-like, alpha-amylases referred to herein.

In one embodiment the parent Termamyl-like alpha-amylase is a hybrid Termamyl-like alpha-amylase identical to the *Bacillus licheniformis* alpha-amylase shown in SEQ ID NO: 20, except that the N-terminal 35 amino acid residues (of the mature protein) is replaced with the N-terminal 33 amino acid residues of the mature protein of the *Bacillus amyloliquefaciens* alpha-amylase shown in SEQ ID NO: 14 said hybrid may further have the following mutations: H156Y+A181T+N190F+A209V+Q264S (using the numbering in SEQ ID NO: 6) referred to as LE174. In another embodiment LE174 further comprising the mutations G48A, T491, G107A, 1201F, referred to as LE399. In one embodiment the parent is SEQ ID NO: 16 with the mutations 1181*+G182*+N195F.

In a preferred aspect of the invention the parent alpha-amylase is an alpha-amylase, which has the amino acid sequence shown in SEQ ID NO: 2, 4, 6, 8, 10, 12, 14, 16, 18, 20, 22, 24 or 26 herein. In another preferred aspect the parent alpha-amylase is an alpha-amylase, which displays 60%, preferred at least 65%, preferred at least 70%, preferred at least 75% preferred at least 80%, preferred at least 81%, preferred at least 82%, preferred at least 83%, preferred at least 84% preferred at least 85%, preferred at least 86%, preferred at least 87%, preferred at least 88%, preferred at least 89%, especially preferred at least 90%, especially preferred at least 91%, especially preferred at least 92%, especially preferred at least 93%, especially preferred at least 94%, even especially more preferred at least 95% homology, more preferred at least 96%, more preferred at least 97%, more preferred at least 98%, more preferred at least 99% of the mature polypeptide of SEQ ID NO: 2, 4, 6, 8, 10, 12, 14, 16, 18, 20, 22, 24 or 26.

In one aspect, the parent alpha-amylases have an amino acid sequence that differs (e.g., deletion, insertion or substitution) by one or several amino acids, preferably ten amino acids, more preferably by nine, eight, seven, six, five amino acids, more preferably by four amino acids, even more preferably by three amino acids, most preferably by two amino acids, and even most preferably by one amino acid from the mature polypeptide of SEQ ID NO: 2, 4, 6, 8, 10, 12, 14, 16, 18, 20, 22, 24 or 26.

The parent alpha-amylase may be an alpha-amylase which displays immunological cross-reactivity with an antibody raised against an alpha-amylase having one of the amino acid sequences selected from the group consisting of SEQ ID NO: 2, 4, 6, 8, 10, 12, 14, 16, 18, 20, 22, 24 and 26. In a preferred embodiment, the parent alpha-amylase is one wherein the antibody raised against the parent alpha-amylase displays an affinity or avidity for an alpha-amylase having one of the amino acid sequences shown in SEQ ID NO: 2, 4, 6, 8, 10, 12, 14, 16, 18, 20, 22, 24 or 26 in a competitive assay technique such as, e.g., ELISA or BiaCore, respectively, or that displays an affinity or avidity that is comparable to that of the parent alpha-amylase, and wherein the antibody raised against the alpha-amylase having one of the amino acid sequences shown in SEQ ID NO: 2, 4, 6, 8, 10, 12, 14, 16, 18, 20, 22, 24 or 26 displays in said competitive assay technique an affinity or avidity for the parent alpha-amylase that is comparable with the affinity or avidity for the alpha-amylase having one of the amino acid sequences shown in SEQ ID NO: 2, 4, 6, 8, 10, 12, 14, 16, 18, 20, 22, 24 or 26. In further embodiments, the parent alpha-amylase is one which has an affinity or avidity which is at least 70%, preferred at least 75% preferred at least 80%, preferred at least 85%, preferred at least 90%, preferred at least 95%, preferred at least 100%, preferred at least 110%, preferred at least 120%, especially preferred at least 125% of the affinity or avidity of the alpha-amylase having one of the amino acid sequences shown in SEQ ID NO: 2, 4, 6, 8, 10, 12, 14, 16, 18, 20, 22, 24 or 26.

The parent alpha-amylase may also be an alpha-amylase which is encoded by a DNA sequence which hybridizes to the DNA sequence encoding the above-specified alpha-amylases, which are apparent from SEQ ID NO: 1, 3, 5, 7, 9, 11, 13, 15, 17, 19, 21, 23 or 25 of the present application. Thus one embodiment concerns a variant alpha-amylase of a parent alpha-amylase, where the parent alpha-amylase is:

(A) derived from a strain of *B. licheniformis, B. amyloliquefaciens, B. stearothermophilus, Bacillus* sp. or KSM AP1378, (B) selected from the group having amino acid sequences as shown in SEQ ID NO: 2, 4, 6, 8, 10, 12, 14, 16, 18, 20, 22, 24 or 26, (C) having a sequence identity to one of SEQ ID NO: 2, 4, 6, 8, 10, 12, 14, 16, 18, 20, 22, 24 or 26 of at least 70%, preferably at least 80%, more preferably at least about 90%, even more preferably at least 95%, even more preferably at least 97%, and even more preferably at least 99%, or (D) encoded by a nucleic acid sequence, which hybridizes under low, preferably medium, preferred high stringency conditions, with the nucleic acid sequence of one of SEQ ID NO: 1, 3, 5, 7, 9, 11, 13, 15, 17, 19, 21, 23 or 25.

In one aspect, the parent polypeptide having amylolytic enhancing activity is (a) a polypeptide comprising an amino acid sequence having at least 60% identity with the mature polypeptide of SEQ ID NO: 2, 4, 6, 8, 10, 12, 14, 16, 18, 20, 22, 24 or 26; (b) a polypeptide encoded by a polynucleotide that hybridizes under at least low stringency conditions with (i) the mature polypeptide coding sequence of SEQ ID NO: 1, 3, 5, 7, 9, 11, 13, 15, 17, 19, 21, 23 or 25, (ii) the genomic DNA sequence comprising the mature polypeptide coding sequence of SEQ ID NO: 1, 3, 5, 7, 9, 11, 13, 15, 17, 19, 21, 23 or 25, or (iii) a full-length complementary strand of (i) or (ii); or (c) a polypeptide encoded by a polynucleotide comprising a nucleotide sequence having at least 60% identity with the mature polypeptide coding sequence of SEQ ID NO: 1, 3, 5, 7, 9, 11, 13, 15, 17, 19, 21, 23 or 25.

When a particular variant of a parent alpha-amylase is referred to—in a conventional manner—by reference to modification (e.g., deletion or substitution) of specific amino acid residues in the amino acid sequence of a specific alpha-amylase, it is to be understood that variants of another alpha-amylase modified in the equivalent position(s) (as determined from the best possible amino acid sequence alignment between the respective amino acid sequences) are encompassed thereby.

In a particular aspect of the invention the parent alpha-amylase is a variant of a naturally occurring (wild type), prepared by any suitable means. For instance, the parent alpha-amylase may be a variant of a naturally occurring alpha-amylase which has been modified or altered in the amino acid sequence.

The parent alpha-amylase may be a substantially homologous parent alpha-amylase which may have one or more (several) amino acid substitutions, deletions and/or insertions. These changes are preferably of a minor nature, that is conservative amino acid substitutions as described below and other substitutions that do not significantly affect the three-dimensional folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, or protein A (Nilsson et al., 1985, *EMBO J.* 4: 1075; Nilsson et al., 1991, *Methods Enzymol.* 198: 3. See, also, in general, Ford et al., 1991, *Protein Expression and Purification* 2: 95-107.

Although the changes described above preferably are of a minor nature, such changes may also be of a substantive nature such as fusion of larger polypeptides of up to 300 amino acids or more both as amino- or carboxyl-terminal extensions.

When a particular variant of a parent alpha-amylase (variant of the invention) is referred to—in a conventional manner—by reference to modification (e.g., deletion or substitution) of specific amino acid residues in the amino acid sequence of a specific parent alpha-amylase, it is to be understood that variants of another parent alpha-amylase modified in the equivalent position(s) (as determined from the best possible amino acid sequence alignment between the respective amino acid sequences) are encompassed thereby.

Homology (Sequence Identity)

The homology may be determined as the degree of identity between the two sequences indicating a derivation of the first sequence from the second. For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of Alignment−Total Number of Gaps in Alignment).

The homology or sequence identity may also be determined as the degree of identity between the two sequences indicating a derivation of the first sequence from the second. The homology may suitably be determined by means of older computer programs known in the art such as GAP provided in the GCG program package. Thus, Gap GCGv8 may be used with the default scoring matrix for identity and the following default parameters: GAP creation penalty of 5.0 and GAP extension penalty of 0.3, respectively for nucleic acidic sequence comparison, and GAP creation penalty of 3.0 and GAP extension penalty of 0.1, respectively, for protein sequence comparison. GAP uses the method of Needleman and Wunsch, 1970, *J. Mol. Biol.* 48: 443-453, to make alignments and to calculate the identity.

A structural alignment between, e.g., Termamyl and an alpha-amylase may be used to identify equivalent/corresponding positions in other alpha-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., 1987, *FEBS Letters* 224 149-155) and reverse threading (Huber and Torda, 1998, *Protein Science* 7(1): 142-149. Properties of the alpha-amylases, i.e., the immunological cross reactivity, may be assayed using an antibody raised against, or reactive with, at least one epitope of the relevant Termamyl-like alpha-amylase. The antibody, which may either be monoclonal or polyclonal, may be produced by methods known in the art, e.g., as described by Hudson et al., Practical Immunology, Third edition (1989), Blackwell Scientific Publications. The immunological cross-reactivity may be determined using assays known in the art, examples of which are Western Blotting or radial immunodiffusion assay, e.g., as described by Hudson et al., 1989.

Hybridisation

In one aspect, the parent polypeptide having amylolytic activity is encoded by a polynucleotide that hybridizes under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, 3, 5, 7, 9, 11, 13, 15, 17, 19, 21, 23 or 25, (ii) the genomic DNA sequence comprising the mature polypeptide coding sequence of SEQ ID NO: 1, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual,* 2d edition, Cold Spring Harbor, New York). The subsequence may encode a polypeptide fragment having amylolytic activity. In one aspect, the complementary strand is the full-length complementary strand of the mature polypeptide coding sequence of SEQ ID NO: 1, 3, 5, 7, 9, 11, 13, 15, 17, 19, 21, 23 or 25.

An oligonucleotide probe used in the characterization of the alpha-amylase in accordance with the desired property which may be alpha-amylase activity may suitably be prepared on the basis of the full or partial nucleotide or amino acid sequence of the alpha-amylase in question.

Suitable conditions for testing hybridization involve presoaking in 5×SSC (standard sodium citrate, 1×SSC corresponds to 0.1650 M NaCl) and prehybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP (adenosine triphosphate) for 18 hours at ~40° C., followed by three times washing of the filter in 2×SSC, 0.2% SDS (sodium dodecylsulfate) at 40° C. for 30 minutes (low stringency), preferred at 50° C. (medium stringency), more preferably at 65° C. (high stringency), even more preferably at ~75° C. (very high stringency). More details about the hybridization method can be found in Sambrook et al., Molecular Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant, which is the result of a modification (insertion, substitution, deletion) of one or more amino acid residues of the naturally occurring alpha-amylase.

Methods for Preparing Alpha-Amylase Variants

Several methods for introducing mutations into genes are known in the art. After a brief discussion of the cloning of alpha-amylase-encoding DNA sequences, methods for generating mutations at specific sites within the alpha-amylase-encoding sequence will be discussed.

Cloning a DNA Sequence Encoding an Alpha-Amylase

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labeled oligonucleotide probes may be synthesized and used to identify alpha-amylase-encoding clones from a genomic library prepared from the organism in question. Alternatively, a labeled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., the phosphoroamidite method described by Beaucage and Caruthers, 1981, *Tetrahedron Letters* 22: 1859 or the method described by Matthes et al., 1984, *EMBO J.* 3: 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or Saiki et al., 1988, *Science* 239(4839): 487-491.

Site-Directed Mutagenesis

Once an alpha-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., 1984, *Biotechnology* 2: 636-639. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localised or region-specific random mutagenesis in at least three parts of the gene translating to the amino acid sequence shown in question, or within the whole gene.

The random mutagenesis of a DNA sequence encoding a parent alpha-amylase may be conveniently performed by use of any method known in the art.

In relation to the above, a further aspect of the present invention relates to a method for generating a variant of a parent alpha-amylase, e.g., wherein the variant exhibits an altered starch affinity relative to the parent, the method comprising:

(a) subjecting a DNA sequence encoding the parent alpha-amylase to random mutagenesis, (b) expressing the mutated DNA sequence obtained in step (a) in a host cell, and (c) screening for host cells expressing an alpha-amylase variant which has an altered starch affinity relative to the parent alpha-amylase.

Step (a) of the above method of the invention is preferably performed using doped primers. For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one, which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties. When the mutagenesis is performed by the use of an oligonucleotide, the oligonucleotide may be doped or spiked with the three non-parent nucleotides during the synthesis of the oligonucleotide at the positions, which are to be changed. The doping or spiking may be done so that codons for unwanted amino acids are avoided. The doped or spiked oligonucleotide can be incorporated into the DNA encoding the alpha-amylase enzyme by any published technique, using e.g., PCR, LCR or any DNA polymerase and ligase as deemed appropriate. Preferably, the doping is carried out using "constant random doping", in which the percentage of wild type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program, which, inter alia, ensures that introduction of stop codons is avoided. When PCR-generated mutagenesis is used, either a chemically treated or non-treated gene encoding a parent alpha-amylase is subjected to PCR under conditions that increase the misincorporation of nucleotides (Deshler 1992, Genetic Analysis: Biomolecular Engineering, 9(4), pp 103-106; Leung et al., 1989, Technique, Vol. 1, pp. 11-15). A mutator strain of *E. coli* (Fowler et al., 1974, *Molec. Gen. Genet.*, 133, pp. 179-191), *S. cerevisiae* or any other microbial organism may be used for the random mutagenesis of the DNA encoding the alpha-amylase by, e.g., transforming a plasmid containing the parent glycosidase into the mutator strain, growing the mutator strain with the plasmid and isolating the mutated plasmid from the mutator strain. The mutated plasmid may be subsequently transformed into the expression organism. The DNA sequence to be mutagenized may be conveniently present in a genomic or cDNA library prepared from an organism expressing the parent alpha-amylase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence. In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme. Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram-negative bacteria such as *E. coli*. The mutated DNA sequence may further comprise a DNA sequence encoding functions permitting expression of the mutated DNA sequence.

Localised Random Mutagenesis

The random mutagenesis may be advantageously localised to a part of the parent alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative Methods of Providing Alpha-Amylase Variants

Alternative methods for providing variants of the invention include gene-shuffling method known in the art including the methods e.g., described in WO 95/22625 (from Affymax Technologies N.V.) and WO 96/00343 (from Novo Nordisk A/S).

Expression of Alpha-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector, which may conveniently be subjected to recombinant DNA procedures, and the choice of vector will often depend on the host cell into which it is to be introduced. Thus, the vector may be an autonomously replicating vector, i.e., a vector, which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question.

Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a pre-region permitting secretion of the expressed protease into the culture medium. If desirable, this pre-region may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gramnegative bacteria such as *E. coli*. The transformation of the bacteria may, for instance, be effected by protoplast transformation or by using competent cells in a manner known per se.

The yeast organism may favourably be selected from a species of *Saccharomyces* or *Schizosaccharomyces*, e.g., *Saccharomyces cerevisiae*. The filamentous fungus may advantageously belong to a species of *Aspergillus*, e.g., *Aspergillus oryzae* or *Aspergillus niger. Fungal cells may be transformed by a process involving protoplast formation and transformation of the protoplasts followed by regeneration of the cell wall in a manner known per se. A suitable procedure for transformation of Aspergillus* host cells is described in EP 238 023.

In yet a further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Conventions for Designation of Variants

Using the numbering system originating from the amino acid sequence of the alpha-amylase disclosed in SEQ ID NO: 6 aligned with the amino acid sequence of a number of other alpha-amylases, it is possible to indicate the position of an amino acid residue in an alpha-amylase in regions of structural homology.

In describing the various alpha-amylase variants of the present invention, the nomenclature described below is adapted for ease of reference. In all cases, the accepted IUPAC single letter or triple letter amino acid abbreviation is employed.

In the present description and claims, the conventional one-letter and three-letter codes for amino acid residues are used. For ease of reference, alpha-amylase variants of the invention are described by use of the following nomenclature:

Original amino acid(s): position(s): substituted amino acid(s)

According to this nomenclature, for instance the substitution of alanine for asparagine in position 30 is shown as:

Ala30Asn or A30N a deletion of alanine in the same position is shown as:

Ala30* or A30* and an insertion of an additional amino acid residue after position 30, such as lysine, is shown as:

Ala30AlaLys or A30AK

A deletion of a consecutive stretch of amino acid residues, such as amino acid residues 30-33, is indicated as (30-33)* or Δ(A30-N33). Deletion of a single amino acid residue may simply be disclosed as 30*.

Where a specific alpha-amylase contains a "deletion" in comparison with other alpha-amylases and an insertion is made in such a position this is indicated as:

*36Asp or *36D for an insertion of an aspartic acid in position 36.

Multiple mutations may be separated by plus signs or with a space, i.e.:

Ala30Asn+Glu34Ser or A30N+E34S

Ala30Asn Glu34Ser or A30N E34S representing mutations in positions 30 and 34 substituting alanine and glutamic acid for asparagine and serine, respectively.

Alternatively multiple mutations may be separated by commas or semicolons, i.e.:

Ala30Asn, Glu34Ser or A30N, E34S

Even more simplified multiple mutations may be separated by a space.

Alternatively, multiple mutations may be separated by commas or semicolons, i.e.:

Ala30Asn Glu34Ser or A30N E34S

When one or more alternative amino acid residues may be inserted in a given position it is indicated as A30N,E or A30N or A30E Alternatively, one or more alternative amino acid residues may be inserted in a given position it is indicated as:

A30 [N, E] or A30 [N E], alternatively A30 {N, E} or A30 {N E}

For simplicity alternative amino acid which could be substituted at a certain position may be indicated as:

A30 N, E, H, L or V

Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of:

R,N,D,A,C,Q,E,G,H,I,L,K,M,F,P,S,T,W,Y,V.

Further, "A30X" means any one of the following substitutions:

A30R, A30N, A30D, A30C, A30Q, A30E, A30G, A30H, A301, A30L, A30K, A30M, A30F, A30P, A30S, A30T, A30W, A30Y, or A30 V; or in short: A30R,N,D,C,Q,E,G,H,I,L,K,M,F,P,S,T,W,Y,V.

Or, e.g., A30 [R, N, D, C, Q, E, G, H, I, L, K, M, F, P, S, T, W, Y, V]

The skilled person would know that using numbering, e.g., according to SEQ ID NO: 6 means using SEQ ID NO: 6 for countering not that the parent necessarily is SEQ ID NO: 6 but simply that the positions to be altered are defined according to SEQ ID NO: 6. Therefore, another way of describing the specific substitutions is to indicate the amino acid to be altered with an X. Thus, X30N means that any amino acid present at position 30 could be substituted with N reflecting that different alpha-amylase can be used as parent alpha-amylase.

Thus, the nomenclature "X30N" or "X30V" means that any amino acid which might be at position 30 in the parent alpha-amylase is substituted by an asparagine or a valine.

Characteristics of Amino Acid Residues

Charged Amino Acids:

Asp, Glu, Arg, Lys, His

Negatively Charged Amino Acids (with the Most Negative Residue First):

Asp, Glu

Positively Charged Amino Acids (with the Most Positive Residue First):

Arg, Lys, His

Neutral Amino Acids:

Gly, Ala, Val, Leu, Ile, Phe, Tyr, Trp, Met, Cys, Asn, Gln, Ser, Thr, Pro

Hydrophobic amino acid residues (with the most hydrophobic residue listed last):

Gly, Ala, Val, Pro, Met, Leu, Ile, Tyr, Phe, Trp

Hydrophilic amino acids (with the most hydrophilic residue listed last):

Thr, Ser, Cys, Gln, Asn

This nomenclature is particularly relevant to modifications involving substituting, inserting or deleting amino acid residues having specific common properties. Such modifications are referred to as conservative amino acid modification(s). Examples of conservative modifications are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid modifications, which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as the reverse (Taylor, 1986, *Journal of Theoretical Biology* 119: 205-218.

Variants of the Invention

In a preferred embodiment the variants comprise alteration(s) in one or more, or one or several, amino acid residues in the region 193 to 213 of the parent alpha-amylase. In a particularly preferred embodiment the variant comprising at least one, at least two, or at least three deletions in amino acid region of 181, 182, 183, or 184 and further an altering at one or more, or one or several, amino acid residues in the region 193 to 213, wherein the numbering corresponds to the mature polypeptide of SEQ ID NO: 6, i.e., using numbering according to SEQ ID NO: 6. The inventors have found that such alterations provides variants having an increased stability in compositions comprising a chelating agent, in particular when the chelating agents capable of reducing the concentration of free calcium ions from 2.0 mM to 0.10 mM at a concentration below 10 mM, preferably below 9.5 mM, preferably below 9.0 mM, preferably below 8.5 mM, preferably below 8.0 mM, preferably below 7.5 mM, preferably below 7.0 mM, preferably below 6.5 mM, preferably below 6.0 mM, preferably below 5.5 mM, preferably, preferably below 5.0 mM, preferably below 4.5 mM, below 4.0 mM, preferably below 3.5 mM, preferably below 3.0 mM, preferably below 2.5 mM, preferably below 2.0 mM, preferably below 1.5 mM or preferably below 1.0 mM when measured at 21° C. and pH 8.0, as described in the below under "Materials and Methods".

A first aspect of the invention relates to a composition comprising a variant of a parent alpha-amylase, wherein the variant comprises a substitution at one or more positions in the range 193 to 213, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0.

A first aspect of the invention relates to a composition comprising a variant of a parent alpha-amylase, wherein the variant comprises a substitution at one or more positions in the range 193 to 213, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0, and optionally a cleaning adjunct.

A second aspect provides a composition comprising a variant of a parent alpha-amylase wherein the variant alpha-amylase comprises an amino acid sequence which is at least 70%, such as at least 75%, such as at least 80%, such as at least 85%, such as at least 90%, such as at least 95%, such as at least 100% identical to SEQ ID NO: 6, 8, 10, 12, 18, and 22 and further comprises a substitution at one or more positions selected from the group comprising 195, 193, 197, 198, 200, 203, 206, 210, 212 213 and 243 using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0.

A further aspect provides a composition comprising a variant which comprises a substitution at one or more positions selected from the group comprising 195, 193, 197, 198, 200, 203, 206, 210, 212, 213 and 243 (using the numbering according to SEQ ID NO: 6) wherein said composition further comprises at least one chelating agent wherein said chelating agent at a concentration below 10 mM is capable of reducing the concentration of free calcium ions from 2.0 mM to 0.10 mM when measured at 21° C. and pH 8.0.

A further aspect provides a composition comprising a variant which comprises a substitution at one or more positions selected from the group comprising 195, 193, 197, 198, 200, 203, 206, 210, 212, 213 and 243 (using the numbering according to SEQ ID NO: 6) and wherein the variant comprise an amino acid sequence having at least 70% identity to amino acid sequence from the group consisting of SEQ ID NO: 2, 4, 6, 8, 10, 12, 14, 16, 18, 20, 22, 24 and 26, preferably SEQ ID NO: 14, 16 or 20, preferably SEQ ID NO: 6, SEQ ID NO: 8, SEQ ID NO: 10, SEQ ID NO: 12, SEQ ID NO: 18, or SEQ ID NO: 22 and wherein said composition further comprises at least one chelating agent wherein said chelating agent at a concentration below 10 mM is capable of reducing the concentration of free calcium ions from 2.0 mM to 0.10 mM when measured at 21° C. and pH 8.0.

A further aspect provides a composition comprising a variant which comprises a substitution at one or more positions selected from the group comprising 195, 193, 197, 198, 200, 203, 206, 210, 212, 213 and 243 (using the numbering according to SEQ ID NO: 6) and wherein the variant comprise an amino acid sequence having at least 70% identity to amino acid sequence from the group consisting of SEQ ID NO: 14, SEQ ID NO: 16 or SEQ ID NO: 20 and wherein said composition further comprises at least one chelating agent wherein said chelating agent at a concentration below 10 mM is capable of reducing the concentration of free calcium ions from 2.0 mM to 0.10 mM when measured at 21° C. and pH 8.0.

A third aspect relates to a composition wherein the chelating agent at a concentration below 10 mM is capable of reducing the concentration of free calcium ions from 2.0 mM to 0.10 mM when measured in 80 mM potassium chloride and 49 mM EPPS at 21° C. and pH 8.0.

A third aspect relates to a composition wherein the chelating agent at a concentration below 10 mM is capable of reducing the concentration of free calcium ions from 2.0 mM to 0.10 mM when measured in the assay described under "Materials and Methods".

Thus, in a preferred aspect of the invention the variant comprises at least one substitution at one or more position in the range corresponding to positions 193 to 213 of the mature polypeptide of SEQ ID NO: 6. The terms "using the numbering according to" or "corresponding to" are used interchangeably in the application and refers to the numbering system used in the present application. Thus position 195 is the amino acid corresponding to position 195 in SEQ ID NO: 6. Thus it is to be understood that variants of other parent alpha-amylases modified in the equivalent position(s) (as determined from the best possible amino acid sequence alignment between the respective amino acid sequences) are encompassed thereby. When there are deletions the countering is made as if no deletions were present.

In a particularly preferred embodiment the composition comprises a variant, which variant comprises an altering at one or more positions corresponding to positions selected from the group consisting of 193, 195, 197, 198, 200, 203, 206, 210, 212, 213 and 243 and an altering at one or more positions corresponding to positions selected from the group consisting of 116, 118, 129, 133, 134, 142, 146, 147, 149, 151, 152, 169, 174, 186, 235, 244, 303, 320, 339, 359, 418, 431, 434, 447, 458 (using numbering according to SEQ ID NO: 6).

In a particularly preferred embodiment the composition comprises a variant, which variant comprises at least one, at least two, or at least three deletions in amino acid region of 181, 182, 183, or 184 and further an alteration at one or more, or one or several, positions corresponding to positions selected from the group consisting of 193, 195, 197, 198, 200, 203, 206, 210, 212, 213 and 243 and an altering at one or more, or one or several, positions corresponding to positions selected from the group consisting of 116, 118, 129, 133, 134, 142, 146, 147, 149, 151, 152, 169, 174, 186, 235, 244, 303, 320, 339, 359, 418, 431, 434, 447, 458 (using numbering according to SEQ ID NO: 6).

In one aspect of the present invention the composition comprises a variant of a parent alpha-amylase comprising at least one, at least two, or at least three deletions in amino acid region of 181, 182, 183, or 184 and further comprises a substitution at one or more, or one or several, positions selected from the group consisting of 193, 195, 197, 198, 200, 203, 206, 210, 212, 213 and 243, using the numbering according to SEQ ID NO: 6, and wherein the variant has an amino acid sequence having a degree of identity of at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably SEQ ID NO: 14, 16 or 20, preferably SEQ ID NO: 6, 8, 10, 12, 18, or 22, and wherein the variant has at least 70% residual activity, preferably at least 75% residual activity, preferably at least 80% residual activity, preferably at least 85% residual activity, preferably at least 90% residual activity, preferably at least 95% residual activity, preferably at least 100% residual activity, preferably at least 105% residual activity, preferably at least 110% residual activity or has a residual activity which is at least 5, 10, 20, 30, 40, 50, 60, 70, 80, 90, 100 pp improved compared to the residual activity of the parent alpha-amylase, when the residual activity is determined after 18 hours at pH 8 and 31° C. as described in the EnzChek or the PNP-G7 assay (see under "Materials and Methods" for details) in the presence of a chelating agent wherein said chelating agent at a concentration below 10 mM is capable of reducing the concentration of free calcium ions from 2.0 mM to 0.10 mM when measured at 21° C. and pH 8.0, as described below.

The composition according to the invention preferably comprising an alpha-amylase wherein the parent alpha-amylase is modified by at least one of the following substitutions: position 193 is [G,A,S,T, or M]; position 195 is [F,W,Y,L,I, or V]; position 197 is [F,W,Y,L,I, or V]; position 198 is [Q or N]; position 200 is [F,W,Y,L,I, or V]; position 203 is [F,W,Y,L,I, or V]; position 206 is [F,W,Y,N,L,I,V, or H]; position 210 is [F,W,Y,L,I, or V]; position 212 is [F,W,Y,L,I, or V] or position 213 is [G,A,S,T, or M] wherein the positions corresponds to the position of the mature polypeptide with SEQ ID NO: 6 and further comprising at least one chelating agent wherein said chelating agent at a concentration below 10 mM is capable of reducing the concentration of free calcium ions from 2.0 mM to 0.10 mM when measured at 21° C. and pH 8.0, as described under "Materials and Methods".

The composition according to the invention preferably comprising an alpha-amylase variant, wherein the variant comprising at least one, at least two, or at least three deletions in amino acid region of 181, 182, 183, or 184 and wherein the parent alpha-amylase further is modified by at least one of the following substitutions: 193 is [G,A,S,T, or M]; position 195 is [F,W,Y,L,I, or V]; position 197 is [F,W,Y,L,I, or V]; position 198 is [Q or N]; position 200 is [F,W,Y,L,I, or V]; position 203 is [F,W,Y,L,I, or V]; position 206 is [F,W,Y,N,L,I,V, or H]; position 210 is [F,W,Y,L,I, or V]; position 212 is [F,W,Y,L,I, or V], position 213 is [G,A,S,T, or M] or position 243 is [F, W, Y, L, I or V] wherein the positions corresponds to the position of the mature polypeptide with SEQ ID NO: 6 and further comprising at least one chelating agent wherein said chelating agent at a concentration below 10 mM is capable of reducing the concentration of free calcium ions from 2.0 mM to 0.10 mM when measured at 21° C. and pH 8.0, as described under "Materials and Methods".

In particular the invention concerns a composition comprising an alpha-amylase wherein the amino acid sequence is modified by at least one of the following substitutions: 193 is T; position 195 is F or Y; position 197 is F or L; position 198 is N; position 200 is F; position 203 is F; position 206 is F, L or Y; position 210 is Y; position 212 is V; position 213 is A position 243 is F, wherein the positions corresponds to the position of the mature polypeptide with SEQ ID NO: 6 and further comprising at least one chelating agent wherein said chelating agent at a concentration below 10 mM is capable of reducing the concentration of free calcium ions from 2.0 mM to 0.10 mM when measured in at 21° C. and pH 8.0, as described under "Materials and Methods".

In a further aspect the composition comprises an alpha-amylase variant, wherein said variant comprises a substitution at two or more, or two or several, positions selected from the group consisting of 193, 195, 197, 198, 200, 203, 206, 210, 212, 213 and 243, wherein the positions correspond to positions of the mature polypeptide of SEQ ID NO: 6 and further comprising at least one chelating agent wherein said chelating agent at a concentration below 10 mM is capable of reducing the concentration of free calcium ions from 2.0 mM to 0.10 mM when measured at 21° C. and pH 8.0, as described under "Materials and Methods".

In yet a further aspect the composition comprises an alpha-amylase variant, wherein the variant comprises at least two or more, or at least three or more, deletions in amino acid region of 181, 182, 183, or 184 and further comprises a substitution at two or more positions selected from the group consisting of 193, 195, 197, 198, 200, 203, 206, 210, 212, 213 and 243 wherein the positions correspond to positions of the mature polypeptide of SEQ ID NO: 6 and further comprising at least one chelating agent wherein said chelating agent at a concentration below 10 mM is capable of reducing the concentration of free calcium ions from 2.0 mM to 0.10 mM when measured at 21° C. and pH 8.0, as described under "Materials and Methods", and wherein the variant has at least 70% residual activity, preferably at least 75% residual activity, preferably at least 80% residual activity, preferably at least 85% residual activity, preferably at least 90% residual activity, preferably at least 95% residual activity, preferably at least 100% residual activity, preferably at least 105% residual activity, preferably at least 110% residual activity or has a residual activity which is at least 5, 10, 20, 30, 40, 50, 60, 70, 80, 90, 100 pp improved compared to the residual activity of the parent alpha-amylase, when the residual activity is determined after 18 hours at pH 8 and 31° C. as described in the EnzChek or the PNP-G7 assay (see under "Materials and Methods" for details) in the presence of a chelating agent wherein said chelating agent at a concentration below 10 mM is capable of reducing the concentration of free calcium ions from 2.0 mM to 0.10 mM when measured at 21° C. and pH 8.0, as described below.

In preferred embodiments the at least two deletions in amino acid region of 181, 182, 183, or 184 is selected from the group consisting of 181*+182*; 181*+183*, 182*+183*; 181*+184*, 182*+184* and 183*+184*.

In an even further aspect, the composition comprises an alpha-amylase variant, wherein the variant comprises at least two, or at least three deletions in amino acid region of 181, 182, 183, or 184 and further comprises a substitution at two or more positions selected from the group consisting of 193, 195, 197, 198, 200, 203, 206, 210, 212, 213 and 243 wherein the positions correspond to positions of the mature polypeptide of SEQ ID NO: 6 and an altering at one or more, or one or several, positions corresponding to positions selected from the group consisting of 116, 118, 129, 133, 134, 142,146, 147, 149, 151, 152, 169, 174, 186, 235, 244, 303, 320, 339, 359, 418, 431, 434, 447, 458 (using numbering according to SEQ ID NO: 6), and further comprising at least one chelating agent wherein said chelating agent at a concentration below 10 mM is capable of reducing the concentration of free calcium ions from 2.0 mM to 0.10 mM when measured at 21° C. and pH 8.0, as described under "Materials and Methods".

In one aspect of the invention, the composition comprises at least one chelating agent wherein said chelating agent at a concentration below 10 mM is capable of reducing the concentration of free calcium ions from 2.0 mM to 0.10 mM when measured at 21° C. and pH 8.0 and one or more, or one or several, of the following amylase variants:

SP722+R181*G182* N195F; SP722+G182* D183* N195F; SP722+D183* G184* N195F; SP722+R181* G182* N195F M202L; SP722+G182 D183* N195F M202L; SP722+D183* G184* N195F M202L; SP722+D183* G184* N195F V206L Y243F; SP722+D183* G184* N195F V206Y Y243F; SP722+R181* G182* L118K N195F R458K; SP722+G182* D183* L118K N195F H458K; SP722+D183* G184* L118K N195F H458K; SP722+D183* G184* G133E G149R N195Y Y203F V206L.

AA560+R181* G182* N195F; AA560+G182* D183* N195F; AA560+D183* G184* N195F; AA560+D183* G184* I206Y; AA560+D183* G184* Y243F; AA560+D183* G184* V206L, Y243F; AA560+D183* G184*

N195F V206L; AA560+D183* G184* N195F Y243F; AA560+D183* G184* N195F V206L Y243F; AA560+D183* G184* N195F V206Y Y243F; AA560+R181* G182* N195F M202L; AA560+G182* D183* N195F M202L; AA560+D183* G184* N195F M202L; AA560+R181* G182* R118K N195F R320K R458K; AA560+G182* D183* R118K N195F R320K R458K; AA560+D183* G184* R118K N195F R320K R458K; AA560+D183* G184* R118K N195F I206L R320K R458K; AA560+D183* G184* R118K N195F I206Y R320K R458K; AA560+D183* G184* R118K N195F Y243F R320K R458K; AA560+D183* G184* R118K N195F I206L Y243F R320K R458K.

SP707+R181* G182* N195F; SP707+G182* H183* N195F; SP707+H183* G184* N195F; SP707+H183* G184* I206Y; SP707+H183* G184* N195F I206Y; SP707+H183* G184* N195F Y243F; SP707+H183* G184* I206Y Y243F; SP707+H183* G184* N195F I206L Y243F; SP707+H183* G184* N195F I206Y Y243F; SP707+R181* G182* N195F M202L; SP707+G182* H183* N195F M202L; SP707+H183* G184* N195F M202L; SP707+R181* G182* R118K N195F R320K R458K; SP707+G182* H183* R118K N195F R320K R458K; SP707+H183* G184* R118K N195F R320K R458K; SP690+R181* G182* N195F; SP690+G182* T183* N195F; SP690+T183* G184* N195F; SP690+H183* G184* V206Y; SP690+H183* G184* N195F V206Y; SP690+H183* G184* N195F Y243F; SP690+H183* G184* V206Y Y243F; SP690+H183* G184* N195F V206L Y243F; SP690+H183* G184* N195F V206Y Y243F; SP690+R181* G182* N195F M202L; SP690+G182* T183* N195F M202L; SP690+T183* G184* N195F M202L; SP690+R181* G182* R118K N195F R320K R458K; SP690+G182* T183* R118K N195F R320K R458K; SP690+T183* G184* R118K N195F R320K R458K.

In useful embodiments, the composition according to the invention comprises an amylase which is a variant of a parent alpha-amylase, wherein the parent alpha-amylase is that of SEQ ID NO:6, and the variant comprises the deletions D183* and G184* and one of the following sets of mutations: (a) N195F+H210Y; (b) N195F+V206L,H,Y; (c) N195F+V206L, F+H210Y; (d) N195F+V206Y+Y243F; (e) N195F+Y243F; (f) S193T+V206L; (g) G133E+G149R+N195Y+Y203F+V206L; (h) V206L,Y; (i) Y243F; (j) N195F+V206L+Y243F; (k) N195F; or (I) V206F+Y243F.

Another embodiment of the invention relates to a composition, wherein the residual activity of the variant is at least 70%, such as at least 75%, such as at least 80%, such as at least 85%, such as at least 90%, such as at least 95%, such as at least 100%, such as at least 105%, such as at least 110%, such as at least 115% residual activity compared to the parent alpha-amylase in the presence of a chelating agent wherein said chelating agent at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM is capable of reducing the concentration of free calcium ions from 2.0 mM to 0.10 mM when measured at 21° C. and pH 8.0, as described under "Materials and Methods" and when residual activity is determined after 18 hours at pH 8 at 31° C. as described in the EnzChek or the PNP-G7 assay described under "Materials and Methods".

A further embodiment of the invention relates to a composition, wherein the residual activity of the variant is at least 5, 10, 20, 30, 40, 50, 60, 70, 80, 90, 100 pp improved compared to the residual activity of the parent alpha-amylase in the presence of a chelating agent wherein said chelating agent at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM is capable of reducing the concentration of free calcium ions from 2.0 mM to 0.10 mM when measured at 21° C. and pH 8.0, as described under "Materials and Methods" and when residual activity is determined after 18 hours at pH 8 at 31° C. as described in the EnzChek or the PNP-G7 assay described under "Materials and Methods". The percentage point (pp) improvement in residual activity of the variant relative to the parent is calculated as the difference between the residual activity of the variant and that of the parent.

Thus, in a particular aspect of the invention the composition comprises a chelating agent selected from the group consisting of: phosphorous-containing, non-phosphorous containing, carboxylate containing, nitrogen containing or non-nitrogen containing chelating agents, preferred chelating agents are as EDTA, MGDA, EGTA, DTPA, DTPMP, HEDP and mixtures thereof.

In a preferred aspect of the invention the variant comprises a substitution at one or more positions selected from the group consisting of 195, 193, 197, 198, 200, 203, 206, 210, 212 and 213 wherein the positions correspond to positions of the mature polypeptide of SEQ ID NO: 6.

In a particularly preferred aspect of the invention the variant comprising at least one, at least two, or at least three deletions in amino acid region of 181, 182, 183, or 184 and further comprises a substitution at one or more positions selected from the group consisting of 195, 193, 197, 198, 200, 203, 206, 210, 212 213 and 243 wherein the positions correspond to positions of the mature polypeptide of SEQ ID NO: 6. In preferred embodiments the at least two deletions in the amino acid region of 181, 182, 183, or 184 is selected from the group consisting of 181*+182*; 181*+183*, 182*+183*; 181*+184*, 182*+184* and 183*+184*.

In another preferred aspect of the invention the variant comprises a substitution at one or more positions selected from the group consisting of 195, 193, 197, 198, 200, 203, 206, 210, 212, 213 and 243 and further comprises a substitution at one or more, or one or several, positions selected from the group consisting of 116, 118, 129, 133, 134, 142, 146, 147, 149, 151, 152, 169, 174, 186, 235, 244, 303, 320, 339, 359, 418, 431, 434, 447, 458 wherein the positions correspond to positions of the mature polypeptide of SEQ ID NO: 6.

In a yet preferred aspect of the invention the variant comprising at least one, at least two, or at least three deletions in amino acid region of 181, 182, 183, or 184 and further comprises a substitution at one or more positions selected from the group consisting of 195, 193, 197, 198, 200, 203, 206, 210, 212, 213 and 243 and further comprises a substitution at one or more positions selected from the group consisting of 116, 118, 129, 133, 134, 142, 146, 147, 149, 151, 152, 169, 174, 186, 235, 244, 303, 320, 339, 359, 418, 431, 434, 447, 458 wherein the positions correspond to positions of the mature polypeptide of SEQ ID NO: 6.

In a further aspect the variant comprises a substitution at two or more positions selected from the group consisting of 116, 118, 129, 133, 134, 142, 146, 147, 149, 151, 152, 169, 174, 186, 193, 195, 197, 198, 200, 203, 206, 210, 212, 213, 235, 243, 244, 303, 320, 339, 359, 418, 431, 434, 447 and 458 wherein the positions correspond to positions of the mature polypeptide of SEQ ID NO: 6.

In yet a further aspect the variant comprising at least one, at least two, or at least three deletions in amino acid region of 181, 182, 183, or 184 and further comprises a substitution at two or more positions selected from the group consisting of 116, 118, 129, 133, 134, 142, 146, 147, 149, 151, 152, 169, 174, 186, 193, 195, 197, 198, 200, 203, 206, 210, 212, 213, 235, 243, 244, 303, 320, 339, 359, 418, 431, 434, 447 and 458 wherein the positions correspond to positions of the mature polypeptide of SEQ ID NO: 6.

Preferably, the variants comprising alterations at one or more of the above identified positions have an increased stability in compositions comprising a chelating agent, e.g., in detergent, preferably in liquid detergent as compared to the parent alpha-amylase.

Thus, the variants according to the invention have in a preferred embodiment improved stability relative to its parent amylase in the presence of one or more chelating agents. In a preferred aspect the variants according to the invention have improved stability relative to its parent amylase in the presence of one or more chelating agents and low calcium concentration. In yet a preferred aspect the variants according to the invention have improved stability relative to its parent amylase in presence of a chelating agent wherein said chelating agent at a concentration below 10 mM is capable of reducing the concentration of free calcium ions from 2.0 mM to 0.10 mM when measured at 21° C. and pH 8.0.

In a particular aspect the variant comprising at least one, at least two, or at least three deletions in amino acid region of 181, 182, 183, or 184 and further comprising a substitution at one or more position selected from the group consisting of 193, 195, 197, 198, 200, 203, 206, 210, 212, 213 and 243 and a substitution at one or more positions selected from the group consisting of 116, 118, 129, 133, 134, 142, 146, 147, 149, 151, 152, 169, 174, 186, 235, 244, 303, 320, 338, 359, 418, 431, 434, 447 and 458 wherein the positions correspond to positions of the mature polypeptide of SEQ ID NO: 6 and wherein the variant further has at least 60%, such as at least 65%, such as at least 70%, such as at least 75%, such as at least 80%, such as at least 85%, such as at least 90%, such as at least 95%, such as at least 100% residual activity in the presence of a chelating agent wherein said chelating agent at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM is capable of reducing the concentration of free calcium ions from 2.0 mM to 0.10 mM at 21° C. and pH 8.0, as described below, and when residual activity is determined after 18 hours at pH 8, at 31° C. as described in the EnzChek assay or the PNP-G7 assay described under "Materials and Methods". In preferred embodiments the at least two deletions in the amino acid region of 181, 182, 183, or 184 is selected from the group consisting of 181*+182*; 181*+183*, 182*+183*; 181*+184*, 182*+184* and 183*+184*.

In a another particular aspect the variant comprises a substitution at one or more positions selected from the group consisting of 193, 195, 197, 198, 200, 203, 206, 210, 212, 213 and 243 and further comprising a substitution at one or more positions selected from the group consisting of 116, 118, 129, 133, 134, 142, 146,147, 149, 151, 152, 169, 174, 186, 235, 244, 303, 320, 339, 359, 418, 431, 434, 447 and 458 wherein the positions correspond to positions of the mature polypeptide of SEQ ID NO: 6 and wherein the variant further has at least 60%, such as at least 65%, such as at least 70%, such as at least 75%, such as at least 80%, such as at least 85%, such as at least 90%, such as at least 95%, such as at least 100% residual activity or has a residual activity which is at least 5, 10, 20, 30, 40, 50, 60, 70, 80, 90, 100 pp improved compared to the residual activity of the parent alpha-amylase in the presence of a chelating agent wherein said chelating agent at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM is capable of reducing the concentration of free calcium ions from 2.0 mM to 0.10 mM when measured at 21° C. and pH 8.0, as described under "Materials and Methods" and when residual activity is determined after 18 hours at pH 8 in the presence of DTPA at 31° C. as described in the EnzChek assay or the PNP-G7 assay described under "Materials and Methods".

The variants according to the invention have the benefit of being more stable towards strong chelating agents relative to their parent alpha-amylase however at the same time they have maintained the performance properties of the parent alpha-amylase such as wash performance or dish wash performance. In a preferred embodiment the variants according to the invention have the benefit of being more stable towards chelating agents wherein said chelating agent at a concentration below 10 mM is capable of reducing the concentration of free calcium ions from 2.0 mM to 0.10 mM when measured in 80 mM potassium chloride and 49 mM EPPS, at 21° C. and pH 8.0, as described under "Materials and Methods". These preferred chelating agents may be selected from, but are not restricted to, the EDTA, MGDA, EGTA, DTPA, DTPMP HEDP and mixtures thereof.

Thus, the variants of the invention have increased stability in the presence of chelating agents binding metal ions in particular calcium ions compared to their parent alpha-amylase. In detergents it is common to include chelating agents because of the beneficial effect of the laundering process, but the increased stability may also be at conditions where plant material including natural chelating agents such as phytate or citrate is present. In particular a strong chelating agents will compete with the calcium sensitive alpha-amylases for the calcium ions and will to some extend be able to deprive the alpha-amylase for the calcium ions bound in their structure with the consequence that the stability or activity of the alpha-amylase is reduced.

Thus, the variants of the invention have improved stability and/or activity in the presence of chelating agents, such as EDTA, MGDA, EGTA, DTPA, DTPMP HEDP and mixtures thereof, compared to their parent alpha-amylase.

In addition to increased stability towards chelating agents relative to the parent alpha-amylase the variants of the present invention have retained or improved wash performance when compared to the parent alpha-amylase. The improved wash performance can be measured in AMSA or in a wash performance test using beakers as described under "Materials and Methods".

Thus, in a particular embodiment of the invention the variant has at least 60% such as at least 65% residual activity, preferably at least 70% residual activity, preferably at least 75% residual activity, preferably at least 80% residual activity, preferably at least 85% residual activity, preferably at least 90% residual activity, preferably at least 95% residual activity or has a residual activity which is at least 5, 10, 20, 30, 40, 50, 60, 70, 80, 90, 100 pp improved compared to the residual activity of the parent alpha-amylase, when the residual activity is determined after 18 hours at pH 8 and 31° C. as described in the EnzChek or the PNP-G7 assay (see under "Materials and Methods" for details) in the presence of a chelating agent wherein said chelating agent at a concentration below 10 mM is capable of reducing the concentration of free calcium ions from 2.0 mM to 0.10 mM when measured at 21° C. and pH 8.0, as described below and wherein the variant further has at least 40%, such as at least 50%, such as at least 55%, such as at least 60%, such as at least 65%, such as at least 70%, such as at least 75%, such as at least 80%, such as at least 85%, such as at least 90%, such as at least 95%, such as at least 100% improved wash performance compared to the parent alpha-amylase when measured in AMSA or in a wash performance test using beakers as described under "Materials and Methods".

In a preferred aspect of the invention the composition comprises a variant having at least 60%, such as at least 65%, such as at least 70%, such as at least 75%, such as at least 80%, such as at least 85%, such as at least 90%, such as at least 95%, such as at least 100% residual activity compared to the parent alpha-amylase in the presence of a chelating agent wherein said chelating agent at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM is capable of reducing the concentration of free calcium ions from 2.0 mM to 0.10 mM when measured at 21° C. and pH 8.0, as described in example 2a and when residual activity is determined after 18 hours at pH 8 at 31° C. as described in the EnzChek or the PNP-G7 assay described under "Materials and Methods".

Thus, in a particular aspect of the invention the composition comprises a chelating agent selected from the group consisting of: phosphorous-containing, non-phosphorous containing, nitrogen containing or non-nitrogen containing chelating agents, preferred chelating agents are EDTA, MGDA, EGTA, DTPA, DTPMP, HEDP and mixtures thereof.

In a preferred aspect the variants according to the invention have an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably, SEQ ID NO: 6, 8, 10, 12, 18, or 22, preferably SEQ ID NO:14, 16 or 20, preferably SEQ ID NO: 6, 8, 10 or 12.

In one aspect of the present invention, the variants of a parent alpha-amylase comprising at least one, at least two, or at least three deletions in amino acid region of 181, 182, 183, or 184 and further comprises a substitution at one or more positions selected from the group consisting of 193, 195, 197, 198, 200, 203, 206, 210, 212 213 and 243, using the numbering according to SEQ ID NO: 6, and wherein the variant has an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably SEQ ID NO: 14, 16 or 20, preferably SEQ ID NO: 6, 8, 10, 12, 18, or 22, preferably SEQ ID NO: 6, 8, 10 or 12.

In one aspect of the present invention, the variants of a parent alpha-amylase comprising at least one, at least two, or at least three deletions in amino acid region of 181, 182, 183, or 184 and further comprises a substitution at one or more positions selected from the group consisting of 193, 195, 197, 198, 200, 203, 206, 210, 212 213 and 243, using the numbering according to SEQ ID NO 6, and wherein the variant has an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably SEQ ID NO:14, 16 or 20, preferably SEQ ID NO 6, 8, 10, 12, 18, or 22, preferably SEQ ID NO: 6, 8, 10 or 12.

In one further aspect of the present invention, the variant comprises at least one, at least two, or at least three deletions in amino acid region of 181, 182, 183, or 184 and further comprises a substitution at one or more positions selected from the group consisting of 193, 195, 197, 198, 200, 203, 206, 210, 212, 213 and 243, using the numbering according to SEQ ID NO: 6, and wherein the variant has an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence shown in SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18 or 22, preferably SEQ ID NO: 6, 8, 10 or 12.

In another aspect of the invention the variant comprises a substitution at one or more positions 193, 195, 197, 198, 200, 203, 206, 210, 212, 213 or 243 and a substitution at one or more positions 116, 118, 129, 133, 134, 142, 146, 147, 149, 151, 152, 169, 174, 186, 235, 244, 303, 320, 339, 359, 418, 431, 434, 447, 458, using the numbering according to SEQ ID NO: 6, and wherein the variant have an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect of the invention the variant comprising at least one, at least two, or at least three deletions in amino acid region of 181, 182, 183, or 184 and further comprises a substitution at one or more positions 193, 195, 197, 198, 200, 203, 206, 210, 212, 213 or 243 and a substitution at one or more positions 116, 118, 129, 133, 134, 142, 146, 147, 149, 151, 152, 169, 174, 186, 235, 244, 303, 320, 339, 359, 418, 431, 434, 447, 458, using the numbering according to SEQ ID NO: 6, and wherein the variant have an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the number of amino acid substitutions in the variants of the present invention is below 10 substitutions, such as below 9 substitutions, such as below 8 substitutions, such as below 7 substitutions, such as below 6 substitutions, such as below 5 substitutions, such as below 4 substitutions, such as below 3 substitutions, such as below 2 substitutions, and/or wherein the number of deletions is below 10 deletions, such as below 9 deletions, such as below 8 deletions, such as below 7 deletions, such as below 6 deletions, such as below 5 deletions, such as below 4 deletions, such as below 3 deletions, such as below 2 deletions, such as below 1 deletion or the variant may comprise no deletions and/or wherein the number of insertions is below 10 insertions, such as below 9 insertions, such as below 8 insertions, such as below 7 insertions, such as below 6 insertions, such as below 5 insertions, such as below 4 insertions, such as below 3 insertions, such as below 2 insertions, such as below 1 insertions or the variant may comprise no insertions compared to the parent alpha-amylase which may be any of the sequences with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO:14, 16 or 20, preferably SEQ ID NO: 6, 8, 10 or 12.

In one aspect, the variant comprises a substitution at a position corresponding to position 193. In another aspect, the variant comprises a substitution at a position corresponding to position 193 with [G, A, T or M] of the mature polypeptide of SEQ ID NO: 6. In one particular embodiment the variant comprises the substitution S193T of the mature polypeptide of SEQ ID NO: 6. In another aspect, the variant comprising at least one, at least two, or at least three deletions in amino acid region of 181, 182, 183, or 184 and further comprises the substitution S193T, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 195, in a preferred aspect the variant comprises a substitution at position 195 with [F, W, Y, L, I or V], in another preferred aspect, the variant comprises F at position 195, in yet another preferred aspect, the variant comprises the substitution N195F, wherein the parent is any of the mature polypeptides with SEQ ID NO: 6, 8, 10 or 12. In another aspect, the variant comprises Y as a substitution at position 195. In another aspect, the variant comprises the substitution N195Y, wherein the parent alpha-amylase is any of the mature polypeptides with SEQ ID NO: 2, 4, 6, 8, 10, 12, 14, 16, 18, 20, 22, 24 or 26, preferably SEQ ID NO: 14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 195, in a preferred aspect the variant comprises a substitution at position 195 with [F, W, Y, L, I or V], in another preferred aspect, the variant comprises F at position 195, in yet another preferred aspect, the variant comprises the substitution N195F, wherein the parent is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12. In another aspect, the variant comprises Y as a substitution at position 195. In another aspect, the variant comprising at least one, at least two, or at least three deletions in amino acid region of 181, 182, 183, or 184 and further comprises the substitution N195Y, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 197, in a preferred aspect the variant comprises a substitution at position 197 with [F, W, Y, L, I or V], in another preferred aspect, the variant comprises F at position 197, in yet another preferred aspect, the variant comprises the substitution N197F, wherein the parent is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12. In another aspect, the variant comprises L as a substitution at position 197. In another aspect, the variant comprising at least one, at least two, or at least three deletions in amino acid region of 181, 182, 183, or 184 and further comprises the substitution N197L, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 197, in a preferred aspect the variant comprises a substitution at position 197 with [F, W, Y, L, I or V], in another preferred aspect, the variant comprises F at position 197, in yet another preferred aspect, the variant comprises the substitution N197F, wherein the parent is any of the mature polypeptides with SEQ ID NO: 6, 8, 10 or 12. In another aspect, the variant comprises L as a substitution at position 197. In another aspect, the variant comprising at least one, at least two, or at least three deletions in amino acid region of 181, 182, 183, or 184 and further comprises the substitution N197L, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 198, in a preferred aspect the variant comprises a substitution at position 198 with [Q, N, D, E, R, K or H], in another preferred aspect, the variant comprises N at position 198, in yet another preferred aspect, the variant comprises the substitution Y198N, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, 20 or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 198, in a preferred aspect the variant comprises a substitution at position 198 with [Q, N, D, E, R, K or H], in another preferred aspect, the variant comprises F at position 198, in yet another preferred aspect, the variant comprises the substitution Y198N, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 200, in a preferred aspect the variant comprises a substitution at position 200 with [F, W, Y, L, I or V], in another preferred aspect, the variant comprises F at position 200, in yet another preferred aspect, the variant comprises the substitution Y200F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 200, in a preferred aspect the variant comprises a substitution at position 200 with [F, W, Y, L, I or V], in another preferred aspect, the variant comprises F at position 200, in yet another preferred aspect, the variant comprises the substitution Y200F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 203, in a preferred aspect the variant comprises a substitution at position 203 with [F, W, Y, L, I or V], in another preferred aspect, the variant comprises F at position 203, in yet another preferred aspect, the variant comprises the substitution Y203F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 203, in a preferred aspect the variant comprises a substitution at position 203 with [F, W, Y, L, I or V], in another preferred aspect, the variant comprises F at position 203, in yet another preferred aspect, the variant comprises the substitution Y203F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 206, in a preferred aspect the variant comprises a substitution at position 206 with [F,W,Y,N,L,I,V,H,Q,D, or E], in another preferred aspect, the variant comprises F at position 206, in yet another preferred aspect, the variant comprises Y at position 206, in still another aspect the variant comprises L at position 206, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one particular embodiment the variant comprises the substitution V206Y of the mature polypeptide of SEQ ID NO: 6 or 12. In another particular embodiment the variant comprises the substitution I206Y of the mature polypeptide of SEQ ID NO: 8 or 10.

In one particular embodiment the variant comprises the substitution V206F of the mature polypeptide of SEQ ID NO: 6 or 12. In another particular embodiment the variant comprises the substitution I206F of the mature polypeptide of SEQ ID NO: 8 or 10.

In one particular embodiment the variant comprises the substitution V206L of the mature polypeptide of SEQ ID NO: 6 or 12. In another particular embodiment the variant comprises the substitution I206L of the mature polypeptide of SEQ ID NO: 8 or 10.

In one particular embodiment the variant comprises the substitution V206H of the mature polypeptide of SEQ ID NO: 6 or 12. In another particular embodiment the variant comprises the substitution I206H of the mature polypeptide of SEQ ID NO: 8 or 10.

In one aspect, the variant of a parent alpha-amylase comprising at least one, at least two, or at least three deletions in amino acid region of 181, 182, 183, or 184 and further comprises a substitution at position 206, in a preferred aspect the variant comprises a substitution at position 206 with [F,W,Y,N,L,I,V,H,Q,D, or E], in another preferred aspect, the variant comprises F at position 206, in another preferred aspect, the variant comprises Y at position 206.

In one particular embodiment the variant comprising at least one, at least two, or at least three deletions in amino acid region of 181, 182, 183, or 184 and further comprises the substitution V206Y of the mature polypeptide of SEQ ID NO: 6 or 12. In another particular embodiment the variant comprising at least one, at least two, or at least three deletions in amino acid region of 181, 182, 183, or 184 and further comprises the substitution I206Y of the mature polypeptide of SEQ ID NO: 8 or 10.

In one particular embodiment the variant comprising at least one, at least two, or at least three deletions in amino acid region of 181, 182, 183, or 184 and further comprises the substitution V206L of the mature polypeptide of SEQ ID NO: 6 or 12. In another particular embodiment the variant comprising at least one, at least two, or at least three deletions in amino acid region of 181, 182, 183, or 184 and further comprises the substitution I206L of the mature polypeptide of SEQ ID NO: 8 or 10.

In one particular embodiment the variant comprising at least one, at least two, or at least three deletions in amino acid region of 181, 182, 183, or 184 and further comprises the substitution V206H of the mature polypeptide of SEQ ID NO: 6 or 12. In another particular embodiment the variant comprising at least one, at least two, or at least three deletions in amino acid region of 181, 182, 183, or 184 and further comprises the substitution I206H of the mature polypeptide of SEQ ID NO: 8 or 10 In one aspect, the variant of a parent alpha-amylase comprises a substitution at position 210, in a preferred aspect the variant comprises a substitution at position 210 with [F, W, Y, L, I or V], in another preferred aspect, the variant comprises Y at position 210, in yet another preferred aspect, the variant comprises the substitution H210Y, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 210, in a preferred aspect the variant comprises a substitution at position 210 with [F, W, Y, L, I or V], in another preferred aspect, the variant comprises Y at position 210, in yet another preferred aspect, the variant comprises the substitution H210Y, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 212, in a preferred aspect the variant comprises a substitution at position 212 with [F, W, Y, L, I or V], in another preferred aspect, the variant comprises V at position 212, in yet another preferred aspect, the variant comprises the substitution E212V, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 212, in a preferred aspect the variant comprises a substitution at position 212 with [F, W, Y, L, I or V], in another preferred aspect, the variant comprises V at position 212, in yet another preferred aspect, the variant comprises the substitution E212V, wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12.

In one aspect, the variant of a parent alpha-amylase comprises a substitution at position 213, in a preferred aspect the variant comprises a substitution at position 213 with [G, A, S, T or M], in another preferred aspect, the variant comprises A at position 213, in yet another preferred aspect, the variant comprises the substitution V213A, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 213, in a preferred aspect the variant comprises a substitution at position 213 with [G, A, S, T or M], in another preferred aspect, the variant comprises A at position 213, in yet another preferred aspect, the variant comprises the substitution V213A, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 243, in a preferred aspect the variant comprises a substitution at position 243 with [F, W, Y, L, I or V], in another preferred aspect, the variant comprises F at position 243, in yet another preferred aspect, the variant comprises the substitution Y243F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 243, in a preferred aspect the variant comprises a substitution at position 243 with [F, W, Y, L, I or V], in another preferred aspect, the variant comprises A at position 243, in yet another preferred aspect, the variant comprises the substitution Y243F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant comprises substitutions at positions 193 and 195. In another aspect, the variant comprises substitutions at positions 193 and 195 with [F, W, Y, L, I, V, N, G, A, T, M or Q]. In another aspect, the variant comprises T and F as substitutions at positions 193 and 195, respectively. In another aspect, the variant comprises the substitutions S193T+N195F of the mature polypeptide of SEQ ID NO: 6. In another aspect, the variant comprises T and Y as substitutions at positions 193 and 195, respectively. In another aspect, the variant comprises the substitutions S193T+N195Y of the mature polypeptide of SEQ ID NO: 6.

In another aspect, the variant of a parent alpha-amylase comprising at least one, at least two, or at least three deletions in amino acid region of 181, 182, 183, or 184 and further comprises substitutions at positions 193 and 195. In another aspect, the variant comprising at least one, at least two, or at least three deletions in amino acid region of 181, 182, 183, or 184 and further comprises substitutions at positions 193 and 195 with [F, W, Y, L, I, V, N, G, A, T, M or Q]. In another aspect, the variant comprises T and F as substitutions at positions 193 and 195, respectively. In another aspect, the variant comprising at least one, at least two, or at least three deletions in amino acid region of 181, 182, 183, or 184 and further comprises the substitutions S193T+N195F of the mature polypeptide of SEQ ID NO: 6. In another aspect, the variant comprises T and Y as substitutions at positions 193 and 195, respectively. In another aspect, the variant comprising at least one, at least two, or at least three deletions in amino acid region of 181, 182, 183, or 184 and further comprises the substitutions S193T+N195Y of the mature polypeptide of SEQ ID NO: 6.

In another aspect, the variant of a parent alpha-amylase comprises a substitution at positions 195 and 198, using the numbering of SEQ ID NO: 6. In another aspect, the variant comprises a substitution at positions 195 and 198 with [F, W, Y, L, I, V, N or Q]. In another aspect, the variant comprises F and N as substitutions at positions 195 and 198, respectively. In another aspect, the variant comprises the substitutions N195F+Y198N wherein the parent is any of the mature polypeptides with SEQ ID NO: 6, 8, 10 or 12. In another aspect, the variant comprises Y and N as substitutions at positions 195 and 198, respectively. In another aspect, the variant comprises the substitutions N195Y+Y198N wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant of a parent alpha-amylase comprising at least one, at least two, or at least three deletions in amino acid region of 181, 182, 183, or 184 and further comprises a substitution at positions 195 and 198, using the numbering of SEQ ID NO: 6. In another aspect, the variant comprising at least one, at least two, or at least three deletions in amino acid region of 181, 182, 183, or 184 and further comprises substitutions at positions 195 and 198 with [F, W, Y, L, I, V, N or Q]. In another aspect, the variant comprises F and N as substitutions at positions 195 and 198, respectively. In another aspect, the variant comprising at least one, at least two, or at least three deletions in amino acid region of 181, 182, 183, or 184 and further comprises the substitutions N195F+Y198N wherein the parent is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12. In another aspect, the variant comprises Y and N as substitutions at positions 195 and 198, respectively. In another aspect, the variant comprising at least one, at least two, or at least three deletions in amino acid region of 181, 182, 183, or 184 and further comprises the substitutions N195Y+Y198N wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant of a parent alpha-amylase comprises a substitution at positions 195 and 206 using numbering according to SEQ ID NO: 6. In another aspect, the variant comprises a substitution at positions 195 and 206 with [F, W, Y, V, I, L, C, N, S, T, D, E or H]. In another aspect, the variant comprises F and L as substitutions at positions 195 and 206, respectively. In another aspect, the variant comprises the substitutions N195F+V206 [F, Y, L, H, or N] of the mature polypeptide of SEQ ID NO: 6 or 12. In another aspect, the variant comprises the substitutions N195F+I206[F, Y, L, or H] of the mature polypeptide of SEQ ID NO: 8 or 10. In another aspect, the variant comprises Y and L as substitutions at 195 and 206, respectively. In another aspect, the variant comprises the substitutions N195Y+V206 [F, Y, L, H, or N] of the mature polypeptide of SEQ ID NO: 6 or 12. In another aspect, the variant comprises the substitutions N195Y+I206 [F, Y, L, H, or N] of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195 and 206 using the numbering according to SEQ ID NO: 6. In another aspect, the variant comprising at least one, at least two, or at least three deletions in amino acid region of 181, 182, 183, or 184 and further comprises substitutions at positions 195 and 206 with [F, W, Y, V, I, L, C, N, S, T, D, E or H]. In another aspect, the variant comprises F and L as substitutions at positions 195 and 206, respectively. In another aspect, the variant comprising at least one, at least two, or at least three deletions in amino acid region of 181, 182, 183, or 184 and further comprises the substitutions N195F+V206[F or Y] of the mature polypeptide of SEQ ID NO: 6 or 12. In another aspect, the variant comprising at least one, at least two, or at least three deletions in amino acid region of 181, 182, 183, or 184 and further comprises the substitutions N195F+I206 [F, Y, L, H, or N] of the mature polypeptide of SEQ ID NO: 8 or 10. In another aspect, the variant comprises Y and L as substitutions at positions 195 and 206, respectively. In another aspect, the variant comprising at least one, at least two, or at least three deletions in amino acid region of 181, 182, 183, or 184 and further comprises the substitutions N195Y+V206 [F, Y, L, H, or N] of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206F of the mature polypeptide of SEQ ID NO: 8 or 10.

In another aspect, the variant of a parent alpha-amylase comprises substitutions at positions 195 and 210 using the numbering according to SEQ ID NO: 6. In another aspect, the variant comprises a substitution at positions 195 and 210 with [F, W, Y, V, I, L, C, N, S, T or H]. In another aspect, the variant comprises F and Y as substitutions at positions 195 and 210, respectively. In another aspect, the variant comprises the substitutions N195F+H210Y wherein the parent is any of the mature polypeptides with SEQ ID NO: 6, 8, 10 or 12. In another aspect, the variant comprises Y as substitution at positions 195 and 210. In another aspect, the variant comprises the substitutions N195Y+H210Y wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant of a parent alpha-amylase comprising at least one, at least two, or at least three deletions in amino acid region of 181, 182, 183, or 184 and further comprises substitutions at positions 195 and 210 using the numbering according to SEQ ID NO: 6. In another aspect, the variant comprising at least one, at least two, or at least three deletions in amino acid region of 181, 182, 183, or 184 and further comprises substitutions at positions 195 and 210 with [F, W, Y, V, I, L, C, N, S, T or H]. In another aspect, the variant comprises F and Y as substitutions at positions 195 and 210, respectively. In another aspect, the variant comprising at least one, at least two, or at least three deletions in amino acid region of 181, 182, 183, or 184 and further comprises the substitutions N195F+H210Y wherein the parent alpha-amylase is any of the mature polypeptides with SEQ ID NO: 6, 8, 10, 12, 18, or 22, preferably SEQ ID NO: 6, 8, 10 or 12. In another aspect, the variant comprises Y as substitution at positions corresponding to positions 195 and 210. In another aspect, the variant comprising at least one, at least two, or at least three deletions in amino acid region of 181, 182, 183, or 184 and further comprises the substitutions N195Y+H210Y wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant parent alpha-amylase comprises substitutions at positions corresponding to positions 198 and 206 using numbering according to SEQ ID NO: 6. In another aspect, the variant comprises substitutions at positions 198 and 206 with [N, Q, L, I, F, Y, C, N, S, T, D, E or H]. In another aspect, the variant comprises N and [For Y] as substitutions at positions 198 and 206, respectively. In another aspect, the variant comprises the substitutions Y198N+V206 [F, Y, L, H, or N] of the mature polypeptide of SEQ ID NO: 6 or 12. In another aspect, the variant comprises the substitutions Y198N+I206 [F, Y, L, H or N] of the mature polypeptide of SEQ ID NO: 8 or 10.

In another aspect, the variant parent alpha-amylase comprising at least one, at least two, or at least three deletions in amino acid region of 181, 182, 183, or 184 and further comprises substitutions at positions corresponding to positions 198 and 206 using numbering according to SEQ ID NO: 6. In another aspect, the variant comprising at least one, at least two, or at least three deletions in amino acid region of 181, 182, 183, or 184 and further comprises substitutions at positions 198 and 206 with [N, Q, L, I, F, Y, C, N, S, T, D, E or H]. In another aspect, the variant comprises N and [For Y] as substitutions at positions 198 and 206, respectively. In another aspect, the variant comprising at least one, at least two, or at least three deletions in amino acid region of 181, 182, 183, or 184 and further comprises the substitutions Y198N+V206 [F, Y, L, H, or N] of the mature polypeptide of SEQ ID NO: 6 or 12. In another aspect, the variant comprising at least one, at least two, or at least three deletions in amino acid region of 181, 182, 183, or 184 and further comprises the substitutions Y198N+I206 [F, Y, L, H or N] of the mature polypeptide of SEQ ID NO: 8 or 10.

In another aspect, the variant of a parent alpha-amylase comprises substitutions at positions 206 and 213, using the numbering according to SEQ ID NO: 6. In another aspect, the variant comprises a substitution at positions 206 and 213 with [D, E, L, I, V, F, Y, W, G, A, S, T or M]. In another aspect, the variant comprises [F or Y] and A as substitutions at positions 206 and 210, respectively. In another aspect, the variant comprises the substitutions V206F or Y+V213A of the mature polypeptide of SEQ ID NO: 6 or 12. In another aspect, the variant comprises the substitutions I206 [F, Y, L, H, or N]+V213A of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 206 and 213, using the numbering according to SEQ ID NO: 6.

In another aspect, the variant comprising at least one, at least two, or at least three deletions in amino acid region of 181, 182, 183, or 184 and further comprises substitutions at positions 206 and 213 with [D, E, L, I, V, F, Y, W, G, A, S, T or M]. In another aspect, the variant comprises [F or Y] and A as substitutions at positions 206 and 210, respectively. In another aspect, the variant comprising at least one, at least two, or at least three deletions in amino acid region of 181, 182, 183, or 184 and further comprises the substitutions V206 [F, Y, L, H, or N], V213A of the mature polypeptide of SEQ ID NO: 6 or 12. In another aspect, the variant comprising at least one, at least two, or at least three deletions in amino acid region of 181, 182, 183, or 184 and further comprises the substitutions I206 [F, Y, L, H, or N]+V213A of the mature polypeptide of SEQ ID NO: 8 or 10.

In another aspect, the variant of a parent alpha-amylase comprises substitutions at positions 195 and 243 using the numbering according to SEQ ID NO: 6. In another aspect, the variant comprises a substitution at positions 195 and 243 with [F, W, Y, L, I or V]. In another aspect, the variant comprises F as substitutions at positions 195 and 243, respectively. In another aspect, the variant comprises the substitutions N195F+Y243F, wherein the parent alpha-amylase is any of the mature polypeptides with SEQ ID NO: 6, 8, 10 or 12. In another aspect, the variant comprises Y and F as substitutions at positions 195 and 243, respectively. In another aspect, the variant comprises the substitutions N195Y+Y243F wherein the parent alpha-amylase is any of the mature polypeptides with SEQ ID NO: 6, 8, 10 or 12.

In another aspect, the variant of a parent alpha-amylase comprising at least one, at least two, or at least three deletions in amino acid region of 181, 182, 183, or 184 and further comprises substitutions at positions corresponding to positions 195 and 243. In another aspect, the variant comprising at least one, at least two, or at least three deletions in amino acid region of 181, 182, 183, or 184 and further comprises substitutions at positions 195 and 243 with [F, W, Y, L, I or V]. In another aspect, the variant comprises F as substitutions at positions 195 and 243, respectively. In another aspect, the variant comprising at least one, at least two, or at least three deletions in amino acid region of 181, 182, 183, or 184 and further comprises the substitutions N195F+Y243F wherein the parent alpha-amylase is any of the mature polypeptides with SEQ ID NO: 6, 8, 10 or 12. In another aspect, the variant comprises Y and F as substitutions at positions 195 and 243, respectively. In another aspect, the variant comprising at least one, at least two, or at least three deletions in amino acid region of 181, 182, 183, or 184 and further comprises the substitutions N195Y+Y243F wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12.

In another aspect, the variant of a parent alpha-amylase comprises substitutions at positions 206 and 243 using the numbering according to SEQ ID NO: 6. In another aspect, the variant comprises a substitution at positions 206 and 243 with [H, D, E, N, F, W, Y, L, I or V]. In another aspect, the variant comprises L and F as substitutions at positions 206 and 243, respectively. In another aspect, the variant comprises the substitutions V206 [F, Y, L, H, or N]+Y243F of the mature polypeptide of SEQ ID NO: 6 or 12. In another aspect, the variant comprises the substitutions V206 [F, Y, L, H, or N]+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 206 and 243 using the numbering according to SEQ ID NO: 6. In another aspect, the variant comprising at least one, at least two, or at least three deletions in amino acid region of 181, 182, 183, or 184 and further comprises substitutions at positions 206 and 243 with [H, D, E, N, F, W, Y, L, I or V]. In another aspect, the variant comprises L and F as substitutions at positions 206 and 243, respectively. In another aspect, the variant comprising at least one, at least two, or at least three deletions in amino acid region of 181, 182, 183, or 184 and further comprises the substitutions V206 [F, Y, L, H, or N]+Y243F of the mature polypeptide of SEQ ID NO: 6 or 12. In another aspect, the variant comprising at least one, at least two, or at least three deletions in amino acid region of 181, 182, 183, or 184 and further comprises the substitutions V206 [F, Y, L, H, or N]+Y243F of the mature polypeptide of SEQ ID NO: 8 or 10.

In another aspect, the variant of a parent alpha-amylase comprises substitutions at positions 193, 195, and 197 using the numbering according to SEQ ID NO: 6. In another aspect, the variant comprises a substitution at positions 193, 195, and 197 with [F, W, Y, L, I or V]. In another aspect, the variant comprises T and F as substitutions at positions corresponding to positions 193, 195, and 197, respectively. In another aspect, the variant comprises the substitutions S193T+N195F+N197F wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12. In another aspect, the variant comprises T, F and L as substitutions at positions 193, 195, and 197, respectively. In another aspect, the variant comprises the substitutions S193T+N195F+N197L wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12. In another aspect, the variant comprises T, Y and F as substitutions at positions corresponding to positions 193, 195, and 197, respectively. In another aspect, the variant comprises the substitutions S193T+N195Y+N197F wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12. In another aspect, the variant comprises T, Y and L as substitutions at positions corresponding to positions 193, 195, and 197, respectively. In another aspect, the variant comprises the substitutions S193T+N195Y+N197L wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, 20 or 22, preferably SEQ ID NO: 6, 8, 10 or 12.

In another aspect, the variant comprising at least one, at least two, or at least three deletions in amino acid region of 181, 182, 183, or 184 and further comprises substitutions at positions 193, 195, and 197 using the numbering according to SEQ ID NO: 6. In another aspect, the variant comprising at least one, at least two, or at least three deletions in amino acid region of 181, 182, 183, or 184 and further comprises substitutions at positions 193, 195, and 197 with [F, W, Y, L, I or V]. In another aspect, the variant comprises T and F as substitutions at positions 193, 195, and 197, respectively. In another aspect, the variant comprising at least one, at least two, or at least three deletions in amino acid region of 181, 182, 183, or 184 and further comprises the substitutions S193T+N195F+N197F wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12. In another aspect, the variant comprises T, F and L as substitutions at positions 193, 195, and 197, respectively. In another aspect, the variant comprising at least one, at least two, or at least three deletions in amino acid region of 181, 182, 183, or 184 and further comprises the substitutions S193T+N195F+N197L, wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO:14, 16 or 20, preferably SEQ ID NO: 6, 8, 10 or 12. In another aspect, the variant comprises T, Y and F as substitutions at positions 193, 195, and 197, respectively. In another aspect, the variant comprising at least one, at least two, or at least three deletions in amino acid region of 181, 182, 183, or 184 and further comprises the substitutions S193T+N195Y+N197F wherein the parent alpha-amylase is any of the mature polypeptides with SEQ ID NO: 6, 8, 10 or 12. In another aspect, the variant comprises T, Y and L as substitutions at positions 193, 195, and 197, respectively. In another aspect, the variant comprising at least one, at least two, or at least three deletions in amino acid region of 181, 182, 183, or 184 and further comprises the substitutions S193T+N195Y+N197L wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant of a parent alpha-amylase comprises substitutions at positions 195, 206 and 243 using the numbering according to SEQ ID NO: 6. In another aspect, the variant comprises substitutions at positions 195, 206 and 243 with [D, E, L, I, F, V, Y, C, N, S, T or H]. In another aspect, the variant comprises F, N and F as substitutions at positions 195, 206, and 243, respectively. In another aspect, the variant comprises the substitutions N195F+V206N+Y243F of the mature polypeptide of SEQ ID NO: 6 or 12. In another aspect, the variant comprises the substitutions N195F+I206N+Y243F of the mature polypeptide of SEQ ID NO: 8 or 10. In another aspect, the variant comprises Y, N and F as substitutions at positions 195, 206, and 243, respectively. In another aspect, the variant comprises the substitutions N195Y+V206N+Y243F of the mature polypeptide of SEQ ID NO: 6 or 12. In another aspect, the variant comprises the substitutions N195Y+I206N+Y243F of the mature polypeptide of SEQ ID NO: 8 or 10.

In another aspect, the variant of a parent alpha-amylase comprises substitutions at positions 195, 206 and 243 using the numbering according to SEQ ID NO: 6. In another aspect, the variant comprises substitutions at positions 195, 206 and 243 with [D, E, L, I, F, V, Y, C, N, S, T or H]. In another aspect, the variant comprises F, L and F as substitutions at positions 195, 206, and 243, respectively. In another aspect, the variant comprises the substitutions N195F+V206L+Y243F of the mature polypeptide of SEQ ID NO: 6 or 12. In another aspect, the variant comprises the substitutions N195F+I206L+Y243F of the mature polypeptide of SEQ ID NO: 8 or 10. In another aspect, the variant comprises Y, L and F as substitutions at positions 195, 206, and 243, respectively. In another aspect, the variant comprises the substitutions N195Y+V206L+Y243F of the mature polypeptide of SEQ ID NO: 6 or 12. In another aspect, the variant comprises the substitutions N195Y+I206L+Y243F of the mature polypeptide of SEQ ID NO: 8 or 10.

In another aspect, the variant of a parent alpha-amylase comprises substitutions at positions 195, 206 and 243 using the numbering according to SEQ ID NO 6. In another aspect, the variant comprises substitutions at positions 195, 206 and 243 with [D, E, L, I, F, V, Y, C, N, S, T or H]. In another aspect, the variant comprises F, N and F as substitutions at positions 195, 206, and 243, respectively. In another aspect, the variant comprises the substitutions N195F+V206N+Y243F of the mature polypeptide of SEQ ID NO: 6 or 12. In another aspect, the variant comprises the substitutions N195F+I206N+Y243F of the mature polypeptide of SEQ ID NO: 8 or 10. In another aspect, the variant comprises Y, N and F as substitutions at positions 195, 206, and 243, respectively. In another aspect, the variant comprises the substitutions N195Y+V206N+Y243F of the mature polypeptide of SEQ ID NO: 6 or 12. In another aspect, the variant comprises the substitutions N195Y+I206N+Y243F of the mature polypeptide of SEQ ID NO: 8 or 10.

In another aspect, the variant of a parent alpha-amylase comprises substitutions at positions 195, 206 and 243 using the numbering according to SEQ ID NO: 6. In another aspect, the variant comprises substitutions at positions 195, 206 and 243 with [D, E, L, I, F, V, Y, C, N, S, T or H]. In another aspect, the variant comprises F, H and F as substitutions at positions 195, 206, and 243, respectively. In another aspect, the variant comprises the substitutions N195F+V206H+Y243F of the mature polypeptide of SEQ ID NO: 6 or 12. In another aspect, the variant comprises the substitutions N195F+I206H+Y243F of the mature polypeptide of SEQ ID NO: 8 or 10. In another aspect, the variant comprises Y, H and F as substitutions at positions 195, 206, and 243, respectively. In another aspect, the variant comprises the substitutions N195Y+V206H+Y243F of the mature polypeptide of SEQ ID NO: 6 or 12. In another aspect, the variant comprises the substitutions N195Y+I206H+Y243F of the mature polypeptide of SEQ ID NO: 8 or 10.

In another aspect, the variant of a parent alpha-amylase comprises substitutions at positions 195, 206 and 243 using the numbering according to SEQ ID NO: 6. In another aspect, the variant comprises substitutions at positions 195, 206 and 243 with [D, E, L, I, F, V, Y, C, N, S, T or H]. In another aspect, the variant comprises F, F and F as substitutions at positions 195, 206, and 243, respectively. In another aspect, the variant comprises the substitutions N195F+V206F+Y243F of the mature polypeptide of SEQ ID NO: 6 or 12. In another aspect, the variant comprises the substitutions N195F+I206F+Y243F of the mature polypeptide of SEQ ID NO: 8 or 10. In another aspect, the variant comprises Y, F and F as substitutions at positions 195, 206, and 243, respectively. In another aspect, the variant comprises the substitutions N195Y+V206F+Y243F of the mature polypeptide of SEQ ID NO: 6 or 12. In another aspect, the variant comprises the substitutions N195Y+I206F+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195, 206 and 243, using the numbering according to SEQ ID NO: 6. In another aspect, the variant comprising at least one, at least two, or at least three deletions in amino acid region of 181, 182, 183, or 184 and further comprises substitutions at positions 195, 206 and 243 with [D, E, L, I, F, V, Y, C, N, S, T or H]. In another aspect, the variant comprises F, Y and F as substitutions at positions 195, 206, and 243, respectively. In another aspect, the variant comprising at least one, at least two, or at least three deletions in amino acid region of 181, 182, 183, or 184 and further comprises the substitutions N195F+V206Y+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195F+I206Y+Y243F of the mature polypeptide of SEQ ID NO: 8 or 10. In another aspect, the variant comprises Y, Y and F as substitutions at positions 195, 206, and 243, respectively. In another aspect, the variant comprising at least one, at least two, or at least three deletions in amino acid region of 181, 182, 183, or 184 and further comprises the substitutions N195Y+V206Y+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206Y+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195, 206 and 243, using the numbering according to SEQ ID NO: 6. In another aspect, the variant comprising at least one, at least two, or at least three deletions in amino acid region of 181, 182, 183, or 184 and further comprises substitutions at positions 195, 206 and 243 with [D, E, L, I, F, V, Y, C, N, S, T or H]. In another aspect, the variant comprises F, L and F as substitutions at positions 195, 206, and 243, respectively. In another aspect, the variant comprising at least one, at least two, or at least three deletions in amino acid region of 181, 182, 183, or 184 and further comprises the substitutions N195F+V206L+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195F+I206L+Y243F of the mature polypeptide of SEQ ID NO: 8 or 10. In another aspect, the variant comprises Y, L and F as substitutions at positions 195, 206, and 243, respectively. In another aspect, the variant comprising at least one, at least two, or at least three deletions in amino acid region of 181, 182, 183, or 184 and further comprises the substitutions N195Y+V206L+

Y243F of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206L+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195, 206 and 243, using the numbering according to SEQ ID NO: 6. In another aspect, the variant comprising at least one, at least two, or at least three deletions in amino acid region of 181, 182, 183, or 184 and further comprises substitutions at positions 195, 206 and 243 with [D, E, L, I, F, V, Y, C, N, S, T or H]. In another aspect, the variant comprises F, N and F as substitutions at positions 195, 206, and 243, respectively. In another aspect, the variant comprising at least one, at least two, or at least three deletions in amino acid region of 181, 182, 183, or 184 and further comprises the substitutions N195F+V206N+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195F+I206N+Y243F of the mature polypeptide of SEQ ID NO: 8 or 10. In another aspect, the variant comprises Y, N and F as substitutions at positions 195, 206, and 243, respectively. In another aspect, the variant comprising at least one, at least two, or at least three deletions in amino acid region of 181, 182, 183, or 184 and further comprises the substitutions N195Y+V206N+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206N+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195, 206 and 243, using the numbering according to SEQ ID NO: 6. In another aspect, the variant comprising at least one, at least two, or at least three deletions in amino acid region of 181, 182, 183, or 184 and further comprises substitutions at positions 195, 206 and 243 with [D, E, L, I, F, V, Y, C, N, S, T or H]. In another aspect, the variant comprises F, H and F as substitutions at positions 195, 206, and 243, respectively. In another aspect, the variant comprising at least one, at least two, or at least three deletions in amino acid region of 181, 182, 183, or 184 and further comprises the substitutions N195F+V206H+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195F+I206H+Y243F of the mature polypeptide of SEQ ID NO: 8 or 10. In another aspect, the variant comprises Y, H and F as substitutions at positions 195, 206, and 243, respectively. In another aspect, the variant comprising at least one, at least two, or at least three deletions in amino acid region of 181, 182, 183, or 184 and further comprises the substitutions N195Y+V206H+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206H+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195, 206 and 243, using the numbering according to SEQ ID NO: 6. In another aspect, the variant comprising at least one, at least two, or at least three deletions in amino acid region of 181, 182, 183, or 184 and further comprises substitutions at positions 195, 206 and 243 with [D, E, L, I, F, V, Y, C, N, S, T or H]. In another aspect, the variant comprises F, F and F as substitutions at positions 195, 206, and 243, respectively. In another aspect, the variant comprising at least one, at least two, or at least three deletions in amino acid region of 181, 182, 183, or 184 and further comprises the substitutions N195F+V206F+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195F+I206F+Y243F of the mature polypeptide of SEQ ID NO: 8 or 10. In another aspect, the variant comprises Y, F and F as substitutions at positions 195, 206, and 243, respectively. In another aspect, the variant comprising at least one, at least two, or at least three deletions in amino acid region of 181, 182, 183, or 184 and further comprises the substitutions N195Y+V206F+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206F+Y243F of the mature polypeptide of SEQ ID NO: 8 or 10.

In one aspect of the invention the variant comprising at least one, at least two, or at least three deletions in amino acid region of 181, 182, 183, or 184 and one or more of the following substitutions N195 [F or Y], N197 [F or L], Y198N, Y200F, Y203F, I206 [H,L,N,F, or Y], H210Y, E212 [V or G], V213A and a substitution at one or more positions M116T, Q129L, G133E, E134Y, K142R, P146S, G147E, G149R, N151R, Y152H, Q169E, N174R, G186R, Y243F, S244Q, G303V, R320N, R359I, N418D, A447V of the mature polypeptide sequence of SEQ ID NO: 10 or an amino acid sequence having a degree of identity of at least 60%, preferred at least 65%, preferred at least 70%, preferred at least 75% preferred at least 80%, preferred at least 81%, preferred at least 82%, preferred at least 83%, preferred at least 84% preferred at least 85%, preferred at least 86%, preferred at least 87%, preferred at least 88%, preferred at least 89%, especially preferred at least 90%, especially preferred at least 91%, especially preferred at least 92%, especially preferred at least 93%, especially preferred at least 94%, even especially more preferred at least 95% homology, more preferred at least 96%, more preferred at least 97%, more preferred at least 98%, more preferred at least 99% to the amino acid sequence with SEQ ID NO: 10.

In another aspect of the invention the variant comprising at least one, at least two, or at least three deletions in amino acid region of 181, 182, 183, or 184 and one or more of the following substitutions N195 [F or Y], N197 [F or L], Y198N, Y200F, Y203F, I206 [F, Y, L, H, or N], H210Y, E212 [V or G], V213A and a substitution at one or more positions M116T, Q129L, G133E, E134Y, P146S, G147E, G149R, T151R, Y152H, Q169E, N174R, A186R, Y243F, S244Q, G303V, R320N, R359I, N418D, A447V of the mature polypeptide sequence of SEQ ID NO: 8 or an amino acid sequence having a degree of identity of at least 60%, preferred at least 65%, preferred at least 70%, preferred at least 75% preferred at least 80%, preferred at least 81%, preferred at least 82%, preferred at least 83%, preferred at least 84% preferred at least 85%, preferred at least 86%, preferred at least 87%, preferred at least 88%, preferred at least 89%, especially preferred at least 90%, especially preferred at least 91%, especially preferred at least 92%, especially preferred at least 93%, especially preferred at least 94%, even especially more preferred at least 95% homology, more preferred at least 96%, more preferred at least 97%, more preferred at least 98%, more preferred at least 99% to the amino acid sequence with SEQ ID NO: 8.

In one aspect of the invention the variant comprising at least one, at least two, or at least three deletions in amino acid region of 181, 182, 183, or 184 and one or more of the following substitutions N195 [F or Y], N197 [F or L], Y198N, Y200F, Y203F, V206 [F, Y, L, H, or N], H210Y, E212 [V or G], V213A, or Y243F and a substitution at one or more positions I116T, Q129L, G133E, E134Y, K142R, P146S, G147E, G149R, N151R, Y152H, Q169E, Q174R, A186R, S244Q, G303V, K320N, R359I, N418D, A447V of the mature polypeptide sequence of SEQ ID NO: 6 or an amino acid sequence having a degree of identity of at least 60%, preferred at least 65%, preferred at least 70%, preferred at least 75% preferred at least 80%, preferred at least 81%, preferred at least 82%, preferred at least 83%, preferred at least 84% preferred at least 85%, preferred at least 86%, preferred at least 87%, preferred at least 88%, preferred at least 89%, especially preferred at least 90%, especially preferred at least 91%, especially preferred at least 92%, especially preferred at least 93%, especially preferred at least 94%, even especially more preferred at least 95% homology, more preferred at least 96%, more preferred at least 97%, more preferred at least 98%, more preferred at least 99% to the amino acid sequence with SEQ ID NO: 6.

In one aspect of the invention the variant comprising at least one, at least two, or at least three deletions in amino acid region of 181, 182, 183, or 184 and one or more of the following substitutions N195 [F or Y], N197 [F or L], Y198N, Y200F, Y203F, V206 [F, Y, L, H, or N], H210Y, E212 [V or G], V213A or Y243F and a substitution at one or more positions I116T, Q129L, G133E, E134Y, K142R, P146S, G147E, G149R, N151R, Y152H, Q169E, Q174R, A186R, S244Q, G303V, K320N, R359I, N418D, A447V of the mature polypeptide sequence of SEQ ID NO: 12 or an amino acid sequence having a degree of identity of at least 60%, preferred at least 65%, preferred at least 70%, preferred at least 75% preferred at least 80%, preferred at least 81%, preferred at least 82%, preferred at least 83%, preferred at least 84% preferred at least 85%, preferred at least 86%, preferred at least 87%, preferred at least 88%, preferred at least 89%, especially preferred at least 90%, especially preferred at least 91%, especially preferred at least 92%, especially preferred at least 93%, especially preferred at least 94%, even especially more preferred at least 95% homology, more preferred at least 96%, more preferred at least 97%, more preferred at least 98%, more preferred at least 99% to the amino acid sequence with SEQ ID NO: 12.

Thus one aspect of the invention concern variants of a parent alpha-amylase comprising an alteration at one or more positions selected from the group consisting of 195, 197, 198, 200, 203, 206, 210, 212, 213 and 243 and further comprising an alteration at one or more positions selected from the group consisting of 116, 118, 129, 133, 134, 142, 146, 147, 149, 151, 152, 169, 174, 186, 235, 244, 303, 320, 359, 418, 431, 434, 447 and 458 wherein (a) the alteration(s) are independently
  (i) an insertion of an amino acid immediately downstream of the position,
  (ii) a deletion of the amino acid which occupies the position, and/or
  (iii) a substitution of the amino acid which occupies the position,
(b) the variant has alpha-amylase activity; and
(c) each position corresponds to a position of the amino acid sequence of the enzyme having the amino acid sequence of SEQ ID NO:6.

Thus one aspect of the invention concern variants of a parent alpha-amylase comprising at least one, at least two, or at least three deletions in amino acid region of 181, 182, 183, or 184 and an alteration at one or more positions selected from the group consisting of 195, 197, 198, 200, 203, 206, 210, 212, 213, 243 and further comprising an alteration at one or more positions selected from the group consisting of 116, 118, 129, 133, 134, 142, 146, 147, 149, 151, 152, 169, 174, 186, 235, 244, 303, 320, 339, 359, 418, 431, 434, 447 and 458 wherein (a) the alteration(s) are independently
  (i) an insertion of an amino acid immediately downstream and adjacent of the position,
  (ii) a deletion of the amino acid which occupies the position, and/or
  (iii) a substitution of the amino acid which occupies the position,
(b) the variant has alpha-amylase activity; and
(c) each position corresponds to a position of the amino acid sequence of the enzyme having the amino acid sequence of SEQ ID NO:6.

Preferably the variant comprises an amino acid sequence which has a degree of identity of at least 70%, preferably at least 75%, more preferably at least 80%, more preferably at least 85%, even more preferably at least 90%, most preferably at least 95%, and even most preferably at least about 97% to the amino acid sequence of one of SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 14, 16, 18, 22, or 20.

Preferably, the variants comprising alterations at one or more of the above identified positions have an increased stability in compositions comprising a chelating agent such as industrial compositions, e.g., detergent, preferably in liquid detergent as compared to the parent alpha-amylase.

The inventors have found that these variants have an improved stability relative to the parent alpha-amylase in compositions comprising a chelating agent wherein said chelating agent at a concentration below 10 mM is capable of reducing the concentration of free calcium ions from 2.0 mM to 0.10 mM, at 21° C. and pH 8.0, as described under "Materials and Methods".

Thus, another aspect the invention relates to a method for preparing a polypeptide comprising;

(a) providing an amino acid sequence of a parent polypeptide having amylase activity;
(b) selecting one or more amino acid which occupies one or more position corresponding to positions 195, 197, 198, 200, 203, 206, 210, 212, 213, 243, and further selecting one or more position corresponding to positions 116, 118, 129, 133, 134, 142, 146, 147, 149, 151, 152, 169, 174, 186, 235, 244, 303, 320, 339, 359, 418, 431, 434, 447, 458 of the mature polypeptide of SEQ ID NO: 6;

(c) modifying the sequence by substituting or deleting the selected amino acid residue or inserting one or more amino acid residues downstream and adjacent to the selected amino acid residue;

(d) producing a variant polypeptide having the modified sequence;

(e) testing the variant polypeptide for amylase activity and stability; and (f) selecting a variant polypeptide having amylase activity and increased stability relative to the parent polypeptide in the presence of a chelating agent wherein said chelating agent at a concentration below 10 mM is capable of reducing the concentration of free calcium ions from 2.0 mM to 0.10 mM at 21° C. and pH 8.0.

Preferably the variants comprises alterations at three positions, more preferred four positions even more preferred five positions and most preferred six positions, in a particularly preferred embodiment the variant comprising at least one, at least two, or at least three deletions in amino acid region of 181, 182, 183, or 184 and further one or more substitution at one or more positions corresponding to positions in the parent alpha-amylase selected from the group consisting of 193, 195, 197, 198, 200, 203, 206, 210, 212, 213, 243 (using numbering according to SEQ ID NO: 6).

Thus a preferred aspect relates to a variant of a parent alpha-amylase comprising at least one, at least two, or at least three deletions in amino acid region of 181, 182, 183, or 184 an alteration at one or more positions selected from the group consisting of 195, 197, 198, 200, 203, 206, 210, 212, 213, 243 and further comprising an alteration at one or more positions selected from the group consisting of 116, 118, 129, 133, 134, 142, 146, 147, 149, 151, 152, 169, 174, 186, 235, 244, 303, 320, 339, 359, 418, 413, 434, 447, 458 wherein (a) the alteration(s) are independently (i) an insertion of an amino acid immediately downstream and adjacent of the position, (ii) a deletion of the amino acid which occupies the position, and/or (iii) a substitution of the amino acid which occupies the position, (b) the variant has alpha-amylase activity; and (c) each position corresponds to a position of the amino acid sequence of the enzyme having the amino acid sequence of SEQ ID NO:6.

In a preferred embodiment the variant alpha-amylase have one or more (several) amino acid deletions and/or substitutions and/or insertions. In a particularly preferred embodiment the variant alpha-amylases include an alpha-amylase, which has the amino acid sequence shown in SEQ ID NO: 6 herein and which further comprise the following alteration: D183*+G184* (deletion at position 183 and 184), this variant show good performance in detergents and have improved stability in the presence of chelating agents.

In a preferred embodiment the variant alpha-amylase comprises SP707 (SEQ ID NO: 8) including any of SP707+R181* G182*, SP707+G182* H183*, SP707+H183* G184*.

In another preferred embodiment the variant alpha-amylase comprises SP722 (SEQ ID NO: 6) including any of SP722+R181* G182*, SP722+G182* D183*, SP722+D183* G184*.

In yet another preferred embodiment the variant alpha-amylase comprises AA560 (SEQ ID NO: 10) including any of AA560+R181* G182*, AA560+G182* D183*, AA560+D183* G184*.

In another preferred embodiment the parent alpha-amylase comprises SP690 (SEQ ID NO: 12) including any of SP690+R181* G182*; SP690+G182* T183*; SP690+T183* G184*.

"SP722+R181* G182* means the *Bacillus* spp. alpha-amylase SP722 has been mutated by deletions in positions R181 and G182 wherein the numbering corresponds to SEQ. ID NO: 6.

Thus, in one aspect of the invention the variant alpha-amylase comprises any one of the following: SP722, SP690, SP707 or AA560 including any of:

SP722+R181*G182*, SP722+G182*+D183*, SP722+D183*+G184*; SP722+R181*G182* N195F; SP722+G182* D183* N195F; SP722+D183* G184* N195F; SP722+R181*G182* M202L; SP722+G182* D183* M202L; SP722+D183* G184* M202L; SP722+R181* G182* N195F M202L; SP722+G182 D183* N195F M202L; SP722+D183* G184* N195F M202L; SP722+D183*G184* N195F V206L Y243F; SP722+D183* G184* N195F V206Y Y243F SP722+D183* G184* N195F V206F Y243F; SP722+R181* G182* R181Q; SP722+G182* D183* R181Q; SP722+D183* G184* R181Q; SP722+R181* G182* L118K N195F H458K; SP722+G182* D183* L118K N195F H458K; SP722+D183* G184* L118K N195F H458K; SP722+D183* G184* G133E G149R N195Y Y203F V206L.

AA560+R181* G182*, AA560+G182* D183*, AA560+D183* G184*; AA560+R181* G182* N195F; AA560+G182* D183* N195F; AA560+D183* G184* N195F; AA560+D183* G184* I206Y; AA560+D183* G184* Y243F; AA560+D183* G184* I206L Y243F; AA560+D183* G184* N195F I206L; AA560+D183* G184* N195F Y243F; AA560+D183* G184* N195F I206L, Y243F; AA560+D183* G184* N195F I206Y Y243F; AA560+D183* G184* N195F I206F; AA560+R181* G182* M202L; AA560+G182* D183* M202L; AA560+D183* G184* M202L; AA560+R181* G182* N195F M202L; AA560+G182* D183* N195F M202L; AA560+D183* G184* N195F M202L; AA560+R181* G182* R118K N195F R320K T458K; AA560+G182* D183* R118K N195F R320K T458K; AA560+D183* G184* R118K N195F R320K T458K; AA560+D183* G184* R118K N195F I206L R320K R458K; AA560+D183* G184* R118K N195F I206Y R320K R458K; AA560+D183* G184* R118K N195F Y243F R320K R458K; AA560+D183* G184* R118K N195F I206L Y243F R320K R458K.

SP707+R181* G182*, SP707+G182* H183*, SP707+H183* G184*; SP707+R181* G182* N195F; SP707+G182* H183* N195F; SP707+H183* G184* N195F I206L, Y243F; SP707+H183* G184* N195F I206Y Y243F; SP707+H183* G184* N195F I206F Y243F; SP707+H183* G184* N195F; SP707+R181* G182* M202L; SP707+G182* H183* M202L; SP707+D183* G184* M202L; SP707+R181* G182* N195F M202L; SP707+G182* H183* N195F M202L; SP707+H183* G184* N195F M202L; SP707+R181* G182* R181Q; SP707+G182* H183* R181Q; SP707+H183* G184* R181Q; SP707+R181* G182* R118K N195F R320K R458K; SP707+G182* H183* R118K N195F R320K R458K; SP707+H183* G184* R118K N195F R320K R458K;

SP690+R181* G182*, SP690+G182* T183*, SP690+T183* G184*; SP690+R181* G182* N195F; SP690+G182* T183* N195F; SP690+T183* G184* N195F; SP690+T183* G184* N195F V206L, Y243F; SP690+T183* G184* N195F V206Y Y243F; SP690+T183*

G184* N195F V206F Y243F SP690+R181* G182* M202L; SP690+G182* T183* M202L; SP690+T183* G184* M202L; SP690+R181* G182* N195F M202L; SP690+G182* T183* N195F M202L; SP690+T183* G184* N195F M202L; SP690+R181* G182* R118K N195F R320K R458K; SP690+G182* T183* R118K N195F R320K R458K; SP690+T183* G184* R118K N195F R320K R458K. "SP722+R181* G182* N195F" means the *Bacillus* spp. alpha-amylase SP722 has been mutated as follows: deletions in positions R181 and G182 and a substitution from Asn (N) to Phe (F) in position 195 wherein the numbering corresponds to SEQ. ID NO: 6 (Counting as if the deleted positions are still present, i.e., the numbering does not shift down by two when deleting two positions).

In a particular preferred embodiment of the invention the alterations are selected from the following substitutions:

X193A,C,E,F,G,H,I,K,L,M,N,P,Q,R,S,T,V,W,X,Y, preferably S193T;

X195A,C,E,F,G,H,I,K,L,M,N,P,Q,R,S,T,V,W,X,Y, preferably N195 [For Y];

X197A,C,D,E,F,G,H,I,K,L,N,P,Q,R,S,T,V,W,X,Y, preferably N197 [F or L];

X198A,C,E,F,G,H,I,K,L,M,N,P,Q,R,S,T,V,W,X,Y, preferably Y198N;

X200A,C,D,E,F,G,H,I,L,M,N,P,Q,R,S,T,V,W,X,Y, preferably Y200F;

X203A,C,D,E,F,G,H,I,K,L,M,N,P,Q,R,T,V,W,X,Y, preferably Y203F.

X206A,C,D,E,F,G,H,I,K,L,N,P,Q,R,S,T,V,W,X,Y, preferably V206 [F, Y, L, H, or N];

X210A,C,E,F,G,H,I,K,L,M,N,P,Q,R,S,T,V,W,X,Y, preferably H210Y;

X212A,C,D,E,F,G,H,I,L,M,N,P,Q,R,S,T,V,W,X,Y, preferably E212 [V or G]; and

X213A,C,D,E,F,G,H,I,K,L,M,N,P,Q,R,T,V,W,X,Y, preferably V213A.

X243A,C,D,E,F,G,I,K,L,M,N,P,Q,R,S,T,V,W,Y, preferably Y243F

In another preferred embodiment the variants comprises alterations at three positions, more preferred four positions, more preferred five positions and more preferred six positions, in a particularly preferred embodiment the variant comprising at least one, at least two, or at least three deletions in amino acid region of 181, 182, 183, or 184 and further an altering at one or more positions corresponding to positions selected from the group consisting of 193, 195, 197, 198, 200, 203, 206, 210, 212, 213, 243 and an altering at one or more positions corresponding to positions selected from the group consisting of 116, 129, 133, 142, 146, 147, 149, 151, 152, 169, 174, 186, 244, 303, 320, 359, 418, 447 (using numbering according to SEQ ID NO: 6).

Thus, in a particular preferred embodiment of the invention the alterations are selected from the following substitutions:

X116A,C,D,E,F,G,H,I,K,L,M,P,Q,R,S,T,V,W,Y, preferably N116T

X118A,C,D,E,F,G,H,I,K,L,M,P,Q,R,S,T,V,W,Y, preferably R118K

X129A,C,D,E,F,G,H,I,K,L,M,N,P,Q,S,T,V,W,Y, preferably Q129L

X133A,C,D,E,F,H,I,K,L,M,N,P,Q,R,S,T,V,W,Y, preferably G133E

X134A,C,D,E,F,G,H,I,L,M,N,P,Q,R,S,T,V,W,Y, preferably D134Y

X142A,C,D,E,F,H,I,K,L,M,N,P,Q,R,S,T,V,W,Y, preferably K142R

X146A,C,E,F,G,H,I,K,L,M,N,P,Q,R,S,T,V,W,Y, preferably P146S

X147A,C,D,E,F,G,H,I,K,L,M,N,P,Q,R,S,T,W,Y, preferably G147E

X149A,C,D,E,F,G,I,K,L,M,N,P,Q,R,S,T,V,W,Y, preferably G149R

X151A,C,D,E,F,G,H,I,K,L,M,P,Q,R,S,T,V,W,Y, preferably T151R

X152A,C,D,E,F,G,H,I,K,L,M,P,Q,R,S,T,V,W,Y, preferably Y152H

X169A,C,E,F,G,H,I,K,L,M,N,P,Q,R,S,T,V,W,Y, preferably Q169E

X174C,D,E,F,G,H,I,K,L,M,N,P,Q,R,S,T,V,W,Y, preferably Q174R

X186A,C,D,E,F,G,H,I,K,L,M,N,P,Q,R,S,T,W,Y, preferably A186R

X235A,C,D,E,F,G,H,I,K,L,M,P,Q,R,S,T,V,W,Y, preferably 1235N

X244A,C,D,E,F,G,I,K,L,M,N,P,Q,R,S,T,V,W,Y, preferably S244Q

X303A,C,D,E,F,G,H,I,K,L,M,P,Q,R,S,T,V,W,Y, preferably G303V

X320A,C,E,F,G,H,I,K,L,M,N,P,Q,R,S,T,V,W,Y, preferably K320N

X339A,C,D,E,F,G,H,I,K,L,M,P,Q,R,S,T,V,W,Y, preferably S339P

X359C,D,E,F,G,H,I,K,L,M,N,P,Q,R,S,T,V,W,Y, preferably R359I

X418A,C,D,E,F,G,H,I,K,L,M,P,Q,R,S,T,V,W,Y, preferably N418D

X431A,C,D,E,F,G,H,I,K,L,M,P,Q,R,S,T,V,W,Y, preferably S431T

X434A,C,D,E,F,G,H,I,K,L,M,P,Q,R,S,T,V,W,Y, preferably P434T

X447A,C,E,F,G,H,I,K,L,M,N,P,Q,R,S,T,V,W,Y, preferably A447V

X458A,C,D,E,F,G,H,I,K,L,M,P,Q,R,S,T,V,W,Y, preferably R458K

In a particular preferred embodiment, the variant further comprising at least one, at least two, or at least three deletions in amino acid region of 181, 182, 183, or 184.

In a preferred embodiment, the number of amino acid substitutions in the variants of the present invention is preferably 17 substitutions, more preferably 16 substitutions, more preferably 15 substitutions, more preferably 14 substitutions, more preferably 13 substitutions, more preferably 12 substitutions, more preferably 11 substitutions, more preferably 10 substitutions, more preferably 9 substitutions, more preferably 8 substitutions, more preferably 7 substitutions, more preferably 6 substitutions, more preferably 5 substitutions, more preferably 4 substitutions, even more preferably 3 substitutions, and most preferably 2 substitutions. In another preferred embodiment, the number of amino acid substitutions in the variants of the present invention consists of preferably 17 substitutions, more preferably 16 substitutions, more preferably 15 substitutions, more preferably 14 substitutions, more preferably 13 substitutions, more preferably 12 substitutions, more preferably 11 substitutions, more preferably 10 substitutions, more preferably 9 substitutions, more preferably 8 substitutions, more preferably 7 substitutions, more preferably 6 substitutions, more preferably 5 substitutions, more preferably 4 substitutions, even more preferably 3 substitutions, and most preferably 2 substitution.

In particular preferred embodiment the variants according to the present invention comprises a combination of different alterations. Thus in an preferred embodiment the variant according to the present invention comprising at least one, at least two, or at least three deletions in amino acid region of 181, 182, 183, or 184, preferably deletion at position 183 and 184 and further comprises one of the following combinations of alterations substitutions at positions 186 and 195; substitutions at positions 174 and 212; substitutions at positions 206 and 212; substitutions at positions 206, 212 and 304; substitutions at positions 206, 212, 304 and 447; substitutions at positions 116 and 133; substitutions at positions 235 and 339; substitutions at positions 193 and 206; substitutions at positions 116, 133 and 142; substitutions at positions 116, 133, 142 and 198; substitutions at positions 116, 133, 142, 198 and 206; substitutions at positions 133 and 195; substitutions at positions 133, 195 and 198; substitutions at positions 133, 195, 198 and 200; substitutions at positions 116 and 195; substitutions at positions 116, 195 and 198; substitutions at positions 142 and 146; substitutions at positions 142, 146 and 149; substitutions at positions 142, 146, 149 and 195; substitutions at positions 142, 146, 149, 195 and 198; substitutions at positions 142, 146, 149, 195, 198 and 206; substitutions at positions 151 and 210; substitutions at positions 151, 210 and 320; substitutions at positions 186, 195, 212 and 213; substitutions at positions 151, 210, 320 and 359; substitutions at positions 151, 210, 320, 359 and 418; substitutions at positions 147 and 149; substitutions at positions 147, 149 and 169; substitutions at positions 147, 149, 169 and 198; substitutions at positions 147, 149, 169, 198 and 203; substitutions at positions 147, 149, 169, 198, 203 and 206; substitutions at positions 133 and 149; substitutions at positions 133, 149 and 195; substitutions at positions 133, 149, 195 and 198; substitutions at positions 133, 149, 195, 198 and 203; substitutions at positions 147 and 152; substitutions at positions 147, 152 and 169; substitutions at positions 147, 152, 169 and 198; substitutions at positions 147, 152, 169, 198 and 206; substitutions at positions 195 and 206; substitutions at positions 195 and 243; substitutions at positions 195 and 210; substitutions at positions 206 and 210; substitutions at positions 186 and 195; substitutions at positions 195 and 206; substitutions at positions 195, 206 and 243; substitutions at positions 206 and 243; substitutions at positions 133 and 149; substitutions at positions 133, 149 and 198; substitutions at positions 133, 149, 198 and 206; substitutions at positions 116 and 133; substitutions at positions 116, 133 and 147; substitutions at positions 116, 133, 147 and 152; substitutions at positions 116, 133, 147, 152 and 198; substitutions at positions 116, 133, 147, 152, 198 and 203; substitutions at positions 116, 133, 147, 152, 198, 203 and 206; substitutions at positions 147 and 149; substitutions at positions 147, 149 and 195; substitutions at positions 147, 149, 195 and 198; substitutions at positions 147, 149, 195, 198 and 206; substitutions at positions 133 and 142; substitutions at positions 133, 142 and 195; substitutions at positions 133, 142, 195 and 198; substitutions at positions 133 and 149; substitutions at positions 133, 149 and 152; substitutions at positions 133, 149, 152 and 195; substitutions at positions 133, 149, 152, 195 and 198; substitutions at positions 133, 149, 152, 195, 198 and 206; substitutions at positions 116 and 129; substitutions at positions 116, 129 and 142; substitutions at positions 116, 129, 142 and 195; substitutions at positions 116, 129, 142, 195 and 198; substitutions at positions 116, 129, 142, 195, 198 and 203; substitutions at positions 116, 129, 142, 195, 198, 203 and 206; substitutions at positions 133 and 149; substitutions at positions 133, 149 and 152; substitutions at positions 133, 149, 152 and 195; substitutions at positions 133, 149, 152, 195 and 198; substitutions at positions 133, 149, 152, 195, 198 and 203; substitutions at positions 133, 149, 152, 195, 198, 203 and 206; substitutions at positions 116 and 133; substitutions at positions 116, 133 and 149; substitutions at positions 116, 133, 149 and 198; substitutions at positions 116, 133, 149, 198 and 203; substitutions at positions 116, 133, 149, 198, 203 and 206; substitutions at positions 195 and 198; substitutions at positions 195, 198 and 203; substitutions at positions 195, 198, 203 and 206; substitutions at positions 133, 149, 195, 203, and 206.

In another particularly preferred embodiment, the variants according to the present invention comprises a combination of different alterations. Thus in an preferred embodiment the variant according to the present invention comprising at least one, at least two, or at least three deletions in amino acid region of 181, 182, 183, or 184, preferably deletion at position 183 and 184 and further comprises one of the following combinations of alterations substitutions at positions 186 with [R, T, K, H, E, D, Q, or N] and 195 with [F, W, Y, L, I, or oV]; substitutions at positions 174 with [R, K, H, E, D, Q, or N] and 212 with [F, W, Y, L, I, or V]; substitutions at positions 206 with [D, E, F, W, Y, L, I, V, N, Q, or H] and 212 with [F, W, Y, L, I, or V]; substitutions at positions 206 with [F, W, Y, L, I, V, N, Q, or H], 212 with [F, W, Y, L, I, or V] and 304 with [F, W, Y, L, I, or V]; substitutions at positions 206 with [F, W, Y, L, I, V, N, Q, or H], 212 with [F, W, Y, L, I, or V], 304 with [F, W, Y, L, I, or V] and 447 with [F, W, Y, L, I, or V]; substitutions at positions 116 with [G, A, S, T, or M] and 133 with [E or D]; substitutions at positions 235 with [N or L] and 339 with [P]; substitutions at positions 193 with [G, A, T or M] and 206 with [F, W, Y, L, I, V, N, Q, or H]; substitutions at positions 116 with [G, A, S, T, or M], 133 with [E or D] and 142 with [R, K, H, Q, or N]; substitutions at positions 116 with [G, A, S, T, or M], 133 with [E or D], 142 with [R, K, H, Q, or N] and 198 with [Q or N]; substitutions at positions 116 with [G, A, S, T, or M], 133 with [E or D], 142 with [R, K, H, Q, or N], 198 with [Q or N] with [Q or N] and 206 with [F, W, Y, L, I, V, N, Q, or H]; substitutions at positions 133 with [E or D] and 195 with [F, W, Y, L, I, or V]; substitutions at positions 133 with [E or D], 195 with [F, W, Y, L, I, or V] and 198 with [Q or N]; substitutions at positions 186 with [R, T, K, H, E, D, Q, or N], 195, with [F, W, Y, L, I, or V], 212 with [F, W, Y, L, I, or V] and 213; with [A]; substitutions at positions 133 with [E or D], 195 with [F, W, Y, L, I, or V], 198 with [Q or N] and 200 with [F, W, Y, L, I, or V]; substitutions at positions 116 with [G, A, S, T, or M] and 195 with [F, W, Y, L, I, or V]; substitutions at positions 116 with [G, A, S, T, or M], 195 with [F, W, Y, L, I, or V] and 198 with [Q or N]; substitutions at positions 142 with [R, K, H, Q, or N] and 146 with [G, A, S, T, or M]; substitutions at positions 142 with [R, K, H, Q, or N], 146 with [G, A, S, T, or M] and 149 with [R, K, H, Q, or N]; substitutions at positions 142 with [R, K, H, Q, or N], 146 with [G, A, S, T, or M], 149 with [R, K, H, Q, or N] and 195 with [F, W, Y, L, I, or V]; substitutions at positions 142 with [R, K, H, Q, or N], 146 with [G, A, S, T, or M], 149 with [R, K, H, Q, or N], 195 with [F, W, Y, L, I, or V] and 198 with [Q, or N]; substitutions at positions 142 with [R, K, H, Q, or N], 146 with [G, A, S, T, or M], 149 with [R, K, H, Q, or N], 195 with [F, W, Y, L, I, or V], 198 with [Q, N] and 206 with [F, W, Y, L, I, V, N, Q, or H]; substitutions at positions 151 with [R] and 210 with [F, W, Y, L, I, or V]; substitutions at positions 151 with [R], 210 with [F, W, Y, L, I, or V] and 320 with [Q, or N]; substitutions at positions 151 with [R], 210 with [F, W, Y, L, I, or V], 320 with [Q, N] and 359 with [F, W, Y, L, I, or V]; substitutions at positions 151 with [R], 210 with [F, W, Y, L, I, or V], 320 with [Q, or N], 359 with [F, W, Y, L, I, or V]

and 418 with [E, or D]; substitutions at positions 147 with [E, or D] and 149 with [R, K, H, Q, or N]; substitutions at positions 147 with [E, or D], 149 with [R, K, H, Q, or N] and 169 with [E, or D]; substitutions at positions 147 with [E, or D], 149 with [R, K, H, Q, or N], 169 with [E, or D] and 198 with [Q, or N]; substitutions at positions 147 with [E, or D], 149 with [R, K, H, Q, or N], 169 with [E, or D], 198 with [Q, or N] and 203 with [F, W, Y, L, I, or V]; substitutions at positions 147 with [E, or D], 149 with [R, K, H, Q, or N], 169 with [E, or D], 198 with [Q, or N], 203 with [F, W, Y, L, I, or V] and 206 with [F, W, Y, L, I, V, N, Q, or H]; substitutions at positions 133 with [E, or D] and 149 with [R, K, H, Q, or N]; substitutions at positions 133 with [E, or D], 149 with [R, K, H, Q, or N] and 195 with [F, W, Y, L, I, or V]; substitutions at positions 133 with [E, or D], 149 with [R, K, H, Q, or N], 195 with [F, W, Y, L, I, or V] and 198 with [Q, or N]; substitutions at positions 133 with [E, or D], 149 with [R, K, H, Q, or N], 195 with [F, W, Y, L, I, or V], 198 with [Q, or N] and 203 with [F, W, Y, L, I, or V]; substitutions at positions 147 with [E, or D] and 152 with [R, K, H, Q, or N]; substitutions at positions 147 with [E, or D], 152 with [R, K, H, Q, or N] and 169 with [E, or D]; substitutions at positions 147 with [E, or D], 152 with [R, K, H, Q, or N], 169 with [E, or D] and 198 with [Q, or N]; substitutions at positions 147 with [E, or D], 152 with [R, K, H, Q, or N], 169 with [E, or D], 198 with [Q, or N] and 206 with [F, W, Y, L, I, V, N, Q, or H]; substitutions at positions 195 with [F, W, Y, L, I, or V] and 206 with [F, W, Y, L, I, V, N, Q, or H]; substitutions at positions 195 with [F, W, Y, L, I, or V] and 243 with [F, W, Y, L, I, or V]; substitutions at positions 195 with [F, W, Y, L, I, or V] and 210 with [F, W, Y, L, I, or V]; substitutions at positions 206 with [F, W, Y, L, I, V, N, Q, or H] and 210 with [F, W, Y, L, I, or V]; substitutions at positions 186 with [R, T, K, H, E, D, Q, or N] and 195 with [F, W, Y, L, I, or V]; substitutions at positions 195 with [F, W, Y, L, I, or V] and 206 with [F, W, Y, L, I, V, N, Q, or H]; substitutions at positions 195 with [F, W, Y, L, I, or V], 206 and 243 with [F, W, Y, L, I, or V]; substitutions at positions 206 and 243 with [F, W, Y, L, I, or V]; substitutions at positions 133 with [E, or D] and 149 with [R, K, H, Q, or N]; substitutions at positions 133 with [E, or D], 149 with [R, K, H, Q, or N] and 198 with [Q, or N]; substitutions at positions 133 with [E, or D], 149 with [R, K, H, Q, or N], 198 with [Q, or N] and 206; substitutions at positions 116 with [G, A, S, T, or M] and 133 with [E, or D]; substitutions at positions 116 with [G, A, S, T, or M], 133 with [E, or D] and 147 with [E, or D]; substitutions at positions 116 with [G, A, S, T, or M], 133 with [E, or D], 147 with [E, or D] and 152 with [R, K, H, Q, or N]; substitutions at positions 116 with [G, A, S, T, or M], 133 with [E, or D], 147 with [E, or D], 152 with [R, K, H, Q, or N] and 198 with [Q, or N]; substitutions at positions 116 with [G, A, S, T, or M], 133 with [E, or D], 147 with [E, or D], 152 with [R, K, H, Q, or N], 198 with [Q, or N] and 203 with [F, W, Y, L, I, or V]; substitutions at positions 116 with [G, A, S, T, or M], 133 with [E, or D], 147 with [E, or D], 152 with [R, K, H, Q, or N], 198 with [Q, or N], 203 with [F, W, Y, L, I, or V] and 206; substitutions at positions 147 with [E, or D] and 149 with [R, K, H, Q, or N]; substitutions at positions 147 with [E, or D], 149 with [R, K, H, Q, or N] and 195 with [F, W, Y, L, I, or V]; substitutions at positions 147 with [E, or D], 149 with [R, K, H, Q, or N], 195 with [F, W, Y, L, I, or V] and 198 with [Q, or N]; substitutions at positions 147 with [E, or D], 149 with [R, K, H, Q, or N], 195 with [F, W, Y, L, I, or V], 198 with [Q, or N] and 206; substitutions at positions 133 with [E, or D] and 142 with [R, K, H, Q, or N]; substitutions at positions 133 with [E, or D], 142 with [R, K, H, Q, or N] and 195 with [F, W, Y, L, I, or V]; substitutions at positions 133 with [E, or D], 142 with [R, K, H, Q, or N], 195 with [F, W, Y, L, I, or V] and 198 with [Q, or N]; substitutions at positions 133 with [E, or D] and 149 with [R, K, H, Q, or N]; substitutions at positions 133 with [E, or D], 149 with [R, K, H, Q, or N] and 152 with [R, K, H, Q, or N]; substitutions at positions 133 with [E, or D], 149 with [R, K, H, Q, or N], 152 with [R, K, H, Q, or N] and 195 with [F, W, Y, L, I, or V]; substitutions at positions 133 with [E, or D], 149 with [R, K, H, Q, or N], 152 with [R, K, H, Q, or N], 195 with [F, W, Y, L, I, or V] and 198 with [Q, or N]; substitutions at positions 133 with [E, or D], 149 with [R, K, H, Q, or N], 152 with [R, K, H, Q, or N], 195 with [F, W, Y, L, I, or V], 198 with [Q, or N] and 206; substitutions at positions 116 with [G, A, S, T, or M] and 129 with [F, W, Y, L, I, or V]; substitutions at positions 116 with [G, A, S, T, or M], 129 with [F, W, Y, L, I, or V] and 142 with [R, K, H, Q, or N]; substitutions at positions 116 with [G, A, S, T, or M], 129 with [F, W, Y, L, I, or V], 142 with [R, K, H, Q, or N] and 195 with [F, W, Y, L, I, or V]; substitutions at positions 116 with [G, A, S, T, or M], 129 with [F, W, Y, L, I, or V], 142 with [R, K, H, Q, or N], 195 with [F, W, Y, L, I, or V] and 198 with [Q, or N]; substitutions at positions 116 with [G, A, S, T, or M], 129 with [F, W, Y, L, I, or V], 142 with [R, K, H, Q, or N], 195 with [F, W, Y, L, I, or V], 198 with [Q, or N] and 203 with [F, W, Y, L, I, or V]; substitutions at positions 116 with [G, A, S, T, or M], 129 with [F, W, Y, L, I, or V], 142 with [R, K, H, Q, or N], 195 with [F, W, Y, L, I, or V], 198 with [Q, or N], 203 with [F, W, Y, L, I, or V] and 206; substitutions at positions 133 with [E, or D] and 149 with [R, K, H, Q, or N]; substitutions at positions 133 with [E, or D], 149 with [R, K, H, Q, or N] and 152 with [R, K, H, Q, or N]; substitutions at positions 133 with [E, or D], 149 with [R, K, H, Q, or N], 152 with [R, K, H, Q, or N] and 195 with [F, W, Y, L, I, or V]; substitutions at positions 133 with [E, or D], 149 with [R, K, H, Q, or N], 152 with [R, K, H, Q, or N], 195 with [F, W, Y, L, I, or V] and 198 with [Q, or N]; substitutions at positions 133 with [E, or D], 149 with [R, K, H, Q, or N], 152 with [R, K, H, Q, or N], 195 with [F, W, Y, L, I, or V], 198 with [Q, or N] and 203 with [F, W, Y, L, I, or V]; substitutions at positions 133 with [E, or D], 149 with [R, K, H, Q, or N], 152 with [R, K, H, Q, or N], 195 with [F, W, Y, L, I, or V], 198 with [Q, or N], 203 with [F, W, Y, L, I, or V] and 206; substitutions at positions 116 with [G, A, S, T, or M] and 133 with [E, or D]; substitutions at positions 116 with [G, A, S, T, or M], 133 with [E, or D] and 149 with [R, K, H, Q, or N]; substitutions at positions 116 with [G, A, S, T, or M], 133 with [E, or D], 149 with [R, K, H, Q, or N] with [R, K, H, Q, or N] and 198 with [Q, or N]; substitutions at positions 116 with [G, A, S, T, or M], 133 with [E, or D], 149 with [R, K, H, Q, or N], 198 with [Q, or N] and 203 with [F, W, Y, L, I, or V]; substitutions at positions 116 with [G, A, S, T, or M], 133 with [E, or D], 149 with [R, K, H, Q, or N], 198 with [Q, or N], 203 with [F, W, Y, L, I, or V] and 206; substitutions at positions 195 with [F, W, Y, L, I, or V] and 198 with [Q, or N]; substitutions at positions 195 with [F, W, Y, L, I, or V], 198 with [Q, or N] and 203 with [F, W, Y, L, I, or V]; substitutions at positions 195 with [F, W, Y, L, I, or V], 198 with [Q, or N], 203 with [F, W, Y, L, I, or V] and 206 with [F, W, Y, L, I, V, N, Q, or H]; substitutions at positions 133 with [E, or D], 149 with [R, K, H, Q, or N], 195 with [F, W, Y, L, I, or V], 203 with [F, W, Y, L, I, or V], and 206 with [F, W, Y, L, I, V, N, Q, or H].

Particular useful variants according to the invention includes (using the numbering of SEQ ID NO: 6): D183* G184* N195L; D183* G184* N197F; D183* G184*

N197L; D183* G184* Y243F; D183* G184* N195F, D183* G184* N277F; D183* G184* S431T; D183* G184* P434T; D183* G184* I235N S339P; D183* G184* L351F; D183* G184* A186R, N195F; D183* G184* H210Y; D183* G184* V206Y; D183* G184* V206L; D183* G184* V206F; D183* G184* V213A Q174R; D183* G184* E212V; D183* G184* V206F E212G G304V A447V; N116T G133E K142R D183* G184* Y198N V206Y; G133E D183* G184* N195Y Y198N Y200F; D183* G184* A186D N195F E212V V213A; N116T D183* G184* N195Y Y198N; K142R P146S G149K D183* G184* N195Y Y198N V2061; D134Y D183* G184*; T151R D183* G184* H210Y K320N R359I N418D Q490H; G147E G149R Q169E D183* G184* Y198N Y203F V206Y; G133E G149R D183* G184* N195Y Y198N Y203F V206Y; G147E Y152H Q169E D183* G184* Y198N V206Y; D183* G184* N195F V206Y; D183* G184* N195F V206L; D183* G184* N195F V206F; D183* G184* V206L Y243F; D183* G184* V206F Y243F; D183* G184* N195F Y243F; D183* G184* N195F H210Y; D183* G184* V206Y H210Y; D183* G184* V213A; D183* G184* S193T; D183* G184* A186T N195F; D183* G184* N195F V206Y Y243F; D183* G184* N195F V206L Y243F; D183* G184* N195F V206Y Y243F; D183* G184* N195F V206F Y243F; D183* G184* V206Y Y243F; D183* G184* N195Y; G133D G149R D183* G184* Y198N V206Y; N116T G133E G147E Y152H D183* G184* Y198N Y203F V206Y; G147E G149R D183* G184* N195F Y198N V206Y; G133E K142R D183* G184* N195F Y198N; G133E G149R Y152H D183* G184* N195Y Y198N V206Y; N116T Q129L K142R D183* G184* N195Y Y198N Y203F V206Y; G133E G149R Y152H D183* G184* N195Y Y198N Y203F V206Y; N116T G133E G149R G182* D183* Y198N Y203F V206Y, D183* G184* S193T V206L, D183* G184* G133E G149R N195Y Y203F V206L.

In a preferred embodiment variants according to the invention includes, SP722+D183* G184* N195L; SP722+ D183* G184* N197F; SP722+D183* G184* N197L; SP722+D183* G184* Y243F; SP722+D183* G184* N195F, SP722+D183* G184* N277F; SP722+D183* G184* S431T; SP722+D183* G184* P434T; SP722+D183* G184* I235N S339P; SP722+D183* G184* L351F; SP722+D183* G184* A186D N195F E212V V213A; SP722+D183* G184* A186R N195F; SP722+D183* G184* H210Y; SP722+D183* G184* V206Y; SP722+ D183* G184* V206L, SP722+D183* G184* V206F; SP722+D183* G184* V213A Q174R; SP722+D183* G184* E212V; SP722+D183* G184* V206Y E212G G304V A447V; SP722+N116T G133E K142R D183* G184* Y198N V206Y; SP722+G133E D183* G184* N195Y Y198N Y200F; SP722+N116T D183* G184* N195Y Y198N; SP722+K142R P146S G149K D183* G184* N195Y Y198N V2061; SP722+D134Y D183* G184*; SP722+T151R D183* G184* H210Y K320N R359I N418D; SP722+G147E G149R Q169E D183* G184* Y198N Y203F V206Y; SP722+G133E G149R D183* G184* N195Y Y198N Y203F V206Y; SP722+G147E Y152H Q169E D183* G184* Y198N V206Y; SP722+ D183* G184* N195F V206Y; SP722+D183* G184* N195F V206F; SP722+D183* G184* N195F V206L; SP722+ D183* G184* I206L Y243F; SP722+D183* G184* I206F Y243F; SP722+D183* G184* N195F Y243F; SP722+ D183* G184* N195F H210Y; SP722+D183* G184* V206Y H210Y; SP722+D183* G184* V213A; SP722+ D183* G184* S193T; SP722+D183* G184* A186T N195F; SP722+D183* G184* N195F V206Y Y243F; SP722+ D183* G184* V206Y Y243F; SP722+D183* G184* N195Y; SP722+G133D G149R D183* G184* Y198N V206Y; SP722+N116T G133E G147E Y152H D183* G184* Y198N Y203F V206Y; SP722+G147E G149R D183* G184* N195F Y198N V206Y; SP722+G133E K142R D183* G184* N195F Y198N; SP722+G133E G149R Y152H D183* G184* N195Y Y198N V206Y; SP722+N116T Q129L K142R D183* G184* N195Y Y198N Y203F V206Y; SP722+G133E G149R Y152H D183* G184* N195Y Y198N Y203F V206Y; SP722+ N116T G133E G149R G182* D183* Y198N Y203F V206Y, SP722+D183* G184* G133E G149R N195Y Y203F V206L.

In one preferred embodiment the variants are selected from the following: SP722+D183* G184* N195F V206L Y243F; SP722+D183* G184* N195F V206Y Y243F; SP722+D183* G184* N195F V206N Y243F; SP722+ D183* G184* N195F V206F Y243F; SP722+D183* G184* N195F V206H; SP722+D183* G184* N195F V206Y; SP722+D183* G184* V206F Y243F; SP722+D183* G184* N195F V206L H210Y; SP722+D183* G184* S193T V206L; SP722+D183* G184* G133E G149R N195Y Y203F V206L.

In another preferred embodiment variants according to the invention includes, SP707+H183* G184* N195L; SP707+ H183* G184* N197F; SP707+H183* G184* N197L; SP707+H183* G184* Y243F; SP707+H183* G184* N195F, SP707+H183* G184* N277F; SP707+H183* G184* A186D N195F E212V V213A; SP707+H183* G184* S431T; SP707+H183* G184*A434T; SP707+H183* G184* I235N A339P; SP707+H183* G184* L351F, SP707+H183* G184* A186R, N195F; SP707+H183* G184* H210Y; SP707+H183* G184* I206Y; SP707+ H183* G184* I206L, SP707+H183* G184* I206F; SP707+ H183* G184* V213A Q174R; SP707+H183* G184* E212V; SP707+H183* G184* I206Y E212G G304V A447V; SP707+M116T G133E H183* G184* Y198N I206Y; SP707+G133E H183* G184* N195Y Y198N Y200F; SP707+M116T H183* G184* N195Y Y198N; SP707+P146S G149K H183* G184* N195Y Y198N V2061; SP707+E134Y H183* G184*; SP707+T151R H183* G184* H210Y R320N R359I N418D; SP707+ G147E G149R Q169E H183* G184* Y198N Y203F I206Y; SP707+G133E G149R H183* G184* N195Y Y198N Y203F I206Y; SP707+G147E Q169E H183* G184* Y198N I206Y; SP707+H183* G184* N195F I206Y; SP707+H183* G184* N195F I206L; SP707+H183* G184* N195F I206F; SP707+H183* G184* N195F Y243F; SP707+H183* G184* N195F H210Y; SP707+H183* G184* I206Y H210Y; SP707+H183* G184* V213A; SP707+H183* G184* S193T; SP707+H183* G184* A186T N195F; SP707+H183* G184* N195F I206Y Y243F; SP707+ H183*G184* N195F I206F Y243F; SP707+H183*G184* N195F I206L Y243F; SP707+H183* G184* N195F I206Y Y243F SP707+H183* G184* I206Y Y243F; SP707+H183* G184* I206L Y243F; SP707+H183* G184* I206F Y243F; SP707+H183* G184* N195Y; SP707+G133D G149R H183* G184* Y198N I206Y; SP707+M116T G133E G147E H183*G184*Y198N Y203F I206Y; SP707+G147E G149R+H183*G184* N195F Y198N I206Y; SP707+ G133E H183* G184* N195F Y198N; SP707+G133E G149R H183* G184* N195Y Y198N I206Y; SP707+ M116T Q129L H183* G184* N195Y Y198N Y203F I206Y; SP707+G133E G149R H183*G184* N195Y Y198N Y203F I206Y; SP707+M116T G133E G149R G182* H183* Y198N Y203F I206Y; SP707+D183* G184* R118K N195F R320K R458K; SP707+D183* G184* R118K N195F I206L R320K R458K; SP707+D183* G184* R118K N195F I206Y R320K R458K; SP707+D183* G184* R118K N195F Y243F R320K R458K; SP707+D183*G184* R118K N195F I206L Y243F R320K R458K.

In a preferred embodiment variants according to the invention includes, AA560+D183* G184* N195L; AA560+D183* G184* N197F; AA560+D183* G184* N197L; AA560+D183* G184* Y243F; AA560+D183* G184* N195F, AA560+D183* G184* N277F; AA560+D183* G184* S431T; AA560+D183* G184* A434T; AA560+D183* G184* I235N A339P; AA560+D183* G184* L351F; D183* G184* G186D N195F E212V V213A AA560+D183* G184* G186R, N195F; AA560+D183* G184* H210Y; AA560+D183* G184* I206Y; AA560+D183* G184* I206L; AA560+D183* G184* I206F; AA560+D183* G184* V213A Q174R; AA560+D183* G184* E212V; AA560+D183* G184* I206Y E212G G304V A447V; AA560+M116T G133E K142R D183* G184* Y198N I206Y; AA560+G133E D183* G184* N195Y Y198N Y200F; AA560+M116T D183* G184* N195Y Y198N; AA560+K142R P146S G149K D183* G184* N195Y Y198N I2061; AA560+E134Y D183* G184*; AA560+T151R D183* G184* H210Y R320N R359I N418D; AA560+G147E G149R Q169E D183* G184* Y198N Y203F I206Y; AA560+G133E G149R D183* G184* N195Y Y198N Y203F I206Y; AA560+G147E Y152H Q169E D183* G184* Y198N I206Y; AA560+D183* G184* N195F I206Y; AA560+D183* G184* N195F I206L; AA560+D183* G184* N195F I206F; AA560+D183* G184* I206L Y243F; AA560+D183* G184* I206F Y243F; AA560+D183* G184* N195F Y243F; AA560+D183* G184* N195F H210Y; AA560+D183* G184* I206Y H210Y; AA560+D183* G184* V213A; AA560+D183* G184* S193T; AA560+D183* G184* G186T N195F; AA560+D183* G184* N195F I206Y Y243F, AA560+D183* G184* N195F I206L Y243F; AA560+D183* G184* N195F I206Y Y243F AA560+D183* G184* I206Y Y243F; AA560+D183* G184* I206L Y243F; AA560+D183* G184* N195Y; AA560+G133D G149R D183* G184* Y198N I206Y; AA560+M116T G133E G147E Y152H D183* G184* Y198N Y203F I206Y; AA560+G147E G149R D183* G184* N195F Y198N I206Y; AA560+G133E K142R D183* G184* N195F Y198N; AA560+G133E G149R Y152H D183* G184* N195Y Y198N I206Y; AA560+M116T Q129L K142R D183* G184* N195Y Y198N Y203F I206Y; AA560+G133E G149R Y152H D183*G184* N195Y Y198N Y203F I206Y; AA560+M116T G133E G149R G182* D183* Y198N Y203F I206Y; AA560+D183* G184* R118K N195F R320K R458K; AA560+D183* G184* R118K N195F I206L R320K R458K; AA560+D183* G184* R118K N195F I206Y R320K R458K; AA560+D183* G184* R118K N195F Y243F R320K R458K; AA560+D183* G184* R118K N195F I206L Y243F R320K R458K.

In a preferred embodiment variants according to the invention includes, SP690+T183* G184* N195L; SP690+T183* G184* N197F; SP690+T183* G184* N197L; SP690+T183* G184* Y243F; SP690+T183* G184* N195F, SP690+T183* G184* N277F; SP690+T183* G184* S431T; SP690+T183* G184* P434T; SP690+T183* G184* 1235N A339P; SP690+T183* G184* L351F; SP690+T183* G184* A186D N195F E212V V213A; SP690+T183* G184* A186R N195F; SP690+T183* G184* H210Y; SP690+T183* G184* V206Y; SP690+T183* G184* V206L, SP690+T183* G184* V206F; SP690+T183* G184* V213A Q174R; SP690+T183* G184* E212V; SP690+T183* G184* V206Y E212G G304V A447V; SP690+N116T G133E K142R T183* G184* Y198N V206Y; SP690+G133E T183* G184* N195Y Y198N Y200F; SP690+N116T T183* G184* N195Y Y198N; SP690+K142R P146S G149K T183* G184* N195Y Y198N V2061; SP690+E134Y T183* G184*; SP690+N151R T183* G184* H210Y K320N R359I N418D; SP690+G147E G149R Q169E T183* G184* Y198N Y203F V206Y; SP690+G133E G149R T183* G184* N195Y Y198N Y203F V206Y; SP690+G147E Y152H Q169E T183* G184* Y198N V206Y; SP690+T183* G184* N195F V206Y; SP690+T183* G184* N195F V206F; SP690+T183* G184* N195F V206L; SP690+T183* G184* I206L Y243F; SP690+T183* G184* I206F Y243F; SP690+T183* G184* N195F Y243F; SP690+T183* G184* N195F H210Y; SP690+T183* G184* V206Y H210Y; SP690+T183* G184* V213A; SP690+T183* G184* S193T; SP690+T183* G184*A186T N195F; SP690+T183* G184* N195F V206Y Y243F; SP690+T183* G184* V206Y Y243F; SP690+T183* G184* N195Y; SP690+G133D G149R T183* G184* Y198N V206Y; SP690+N116T G133E G147E Y152H T183* G184* Y198N Y203F V206Y; SP690+G147E G149R T183* G184* N195F Y198N V206Y; SP690+G133E K142R T183* G184* N195F Y198N; SP690+G133E G149R Y152H T183* G184* N195Y Y198N V206Y; SP690+N116T Q129L K142R T183* G184* N195Y Y198N Y203F V206Y; SP690+G133E G149R Y152H T183* G184* N195Y Y198N Y203F V206Y; SP690+N116T G133E G149R G182* T183* Y198N Y203F V206Y, SP690+T183* G184* G133E G149R N195Y Y203F V206L, SP690+T183* G184* R118K N195F R320K R458K; SP690+T183* G184* N118K N195F V206L R320K R458K; SP690+T183* G184* N118K N195F V206Y R320K R458K; SP690+T183* G184* N118K N195F Y243F R320K R458K; SP690+T183* G184* N118K N195F V206L Y243F R320K R458K; SP690+T183* G184* N195F V206L Y243F; SP690+T183* G184* N195F V206Y Y243F; SP690+T183* G184* N195F V206N Y243F; SP690+T183* G184* N195F V206F Y243F; SP690+T183* G184* N195F V206H; SP690+T183* G184* N195F V206Y; SP690+T183* G184* V206F Y243F; SP690+T183* G184* N195F V206L H210Y; SP690+T183* G184* S193T V206L; SP690+T183* G184* G133E G149R N195Y Y203F V206L.

In a preferred embodiment, variants according to the invention includes a variant of a parent alpha-amylase, wherein the parent alpha-amylase is that of SEQ ID NO:6, and the variant comprises the deletions D183* and G184* and one of the following sets of mutations: (a) N195F+H210Y; (b) N195F+V206L,H,Y; (c) N195F+V206L,F+H210Y; (d) N195F+V206Y+Y243F; (e) N195F+Y243F; (f) S193T+V206L; (g) G133E+G149R+N195Y+Y203F+V206L; (h) V206L,Y; (i) Y243F; (j) N195F+V206L+Y243F; (k) N195F; or (1) V206F+Y243F.

Detergent Compositions: According to the invention, the above alpha-amylase variants may typically be a component of a detergent composition, e.g., a laundry detergent composition or a dishwashing detergent composition. In a special embodiment of the invention the composition further comprises a strong chelating agent or complexing agent. Thus one aspect of the invention concerns a composition comprising a variant of a parent alpha-amylase comprising a substitution at one or more position in the range corresponding to positions 193 to 213 of the mature polypeptide of SEQ ID NO: 6 and further comprising a chelating agent wherein said chelating agent at a concentration below 10 mM is capable of reducing the concentration of free calcium ions from 2.0 mM to 0.10 mM when measured at 21° C. and pH 8.0, as described under "Materials and Methods".

In another embodiment the composition comprises a chelating agent selected from, but not limited, to the following: The chelating agent may contain an amino group and may be, e.g., an amino-polycarboxylate or a phosphonate. It may be a monomeric molecule comprising one, two or three amino groups (typically secondary or tertiary amino groups), and it may contain two, three, four or five or even more carboxyl groups. Chelating agents may be but are not limited to the following: ethylene-diamine-tetra-acetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine di-acetic acid (MGDA), diethylene triamine penta acetic acid (DTPA), propylene diamine tetracetic acid (PDTA), 2-hydroxypyridine-N-oxide (HPNO), or ethylenedinitrilotertrakis (methylenephosphonic acid) N,N-dioxide, methyl glycine diacetic acid (MGDA), glutamic acid N,N-diacetic acid (N,N-dicarboxymethyl glutamic acid tetrasodium salt, (GLDA) and nitrilotriacetic acid (NTA) or mixtures thereof. The chelating agents are typically present at a level of from 0.1% to 75% by weight in a detergent.

The detergent composition of the present invention may further comprise a cleaning/detergent adjunct, which is not a chelating agent as defined above, preferably comprising a mixture of components. Typically the cleaning adjunct will be present in the composition in an amount from 0.001 to 99.9 wt %, more typically from 0.01 to 80 wt % cleaning adjunct. Suitable cleaning adjuncts comprise: surfactants, builders, bleaches, bleach catalysts, colorants, bleach boosters, dye transfer agents, deposition aids, dispersants, additional enzymes, and enzyme stabilizers, catalytic materials, bleach activators, hydrogen peroxide, sources of hydrogen peroxide, optical brighteners, photoactivators, fluorescers, fabric hueing agents, fabric conditioners, preformed peracids, polymeric dispersing agents, clay soil removal/anti-redeposition agents, filler salts, hydrotropes, brighteners, suds suppressors, structure elasticizing agents, fabric softeners, hydrolyzable surfactants, preservatives, anti-oxidants, anti-shrinkage agents, germicides, fungicides, anti-tarnish, anti-corrosion agents, alkalinity sources, solubilizing agents, carriers, processing aids, pigments, dyes, perfumes and pH control agents. For example, these may include: bleach ingredients such as imine bleach boosters; sources of hydrogen peroxide such as percarbonate and/or perborate, especially percarbonate coated with material such as carbonate and/or sulphate salt, silicate salt, borosilicate, and any mixture thereof; pre-formed peracid, including pre-formed peracid in encapsulated form; transition metal catalysts; suds suppressors or suppressor systems such as silicone based suds suppressors and/or fatty acid based suds suppressors; fabric-softeners such as clay, silicone and/or quaternary ammonium compounds; flocculants such as polyethylene oxide; dye transfer inhibitors such as polyvinylpyrrolidone, poly 4-vinylpyridine N-oxide and/or co-polymer of vinylpyrrolidone and vinylimidazole; fabric integrity components such as oligomers produced by the condensation of imidazole and epichlorhydrin; soil dispersants and soil anti-redeposition aids such as alkoxylated polyamines and ethoxylated ethyleneimine polymers; anti-redeposition components such as polyesters; carboxylate polymers such as maleic acid polymers or co-polymers of maleic and acrylic acid; perfumes such as perfume microcapsules, starch encapsulated accords, perfume spray-on; soap rings; aesthetic particles; dyes; fillers such as sodium sulphate, although it is preferred for the composition to be substantially free of fillers; silicate salt such as sodium silicate, including 1.6R and 2.0R sodium silicate, or sodium metasilicate; co-polyesters of di-carboxylic acids and diols; cellulosic polymers such as methyl cellulose, carboxymethyl cellulose, hydroxyethoxycellulose, or other alkyl or alkylalkoxy cellulose; solvents such as 1,2 propanediol, monoethanolamine; diethylene glycol, ethanol, and any mixture thereof; hydrotropes such as sodium cumene sulphonate, sodium xylene sulphonate, sodium toluene sulphonate, and any mixtures; organic acids such as citric acid; and any combination thereof.

Accordingly, the composition may further contain builders, such as builders based on carbonate, bicarbonate or silicates which may be Zeolittes, such as Zeolit A, Zeolit MAP (Miximum Aluminium type P). Zeolites, useable in laundry preferably has the formula $Na_{12}(AlO_2)_{12}(SiO_2)_{12}\cdot 27H_2O$ and the particle size is usually between 1-10 μm for zeolit A and 0.7-2 um for zeolit MAP. Other builders are Sodium metasilicate ($Na_2SiO_3\cdot nH_2O$ or $Na_2Si_2O_5\cdot n\ H_2O$) strong alkaline and preferably used in dish wash. In preferred embodiments, the amount of a detergent builder may be above 5%, above 10%, above 20%, above 30%, above 40% or above 50%, and may be below 80%, 65%. In a dishwash detergent, the level of builder is typically 40-65%, particularly 50-65% or even 75-90%.

In another preferred aspect the composition comprises one or more surfactants, which may be non-ionic including semi-polar and/or anionic and/or cationic and/or zwitterionic and/or ampholytic and/or semi-polar nonionic and/or mixtures thereof. The surfactants are typically present at a level of from 0.1% to 60% by weight, while in alternative embodiments, the level is from about 1 percent to about 50 percent, while in still further embodiments, the level is from about 5 percent to about 40 percent, by weight of the detergent composition.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

Further suitable anionic surfactants are soaps and those containing sulfate or sulfonate groups. Surfactants of the sulfonate type that come into consideration are (C9-C13-alkyl)benzenesulfonates and olefinsulfonates, the latter being understood to be mixtures of alkenesulfonates and hydroxyalkanesulfonates and -disulfonates, as obtained, for example, by sulfonation of C12-C18 monoolefins having a terminally or internally located double bond. Also suitable are (C12-C18)alkanesulfonates and esters of alpha-sulfo fatty acids (ester sulfonates), for example the alpha-sulfonated methyl esters of hydrogenated coconut, palm kernel or tallow fatty acids, typically produced by saponification of triglycerides from the plant or animal oils followed by methylation and sulfonation, may be used.

Further suitable anionic surfactants are sulfonated fatty acid glycerol esters comprising mono-, di- and tri-esters and mixtures thereof.

Alk(en)yl sulfates to which preference is given are the alkali metal salts and the sodium salts of sulfuric acid monoesters of C12-C18 fatty alcohols, for example from coconut fatty alcohol, tallow fatty alcohol, lauryl, myristyl, cetyl or stearyl alcohol, or of C10-C20 oxo alcohols and sulfuric acid monoesters of secondary alcohols having that chain length. From the point of view of washing technology, special preference is given to C12-C16 alkyl sulfates and C12-C15 alkyl sulfates and also to C14-C15 alkyl sulfates. Suitable anionic surfactants are also alkane-2,3-diylbis(sulfates) that are prepared, for example, in accordance with U.S. Pat. No. 3,234,258 or U.S. Pat. No. 5,075,041.

Also suitable are the sulfuric acid monoesters of straight-chain or branched C7-C21 alcohols ethoxylated with from 1 to 6 mole of ethylene oxide, such as 2-methyl-branched C9-C11 alcohols with, on average, 3.5 mole of ethylene oxide (EO) or C12-C18 fatty alcohols with from 1 to 4 EO. Because of their high foaming characteristics, they are normally used in washing and cleaning compositions only at relatively low levels, for example at levels of from 1% to 5% by weight.

Anionic surfactants may also include diesters, and/or salts of monoesters, of sulfosuccinic acid with C8-C18 fatty alcohol residues or mixtures thereof. Special preference is given to sulfosuccinates in which the fatty alcohol residues have a narrow chain length distribution. It is likewise also possible to use alk(en)yl sulfosuccinates having preferably from 8 to 18 C-atoms in the alk(en)yl chain, or salts thereof.

Further anionic surfactants that come into consideration are fatty acid derivatives of amino acids, for example of methyltaurine (taurides) and/or of methylglycine (sarcosides). Further anionic surfactants that come into consideration are soaps. Saturated fatty acid soaps such as the salts of lauric acid, myristic acid, palmitic acid, stearic acid, hydrogenated erucic acid and behenic acid and soap mixtures derived from natural fatty acids, for example coconut, palm kernel or tallow fatty acids. The anionic surfactants, including the soaps, may be present in the form of their sodium, potassium or ammonium salts and in the form of soluble salts of organic bases such as mono-, di- or triethanolamine. The anionic surfactants may be present in the form of their sodium or potassium salts. As non-ionic surfactants, preferably alkoxylated, advantageously ethoxylated and/or propoxylated, especially primary alcohols having from 8 to 18 C-atoms and, on average, from 1 to 12 moles of ethylene oxide (EO) and/or from 1 to 10 moles of propylene oxide (PO) per mole of alcohol are used. Special preference is given to C8-C16 alcohol alkoxylates, advantageously ethoxylated and/or propoxylated C10-C15 alcohol alkoxylates, especially C12-C14 alcohol alkoxylates, having a degree of ethoxylation between 2 and 10, or between 3 and 8, and/or a degree of propoxylation between 1 and 6, or between 1.5 and 5. The alcohol residue may be preferably linear or, especially in the 2-position, methyl-branched, or may comprise a mixture of linear and methyl-branched chains, as are usually present in oxo alcohols.

Special preference is given, however, to alcohol ethoxylates derived from linear alcohols of natural origin that contain from 12 to 18 C-atoms, for example coconut, palm and tallow fatty alcohol or oleyl alcohol, and on average from 2 to 8 EO per mole of alcohol. The ethoxylated alcohols include, for example, C12-C14 alcohols with 3 EO or 4 EO, C9-C11 alcohols with 7 EO, C13-C15 alcohols with 3 EO, 5 EO, 7 EO or 8 EO, C12-18 alcohols with 3 EO, 5 EO or 7 EO, mixtures thereof, such as mixtures of C12-C14 alcohol with 3 EO and C12-C18 alcohol with 5 EO. The mentioned degrees of ethoxylation and propoxylation represent statistical averages which, for a specific product, can be a whole number or a fractional number. Preferred alcohol ethoxylates and propoxylates have a restricted homologue distribution (narrow range ethoxylates/propoxylates, NRE/NRP). In addition to those non-ionic surfactants, fatty alcohol ethoxylates having more than 12 EO may also be used. Examples thereof are tallow fatty alcohol ethoxylate with 14 EO, 25 EO, 30 EO or 40 EO.

Also suitable are alkoxylated amines, which are ethoxylated and/or propoxylated, especially primary and secondary amines having from 1 to 18 C-atoms per alkyl chain and, on average, from 1 to 12 moles of ethylene oxide (EO) and/or from 1 to 10 moles of propylene oxide (PO) per mole of amine.

In addition, as further non-ionic surfactants, there may also be used alkyl polyglycosides of the general formula $R_1O(G)_x$, wherein $R_1$ is a primary straight-chain or methyl-branched (especially methyl-branched in the 2-position) alkyl group having from 8 to 22, preferably from 12 to 18, C-atoms and the symbol 'G' indicates a glycose (monosaccharide) unit having 5 or 6 C-atoms; preferably G is glucose. The degree of oligomerisation x, which indicates the average number of glycose units, will generally lie between 1 and 10; x is preferably from 1.2 to 1.4.

A further class of used non-ionic surfactants, which are used either as sole non-ionic surfactant or in combination with other non-ionic surfactants, comprises alkoxylated, preferably ethoxylated or ethoxylated and propoxylated fatty acid alkyl esters, having from 1 to 4 C-atoms in the alkyl chain, especially fatty acid methyl esters, as described, for example, in JP58/217598.

Non-ionic surfactants of the amine oxide type, for example N-(coco alkyl)-N,N-dimethylamine oxide and N-(tallow-alkyl)-N,N-bis(2-hydroxyethyl)amine oxide, and of the fatty acid alkanolamide or ethoxylated fatty acid alkanolamide type may also be suitable.

In a more preferred embodiment, the surfactant is sodium dodecyl sulfate, quaternary ammonium compounds, alkyl pyridinium iodides, TWEEN™ 80 (polysorbate 80), TWEEN™ 85 (polyoxyethylene sorbitan trioleate), TRITON™ X-100 (2-[4-(2,4,4-trimethylpentan-2-yl)phenoxy]ethanol), Brij 56, biological surfactants, rhamnolipid, surfactin, visconsin, or sulfonates.

In some embodiments the invention relates to a composition wherein the concentration of the at least one surfactant is from 0 to 500, from 0.00001 to 100, from 0.0001 to 50, from 0.0001 to 40, from 0.001 to 30, from 0.01 to 20, from 0.1 to 15, from 1 to 10 milligram per gram textile in the wash.

In some embodiments the invention relates to a composition, wherein the concentration of the at least one surfactant is from 0 to 50, from 0.0001 to 40, from 0.001 to 30, from 0.01 to 20 from 0.1 to 10, or from 1 to 5 g per L solution.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. The detergent may be a powder, or granulated form, or it may be in the form of a liquid, gel or paste or in the form of a unit dose product such as a tablet or pouch, including multi-compartment pouches, or the detergent can be in the form of a sheet.

The detergent composition may comprise one or more other enzymes such as a protease, a lipase, a peroxidase, another amylolytic enzyme, e.g., another alpha-amylase, glucoamylase, maltogenic amylase, CGTase and/or a cellulase, mannanase (such as MANNAWAY™ from Novozymes, Denmark), pectinase, pectine lyase, cutinase, and/or laccase.

In general, the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include metalloproteases and/or serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, B. alkalophilus, B. subtilis, B. amyloliquefaciens, Bacillus pumilus* and *Bacillus gibsonii* described in U.S. Pat. Nos. 6,312,936 B1, 5,679,630, 4,760,025, 7,262,042 and WO 2009/021867.

(b) trypsin-type or chymotrypsin-type proteases, such as trypsin (e.g., of porcine or bovine origin), including the *Fusarium* protease described in WO 89/06270 and the chymotrypsin proteases derived from Cellumonas described in WO 2005/052161 and WO 2005/052146.

(c) metalloproteases, including those derived from *Bacillus amyloliquefaciens* described in WO 2007/044993.

Preferred proteases include those derived from *Bacillus gibsonii* or *Bacillus lentus.*

Suitable commercially available protease enzymes include those sold under the trade names ALCALASE®, SAVINASER, PRIMASER, DURAZYM®, POLARZYMER, KANNASER, LIQUANASER, LIQUANASE ULTRAR, SAVINASE ULTRAR, OVOZYMER, NEUTRASER, EVERLASER and ESPERASER by Novozymes A/S (Denmark), those sold under the tradename MAXATASE®, MAXACAL®, MAXAPEM®, PROPERASER, PURAFECT®, PURAFECT PRIMER, PURAFECT OX®, FN3®, FN4®, EXCELLASER and PURAFECT OXP® by Genencor International, those sold under the tradename OPTICLEAN® and OPTIMASE® by Solvay Enzymes, those available from Henkel/Kemira, namely BLAP (sequence shown in FIG. 29 of U.S. Pat. No. 5,352,604 with the folowing mutations S99D+S101R+S103A+V104I+G159S, hereinafter referred to as BLAP), BLAP R (BLAP with S3T+V41+V199M+V2051+L217D), BLAP X (BLAP with S3T+V41+V2051) and BLAP F49 (BLAP with S3T+V41+A194P +V199M+V2051+L217D)—all from Henkel/Kemira; and KAP (*Bacillus alkalophilus* subtilisin with mutations A230V+S256G+S259N) from Kao.

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta* 1131: 253-360), *B. stearothermophilus* (JP 64/744992) or *B. pumilus* (WO 91/16422).

The lipase may be a "first cycle lipase" such as those described in U.S. Pat. No. 6,939,702 and US 2009/0217464. In one aspect, the lipase is a first-wash lipase, preferably a variant of the wild-type lipase from *Thermomyces lanuginosus* comprising T231R and N233R mutations. The wild-type sequence is the 269 amino acids (amino acids 23-291) of the Swissprot accession number Swiss-Prot 059952 (derived from *Thermomyces lanuginosus* (*Humicola lanuginosa*)). Preferred lipases would include those sold under the tradenames Lipex®, Lipolex® and Lipoclean®. Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases: Suitable peroxidases/oxidases include those of plant, bac-terial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME® (Novozymes A/S).

Other enzymes: Other preferred enzymes include pectate lyases sold under the tradenames PECTAWASH®, PECTAWAY® and mannanases sold under the tradenames MANNAWAY® (all from Novozymes A/S, Bagsvaerd, Denmark), and PURABRITE® (Genencor International Inc., Palo Alto, California).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste, a gel, a liquid, a powder-form all-purpose, a “heavy-duty” washing agent, a paste-form all-purpose, a heavy-duty liquid type, a liquid fine-fabric, a hand dishwashing agent, a light duty dishwashing agent, a high-foaming type. a machine dishwashing agent, a various tablet, a dishwash granular, a dish wash liquid, a rinse-aid type. The composition can also be in unit dose packages, including those known in the art and those that are water soluble, water insoluble and/or water permeable. A liquid detergent may be aqueous, typically containing up to 70% water and 0-30% organic solvent, or non-aqueous or a solution containing more than 0.5 g/L of the detergent composition. The composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. The detergent may be a powder, or granulated form, or it may be in the form of a liquid, gel or paste or in the form of a unit dose product such as a tablet or pouch, including multi-compartment pouches, or the detergent can be in the form of a sheet.

The composition may comprise a fabric hueing agent. Suitable fabric hueing agents include dyes, dye-clay conjugates, and pigments that preferably satisfy the requirements of Test Method 1, described herein below. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example:

(1) Tris-azo direct blue dyes of the formula

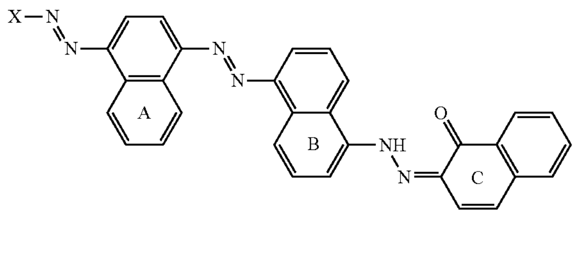

where at least two of the A, B and C napthyl rings are substituted by a sulfonate group, the C ring may be substituted at the 5 position by an $NH_2$ or NHPh group, X is a benzyl or naphthyl ring substituted with up to 2 sulfonate groups and may be substituted at the 2 position with an OH group and may also be substituted with an $NH_2$ or NHPh group.

(2) bis-azo Direct violet dyes of the formula:

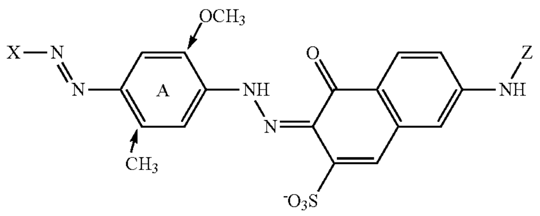

where Z is H or phenyl, the A ring is preferably substituted by a methyl and methoxy group at the positions indicated by arrows, the A ring may also be a naphthyl ring, the Y group is a benzyl or naphthyl ring, which is substituted by sulfate group and may be mono or disubstituted by methyl groups.

(3) Blue or red acid dyes of the formula

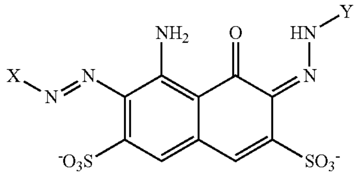

where at least one of X and Y must be an aromatic group. In one aspect, both the aromatic groups may be a substituted benzyl or naphthyl group, which may be substituted with non water-solubilising groups such as alkyl or alkyloxy or aryloxy groups, X and Y may not be substituted with water solubilising groups such as sulfonates or carboxylates. In another aspect, X is a nitro substituted benzyl group and Y is a benzyl group (4) Red acid dyes of the structure

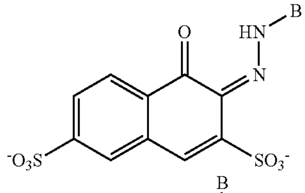

or

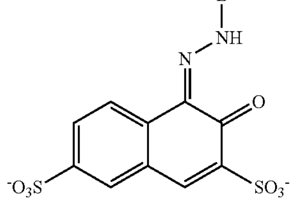

where B is a naphthyl or benzyl group that may be substituted with non water solubilising groups such as alkyl or alkyloxy or aryloxy groups, B may not be substituted with water solubilising groups such as sulfonates or carboxylates.

(5) Dis-azo dyes of the structure

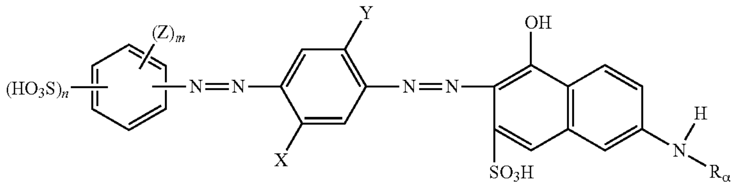

or

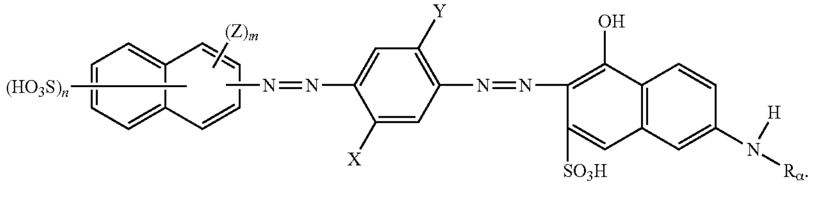

wherein X and Y, independently of one another, are each hydrogen, $C_1$-$C_4$ alkyl or $C_1$-$C_4$-alkoxy, $R_\alpha$ is hydrogen or aryl, Z is $C_1$-$C_4$ alkyl; $C_1$-$C_4$-alkoxy; halogen; hydroxyl or carboxyl, n is 1 or 2 and m is 0, 1 or 2, as well as corresponding salts thereof and mixtures thereof (6) Triphenyl methane dyes of the following structures

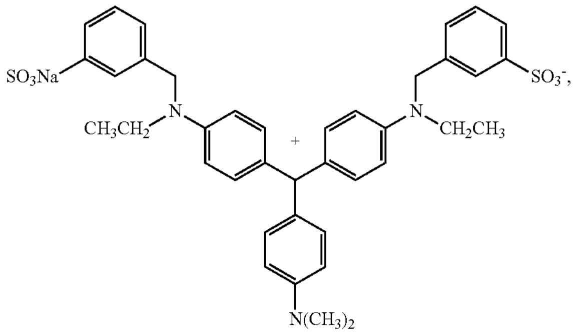

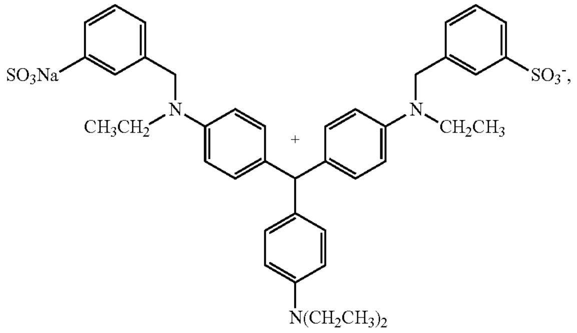

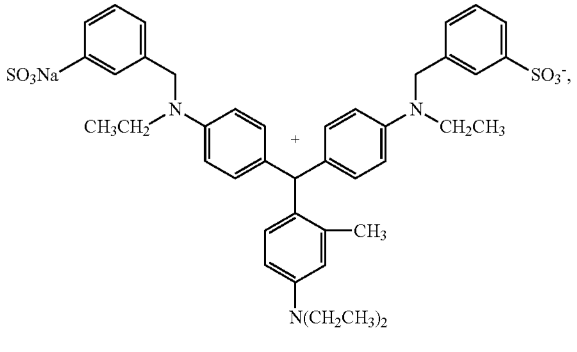

-continued

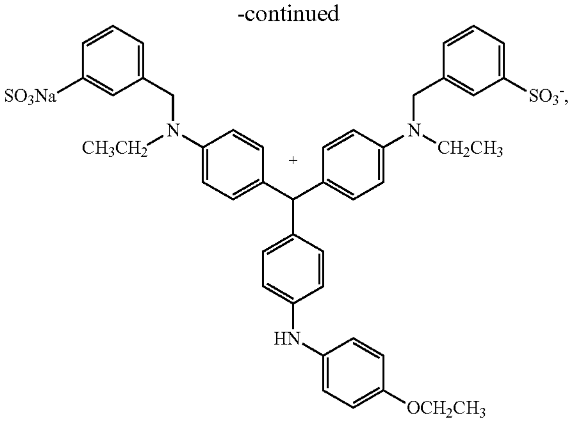

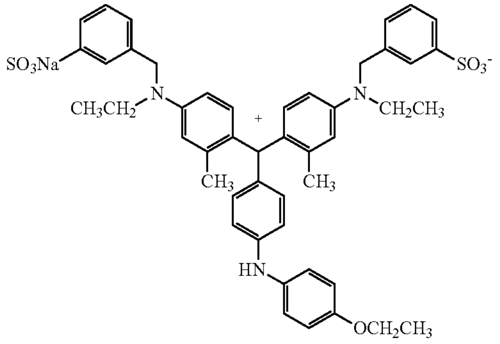

and/or

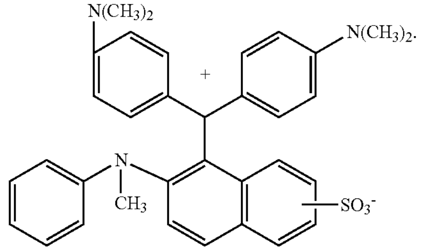

and mixtures thereof. In another aspect, suitable small molecule dyes include small molecule dyes selected from the group consisting of Colour Index (Society of Dyers and Colourists, Bradford, UK) numbers Direct Violet 9, Direct Violet 35, Direct Violet 48, Direct Violet 51, Direct Violet 66, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof. In another aspect, suitable small molecule dyes include small molecule dyes selected from the group consisting of Colour Index (Society of Dyers and Colourists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71, Direct Violet 51 and mixtures thereof. In another aspect, suitable small molecule dyes include small molecule dyes selected from the group consisting of Colour Index (Society of Dyers and Colourists, Bradford, UK) numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of fabric-substantive colorants sold under the name of LIQUITINT® (Milliken, Spartanburg, South Carolina, USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of LIQUITINT® (Milliken, Spartanburg, South Carolina, USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable fabric hueing agents can be purchased from Aldrich, Milwaukee, Wisconsin, USA; Ciba Specialty Chemicals, Basel, Switzerland; BASF, Ludwigshafen, Germany; Dayglo Color Corporation, Mumbai, India; Organic Dyestuffs Corp., East Providence, Rhode Island, USA; Dystar, Frankfurt, Germany; Lanxess, Leverkusen, Germany; Megazyme, Wicklow, Ireland; Clariant, Muttenz, Switzerland; Avecia, Manchester, UK and/or made in accordance with the examples contained herein. Suitable hueing agents are described in more detail in U.S. Pat. No. 7,208,459 B2.

Test Method 1

A protocol to define whether a dye or pigment material is a fabric hueing agent for the purpose of the invention is given here:

1) Fill two tergotometer pots with 800 ml of Newcastle upon Tyne, UK, City Water (~12 grains per US gallon total hardness, supplied by Northumbrian Water, Pity Me, Durham, Co. Durham, UK).
2) Insert pots into tergotometer, with water temperature controlled at 30° C. and agitation set at 40 rpm for the duration of the experiment.
3) Add 4.8 g of IEC-B detergent (IEC 60456 Washing Machine Reference Base Detergent Type B), supplied by wfk, Brüggen-Bracht, Germany, to each pot.
4) After two minutes, add 2.0 mg active colorant to the first pot.
5) After one minute, add 50 g of flat cotton vest (supplied by Warwick Equest, Consett, County Durham, UK), cut into 5 cm×5 cm swatches, to each pot.
6) After 10 minutes, drain the pots and re-fill with cold Water (16° C.) having a water hardness of 14.4 English Clark Degrees Hardness with a 3:1 Calcium to Magnesium molar ratio.
7) After 2 minutes rinsing, remove fabrics.
8) Repeat steps 3-7 for a further three cycles using the same treatments.
9) Collect and line dry the fabrics indoors for 12 hours.

10) Analyse the swatches using a Hunter Miniscan spectrometer fitted with D65 illuminant and UVA cutting filter, to obtain Hunter a (red-green axis) and Hunter b (yellow-blue axis) values.

11) Average the Hunter a and Hunter b values for each set of fabrics. If the fabrics treated with colorant under assessment show an average difference in hue of greater than 0.2 units on either the a axis or b axis, it is deemed to be a fabric hueing agent for the purpose of the invention.

The composition may comprise an encapsulate. In one aspect, an encapsulate comprising a core, a shell having an inner and outer surface, said shell encapsulating said core.

In one aspect of said encapsulate, said core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

In one aspect of said encapsulate, said core may comprise perfume.

In one aspect of said encapsulate, said shell may comprise melamine formaldehyde and/or cross-linked melamine formaldehyde.

In one aspect, suitable encapsulates may comprise a core material and a shell, said shell at least partially surrounding said core material, is disclosed. At least 75%, 85% or even 90% of said encapsulates may have a fracture strength of from about 0.2 MPa to about 10 MPa, from about 0.4 MPa to about 5 MPa, from about 0.6 MPa to about 3.5 MPa, or even from about 0.7 MPa to about 3 MPa; and a benefit agent leakage of from 0% to about 30%, from 0% to about 20%, or even from 0% to about 5%.

In one aspect, at least 75%, 85% or even 90% of said encapsulates may have a particle size of from about 1 micron to about 80 microns, about 5 microns to 60 microns, from about 10 microns to about 50 microns, or even from about 15 microns to about 40 microns.

In one aspect, at least 75%, 85% or even 90% of said encapsulates may have a particle wall thickness of from about 30 nm to about 250 nm, from about 80 nm to about 180 nm, or even from about 100 nm to about 160 nm.

In one aspect, said encapsulates' core material may comprise a material selected from the group consisting of a perfume raw material and/or optionally a material selected from the group consisting of vegetable oil, including neat and/or blended vegetable oils including caster oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil and mixtures thereof; aromatic solvents, including benzene, toluene and mixtures thereof; silicone oils; and mixtures thereof.

In one aspect, said encapsulates' wall material may comprise a suitable resin including the reaction product of an aldehyde and an amine, suitable aldehydes include formaldehyde. Suitable amines include melamine, urea, benzoguanamine, glycoluril, and mixtures thereof. Suitable melamines include methylol melamine, methylated methylol melamine, imino melamine and mixtures thereof. Suitable ureas include dimethylol urea, methylated dimethylol urea, urea-resorcinol, and mixtures thereof.

In one aspect, suitable formaldehyde scavengers may be employed with the encapsulates, for example, in a capsule slurry and/or added to a consumer product before, during or after the encapsulates are added to such consumer product.

Suitable capsules that can be made by following the teaching of US 2008/0305982 and/or US 2009/0247449. Alternatively, suitable capsules can be purchased from Appleton Papers Inc. of Appleton, Wisconsin USA.

In addition, the materials for making the aforementioned encapsulates can be obtained from Solutia Inc. (St Louis, Missouri U.S.A.), Cytec Industries (West Paterson, New Jersey U.S.A.), sigma-Aldrich (St. Louis, Missouri U.S.A.), CP Kelco Corp. of San Diego, California, USA; BASF AG of Ludwigshafen, Germany; Rhodia Corp. of Cranbury, New Jersey, USA; Hercules Corp. of Wilmington, Delaware, USA; Agrium Inc. of Calgary, Alberta, Canada, ISP of New Jersey U.S.A., Akzo Nobel of Chicago, IL, USA; Stroever Shellac Bremen of Bremen, Germany; Dow Chemical Company of Midland, MI, USA; Bayer AG of Leverkusen, Germany; Sigma-Aldrich Corp., St. Louis, Missouri, USA.

In one aspect, the composition may comprise an enzyme stabilizer selected from the group consisting of (a) inorganic salts selected from the group consisting of calcium salts, magnesium salts and mixtures thereof; (b) carbohydrates selected from the group consisting of oligosaccharides, polysaccharides and mixtures thereof; (c) mass efficient reversible protease inhibitors selected from the group consisting of phenyl boronic acid and derivatives thereof; and (d) mixtures thereof.

In another embodiment, the composition comprises: (1) reversible protease inhibitors such as a boron containing compound; (2) 1-2 propane diol; (3) calcium formate and/or sodium formate; and (4) any combination thereof.

In one aspect, the composition may comprise a structurant selected from the group consisting of diglycerides and triglycerides, ethylene glycol distearate microcrystalline cellulose, cellulose-based materials, microfiber cellulose, biopolymers, xanthan gum, gellan gum, and mixtures thereof.

The detergent may comprise one or more polymers. Examples are carboxymethylcellulose, poly(vinyl-pyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as tetraacetylethylenediamine or nonanoyloxyben-zenesul-fonate. Alternatively, the bleaching system may comprise peroxyacids of, e.g., the amide, imide, or sulfone type. In general, when a bleaching agent is used, the compositions of the present invention may comprise from about 0.1% to about 50% or even from about 0.1% to about 25% bleaching agent by weight of the subject cleaning composition. The enzyme variants of the invention may be stabilized using conventional stabilizing agents or and protease inhibitors, e.g., a polyol such as propylene glycol or glycerol, a sugar or sugar alcohol, different salts such as NaCl and KCl; lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO 2009/118375, WO 98/13459) or a protease inhibitor of the protein type such as RASI, BASI, WASI (bifunctional alpha-amylase/subtilisin inhibitors of rice, barley and wheat) or C12 or SSI.

The composition may be formulated as described in, e.g., WO 92/19709 and WO 92/19708 or U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (Ill), Tin (II), cobalt (II), copper (II), Nickel (II), and oxovanadium (IV)).

The detergent may also contain other conventional detergent ingredients such as, e.g., fabric conditioners including clays, foam boosters, suds suppressors, anti-corrosion agents, soil-suspending agents, anti-soil re-deposition agents, dyes, bactericides, optical brighteners, hydrotropes, tarnish inhibitors, organic solvents such as ethanol, or perfumes. Furthermore, the detergent could contain a pre-spotter or a booster, which is added to the wash to increase the general cleaning level, some of these additives may also be used as a pre-treatment agent applied to the textile before the washing step.

It is at present contemplated that in the detergent compositions any enzyme, in particular the enzyme of the invention, may be added in an amount corresponding to 0.001-100 mg of enzyme protein per liter of wash liquor, preferably 0.005-5 mg of enzyme protein per liter of wash liquor, more preferably 0.01-1 mg of enzyme protein per liter of wash liquor and in particular 0.1-1 mg of enzyme protein per liter of wash liquor. However, the detergent compositions of the present invention comprise at least 0.0001 to about 0.1% weight percent of pure enzyme protein, such as from about 0.0001% to about 0.01%, from about 0.001% to about 0.01% or from about 0.001% to about 0.01%. However, when using a formulated enzyme the detergent composition comprises from about 0.02% to about 20% weight percent, such as or from about 0.05% to about 15% weight, or from about 0.05 to about 20%, or from about 0.05% to about 5%, or from about 0.05% to about 3%.

The alpha-amylase variants of the invention may additionally be incorporated in the detergent formulations disclosed in WO 97/07202, which is hereby incorporated as reference.

The composition typically comprises other detergent ingredients. Suitable detergent ingredients include: bleach; imine bleach boosters; sources of hydrogen peroxide such as percarbonate and/or perborate, especially percarbonate coated with material such as carbonate and/or sulphate salt, silicate salt, borosilicate, and any mixture thereof; pre-formed peracid, including pre-formed peracid in encapsulated form; transition metal catalysts; suds suppressing systems such as silicone based suds suppressors and/or fatty acid based suds suppressors; brighteners; photobleach; fabric-softening agents such as clay, silicone and/or quaternary ammonium compounds; flocculants such as polyethylene oxide; dye transfer inhibitors such as polyvinylpyrrolidone, poly 4-vinylpyridine N-oxide and/or co-polymer of vinylpyrrolidone and vinylimidazole; fabric integrity components such as oligomers produced by the condensation of imidazole and epichlorhydrin; soil dispersants and soil anti-redeposition aids such as alkoxylated polyamines and ethoxylated ethyleneimine polymers; anti-redeposition components such as polyesters; carboxylate polymers such as maleic acid polymers or co-polymers of maleic and acrylic acid; perfumes such as perfume microcapsules, starch encapsulated accords, perfume spray-on; soap rings; aesthetic particles; dyes; fillers such as sodium sulphate, although it is preferred for the composition to be substantially free of fillers; silicate salt such as sodium silicate, including 1.6R and 2.0R sodium silicate, or sodium metasilicate; co-polyesters of di-carboxylic acids and diols; cellulosic polymers such as methyl cellulose, carboxymethyl cellulose, hydroxyethoxycellulose, or other alkyl or alkylalkoxy cellulose; solvents such as 1,2 propanediol, monoethanolamine; diethylene glycol, ethanol, and any mixture thereof; hydrotropes such as sodium cumene sulphonate, sodium xylene sulphonate, sodium toluene sulphonate, and any mixtures; organic acids such as citric acid; and any combination thereof.

Example Laundry Detergent Composition

The following are liquid laundry detergent compositions suitable for top-loading automatic washing machines (1 and 2) and front-loading washing machines (3).

| Ingredient | Composition (wt % of composition) | | |
|---|---|---|---|
| | 1 | 2 | 3 |
| $C_{12-15}$ Alkylethoxy(1.8)sulfate | 14.7 | 11.6 | |
| $C_{11.8}$ Alkylbenzene sulfonate | 4.3 | 11.6 | 8.3 |
| $C_{16-17}$ Branched alkyl sulfate | 1.7 | 1.29 | |
| $C_{12-14}$ Alkyl-9-ethoxylate | 0.9 | 1.07 | |
| $C_{12}$ dimethylamine oxide | 0.6 | 0.64 | |
| Citric acid | 3.5 | 0.65 | 3 |
| $C_{12-18}$ fatty acid | 1.5 | 2.32 | 3.6 |
| Sodium Borate (Borax) | 2.5 | 2.46 | 1.2 |
| Sodium $C_{12-14}$ alkyl ethoxy 3 sulfate | | | 2.9 |
| $C_{14-15}$ alkyl 7-ethoxylate | | | 4.2 |
| $C_{12-14}$ Alkyl-7-ethoxylate | | | 1.7 |

-continued

| | Composition (wt % of composition) | | |
|---|---|---|---|
| Ingredient | 1 | 2 | 3 |
| Calcium formate | 0.09 | 0.09 | |
| A compound having the following general structure: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = from 20 to 30, and x = from 3 to 8, or sulphated or sulphonated variants thereof | | | 1.2 |
| Random graft co-polymer[1] | | 1.46 | 0.5 |
| Ethoxylated Polyethylenimine [2] | 1.5 | 1.29 | |
| Diethylene triamine pentaacetic acid | 0.34 | 0.64 | |
| Diethylene triamine penta(methylene phosphonic acid) | | | 0.3 |
| Tinopal AMS-GX | | 0.06 | |
| Tinopal CBS-X | 0.2 | 0.17 | |
| Amphiphilic alkoxylated grease cleaning polymer [3] | 1.28 | 1 | 0.4 |
| Ethanol | 2 | 1.58 | 1.6 |
| Propylene Glycol | 3.9 | 3.59 | 1.3 |
| Diethylene glycol | 1.05 | 1.54 | |
| Polyethylene glycol | 0.06 | 0.04 | |
| Monoethanolamine | 3.05 | 2.41 | 0.4 |
| NaOH | 2.44 | 1.8 | |
| Sodium Cumene Sulphonate | | | 1 |
| Sodium Formate | | 0.11 | |
| Water, Aesthetics (Dyes, perfumes) and Minors (Enzymes, solvents, structurants) | Balance | balance | balance |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

[2] Polyethylenimine (MW = 600) with 20 ethoxylate groups per —NH.

[3] Amphiphilic alkoxylated grease cleaning polymer is a polyethylenimine (MW = 600) with 24 ethoxylate groups per —NH and 16 propoxylate groups per —NH Compositions 4-8 Automatic Dishwashing Gels Compositions 4-8 Automatic Dishwashing Gels

| | 4 (wt %) | 5 (wt %) | 6 (wt %) | 7 (wt %) | 8 (wt %) |
|---|---|---|---|---|---|
| Wetting agent[1] | 1.0 | 1.3 | 0.8 | 1 | 0.9 |
| Sodium Benzoate (33% active) | 0.61 | 0.61 | 0.61 | 0.6 | 0.6 |
| Xanthan gum | 1.0 | 0.8 | 1.2 | 1 | 1.1 |
| Sodium Sulphate | 10.0 | 10.0 | 10.0 | 8 | 10 |
| Perfume | 0.03 | 0.05 | 0.03 | 0.06 | 0.1 |
| Sodium Silicate | 0 | 0 | 0 | 0 | 2 |
| Citric Acid (50% active) | 12.5 | 0 | 11 | 0 | 12 |
| GLDA | 0 | 7 | 0 | 8 | 0 |
| Savinase Ultra XL(44 mg active/g)[2] | 0.7 | 0 | 0.3 | 0 | 0 |
| 4-Formyl-Phenyl Boronic Acid | 0 | 0 | 0.05 | 0 | 0 |
| Encapsulated Protease (10 mg/g) [3] | 0.0 | 2.0 | 0.0 | 0 | 0 |
| FN3 liquid (48 mg active/g) [4] | 0.0 | 0.0 | 0 | 0.6 | 0 |
| Protease Prill (123 mg active/g) [4] | 0 | 0 | 0 | 0 | 0.5 |
| Ethanol | 0.0 | 0.0 | 0 | 0.3 | 0 |
| Potassium Hydroxide (45% active) | 14.6 | 14.6 | 14.6 | 14 | 0 |
| Calcium Chloride (25% active) | 1.8 | 1.8 | 1.8 | 1.1 | 0.4 |
| Dye | 0.05 | 0.05 | 0.05 | 0.05 | 0.02 |
| Proxcel GXL ™ (19% active) [8] | 0.05 | 0.05 | 0.05 | 0.05 | 0.05 |
| Acusol ™ 820[9] | 0.34 | 0.34 | 0.3 | 0.35 | 0.3 |

-continued

| Compositions 4-8 Automatic Dishwashing Gels | 4 (wt %) | 5 (wt %) | 6 (wt %) | 7 (wt %) | 8 (wt %) |
|---|---|---|---|---|---|
| Acusol ™ 425N (50% active) [9] | 3.0 | 3.0 | 3.5 | 2.5 | 2 |
| Amylases of this invention (25 mg/g active)[2] | 0.2 | 0.5 | 0.4 | 0.3 | 0.1 |
| Water & other adjunct ingredients | Balance to 100% | Balance to 100% | Balance to 100% | Balance to 100% | Balance to 100% |

[1]Sold under tradename Polytergent ® SLF-18 by BASF, Ludwigshafen, Germany.
[2]Sold by Novozymes A/S, Denmark.
[3] Encapsulated protease of this invention
[4] Sold by Genencor International, California, USA. Suitable protease prills are sold under the tradenames FN3R and Properase ®.
[6] Sold by Alco Chemical, Tennessee, USA.
[7] One such suitable polymer would be sold under the tradename Aqualic TL by Nippon Shokubai, Japan.
[8] Sold by Arch Chemicals Incorporated, Smyrna, Georgia, USA
[9]Sold by Rohm and Haas, Philadelphia, Pennsylvania, USA
2.0R Silicate is supplied by PQ Corporation, Malvern, PA, USA.
Sodium Carbonate is supplied by Solvay, Houston, Texas, USA
Sodium percarbonate ($2Na_2CO_3{\bullet}3H_2O_2$) supplied by Solvay, Houston, Texas, USA
Hydroxyethane di phosphonate (HEDP) is supplied by Dow Chemical, Midland, Michigan, USA Dishwash Detergent Compositions The enzyme of the invention may also be used in dish wash detergent compositions, including the following:

1) Powder Automatic Dishwashing Composition

| | |
|---|---|
| Nonionic surfactant | 0.4-2.5% |
| Sodium metasilicate | 0-20% |
| Sodium disilicate | 0-20% |
| Sodium triphosphate | 0-40% |
| Sodium carbonate | 0-20% |
| Sodium perborate | 2-9% |
| Tetraacetyl ethylene diamine (TAED) | 1-4% |
| Sodium sulfate | 5-33% |
| Enzymes | 0.0001-0.1% |

2) Powder Automatic Dishwashing Composition

| | |
|---|---|
| Nonionic surfactant (e.g., alcohol ethoxylate) | 1-2% |
| Sodium disilicate | 0-30% |
| Sodium carbonate | 10-50% |
| Sodium phosphonate | 0-5% |
| Trisodium citrate dehydrate | 0-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g., maleic acid/acrylic acid copolymer) | 6-25% |
| Enzymes | 0.0001-0.1% |
| Perfume | 0.1-0.5% |
| Water | 5-10 |

3) Powder Automatic Dishwashing Composition

| | |
|---|---|
| Nonionic surfactant | 0.5-2.0% |
| Sodium disilicate | 0-40% |
| Sodium citrate | 0-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 0-3% |
| Polyamino acids | 0-20% |
| Sodium polyacrylate | 0-8% |
| Enzymes | 0.0001-0.1% |

4) Powder Automatic Dishwashing Composition

| | |
|---|---|
| Nonionic surfactant | 1-2% |
| Zeolite MAP | 15-42% |
| Sodium disilicate | 0-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 0-2% |
| Enzymes | 0.0001-0.1% |
| Sodium sulfate | Balance |

5) Powder Automatic Dishwashing Composition

| | |
|---|---|
| Nonionic surfactant | 1-7% |
| Sodium disilicate | 0-30% |
| Trisodium citrate | 0-24% |
| Sodium carbonate | 12-20% |
| Monopersulfate (2 $KHSO_5{\bullet}KHSO_4{\bullet}K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulfate, water | Balance |

6) Powder and Liquid Dishwashing Composition with Cleaning Surfactant System

| | |
|---|---|
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dehydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |

-continued

| | |
|---|---|
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulfate | 0-12.5% |
| Enzymes | 0.0001-0.1% |

7) Non-Aqueous Liquid Automatic Dishwashing Composition

| | |
|---|---|
| Liquid nonionic surfactant (e.g., alcohol ethoxylates) | 2.0-10.0% |
| Alkali metal silicate | 0-15.0% |
| Alkali metal phosphate | 0-40.0% |
| Liquid carrier selected from higher glycols, polyglycols, polyoxides, glycolethers | 25.0-45.0% |
| Stabilizer (e.g., a partial ester of phosphoric acid and a $C_{16}$-$C_{18}$ alkanol) | 0.5-7.0% |
| Foam suppressor (e.g., silicone) | 0-1.5% |
| Enzymes | 0.0001-0.1% |

8) Non-Aqueous Liquid Dishwashing Composition

| | |
|---|---|
| Liquid nonionic surfactant (e.g., alcohol ethoxylates) | 2.0-10.0% |
| Sodium silicate | 0-15.0% |
| Alkali metal carbonate | 7.0-20.0% |
| Sodium citrate | 0-1.5% |
| Stabilizing system (e.g., mixtures of finely divided silicone and low molecular weight dialkyl polyglycol ethers) | 0.5-7.0% |
| Low molecule weight polyacrylate polymer | 5.0-15.0% |
| Clay gel thickener (e.g., bentonite) | 0-10.0% |
| Hydroxypropyl cellulose polymer | 0-0.6% |
| Enzymes | 0.0001-0.1% |
| Liquid carrier selected from higher lycols, polyglycols, polyoxides and glycol ethers | Balance |

9) Thixotropic Liquid Automatic Dishwashing Composition

| | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulfonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulfonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

10) Liquid Automatic Dishwashing Composition

| | |
|---|---|
| Alcohol ethoxylate | 0-20% |
| Fatty acid ester sulfonate | 0-30% |

-continued

| | |
|---|---|
| Sodium dodecyl sulfate | 0-20% |
| Alkyl polyglycoside | 0-21% |
| Oleic acid | 0-10% |
| Sodium disilicate monohydrate | 0-33% |
| Sodium citrate dehydrate | 0-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

11) Liquid Automatic Dishwashing Composition Containing Protected Bleach particles

| | |
|---|---|
| Sodium silicate | 5-10% |
| Tetrapotassium pyrophosphate | 0-25% |
| Sodium triphosphate | 0-2% |
| Potassium carbonate | 4-8% |
| Protected bleach particles, e.g., chlorine | 5-10% |
| Polymeric thickener | 0.7-1.5% |
| Potassium hydroxide | 0-2% |
| Enzymes | 0.0001-0.1% |
| Water | Balance |

12) Automatic dishwashing compositions as described in 1), 2), 3), 4), 6) and 10), wherein perborate is replaced by percarbonate.

13) Automatic dishwashing compositions as described in 1)-6) which additionally contain a manganese catalyst. The manganese catalyst may, e.g., be one of the compounds described in "Efficient manganese catalysts for low-temperature bleaching", *Nature* 369: 637-639 (1994).

INDUSTRIAL APPLICATION

The present invention is also directed to methods for using the alpha-amylase variants.

The variant alpha-amylase are preferably incorporated into and/or used together with detergent compositions, for example in laundry detergent compositions, for example household laundry detergent compositions, especially liquid laundry detergent compositions. In particular the detergent comprises at least one chelating agent and the detergent composition typically comprises conventional detergent ingredients such as surfactants (anionic, cationic, nonionic, zwitterionic, amphoteric), builders, bleaches, polymers, other enzymes and other ingredients, e.g., as described in WO 2007/130562 and WO 2007/149806, which are hereby incorporated by reference in its entirety.

Owing to their activity at alkaline pH values, the α-amylases of the invention are well suited for use in a variety of industrial processes, in particular the enzyme finds potential applications as a component in washing, dishwashing and hard surface cleaning detergent compositions, but it may also be useful in the production of sweeteners, syrup such as glucose and the like, plastic precursors, a fermentation product, especially ethanol, butanol and methanol, and biogas such as methane or any other product originating from starch. Conditions for conventional starch-converting processes and liquefaction and/or saccharification processes are described in, for instance, U.S. Pat. No. 3,912,590 and EP patent publications Nos. EP 252,730 and EP 63,909.

The alpha-amylase variants of the invention may also be used in the production of lignocellulosic materials, such as pulp, paper and cardboard, from starch reinforced waste paper and cardboard, especially where repulping occurs at pH above 7 and where amylases can facilitate the disintegration of the waste material through degradation of the reinforcing starch. The alpha-amylase variants of the invention may also be useful in modifying starch where enzymatically modified starch is used in papermaking together with alkaline fillers such as calcium carbonate, kaolin and clays.

Thus, the above described compositions may further comprise non-detergent components, a fermenting organism such as, e.g., yeast preferably a strain of *Saccharomyces*, a plant material or starch-containing material such as, e.g., tubers, roots, stems, whole grains, corns, cobs, wheat, barley, rye, milo, sago, cassava, tapioca, sorghum, rice peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof.

The alpha-amylase variants of the invention may also be useful in textile desizing. In the textile processing industry, alpha-amylases are traditionally used as auxiliaries in the desizing process to facilitate the removal of starch-containing size which has served as a protective coating on weft yarns during weaving.

Complete removal of the size coating after weaving is important to ensure optimum results in the subsequent processes, in which the fabric is scoured, bleached and dyed. Enzymatic starch break-down is preferred because it does not involve any harmful effect on the fibre material.

In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size does lead to some fibre damage because of the rather aggressive chemicals used.

Accordingly, it would be desirable to use the alpha-amylase variants of the invention as they have an improved performance in alkaline solutions. The alpha-amylase variants may be used alone or in combination with a cellulase when desizing cellulose-containing fabric or textile.

In one embodiment, the present invention relates to products for and/or methods relating to and/or use of the claimed compositions that are not for air care. In one embodiment, the present invention relates to products for and/or methods relating to and/or use of the claimed compositions that are not for car care. In one embodiment, the present invention relates to products for and/or methods relating to and/or use of the claimed compositions that are not for dishwashing. In one embodiment, the present invention relates to products for and/or methods relating to and/or use of the claimed compositions that are not for fabric conditioning (including softening). In one embodiment, the present invention relates to products for and/or methods relating to and/or use of the claimed compositions that are not for laundry detergency. In one embodiment, the present invention relates to products for and/or methods relating to and/or use of the claimed compositions that are not for laundry and rinse additive and/or care. In one embodiment, the present invention relates to products for and/or methods relating to and/or use of the claimed compositions that are not for hard surface cleaning and/or treatment and other cleaning for consumer or institutional use. In one embodiment, the present invention relates to products for and/or methods relating to and/or use of the claimed compositions that are not for air care, car care, dishwashing, fabric conditioning (including softening), laundry detergency, laundry and rinse additive and/or care, hard surface cleaning and/or treatment, and other cleaning for consumer or institutional use.

Materials and Methods

Enzymes:

SP722: SEQ ID NO: 6, available from Novozymes, and disclosed in WO 95/26397.

SP707 or #707: SEQ ID NO: 8

AA560: SEQ ID NO: 10

General Molecular Biology Methods:

Unless otherwise mentioned the DNA manipulations and transformations were performed using standard methods of molecular biology (Sambrook et al. (1989); Ausubel et al. (1995); *Harwood and Cutting* (1990).

Fermentation of Alpha-Amylases and Variants

Fermentation may be performed by methods well known in the art or as follows. A *B. subtilis* strain harboring the relevant expression plasmid is streaked on a LB-agar plate with a relevant antibiotic, and grown overnight at 37° C.

The colonies are transferred to 100 ml BPX media supplemented with a relevant antibiotic (for instance 10 mg/l chloroamphinicol) in a 500 ml shaking flask.

Composition of BPX Medium:

| | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| $Na_2HPO_4$, 12 $H_2O$ | 9 g/l |
| Antifoaming agent | 0.1 g/l |

The culture is shaken at 37° C. at 270 rpm for 4 to 5 days.

Cells and cell debris are removed from the fermentation broth by centrifugation at 4500 rpm in 20-25 minutes. Afterwards the supernatant is filtered to obtain a completely clear solution. The filtrate is concentrated and washed on an UF-filter (10000 cut off membrane) and the buffer is changed to 20 mM Acetate pH 5.5, e.g., by dialysis or gelfiltration. The UF-filtrate is applied on a S-sepharose F.F. (General Electric, Cation exchange, Matrix: Cross-linked agarose, functional group: $—OCH_2CHOHCH_2OCH_2CH_2CH_2SO_3$) and elution is carried out by step elution with 0.2 M NaCl in the same buffer. The eluate is dialysed against 10 mM Tris (2-amino-2-hydroxymethyl-propane-1,3-diol), pH 9.0 and applied on a Q-sepharose F.F. (General Electric, anion exchange, Matrix: cross-linked agarose, functional group: $—OCH_2CHOHCH_2OCH_2CHOHCH_2N+(CH_3)_3$), and eluted with a linear gradient from 0-0.3 M NaCl over 6 column volumes. The fractions, which contain the activity (measured by the EnzCheck assay) are pooled, pH is adjusted to pH 7.5 and remaining color is removed by a treatment with 0.5% w/vol. active coal in 5 minutes. It may further be advantageous to add a further buffer exchange step, e.g., by dialysis or gelfiltration to a buffer system that does not affect the wash result in itself, e.g., to an EPPS-buffer, a glycine-buffer, an acetate buffer or the like, preferably with a small concentration of calcium (e.g., 0.1 mM) to stabilize the amylase during storage and about 0.01% TRITON™ X-100 to reduce risk of adsorption of enzyme protein to containers and pipettes.

Model Detergent

Composition of Model Detergent A:

| Compound | Amount g/100 g | % active ingredient |
|---|---|---|
| | Surfactants | |
| Na-LAS (92%) (Nacconol 90 G) (anionic) (linear alkylbenzene sulfonate) | 10.87 | 10 |
| STEOL CS-370E (70%) (anionic), $CH_3(CH_2)_m$—$(OCH_2CH_2)_3$—$OSO_3$—, where m = 11-13 | 7.14 | 5 |
| Bio-soft N25-7 (99.5%) (non-ionic): $CH_3(CH_2)_m$—$(OCH_2CH_2)_7$—OH, where and m = 11-14 | 5 | 5 |
| Oleic acid (fatty acid) | 2 | 2 |
| | Solvents | |
| $H_2O$ | 62 | 65 |
| Ethanol | 0.5 | 0.5 |
| STS (sodium p-toluene sulfonate (40%)) | 3.75 | 1.5 |
| Mono propylene glycol | 2 | 2 |
| | Builder | |
| Tri-sodium-citrate | 4 | 4 |
| Triethanolamine (TEA) | 0.5 | 0.5 |
| | Stabilizer | |
| Boric acid | 1.5 | 1.5 |
| | Minors | |
| 10N NaOH (for adjustment to pH 8.5) | 0.8 | 0.8 |

Composition of Model Detergent B:

| Compound | Amount g/100 g | % active ingredient |
|---|---|---|
| | Surfactants | |
| Na-LAS (92%) (Nacconol 90G) (anionic) | 10.87 | 10 |
| STEOL CS-370E (70%) (anionic) | 7.14 | 5 |
| Bio-soft N25-7 (99.5%) (non-ionic) | 5 | 5 |
| Oleic acid (fatty acid) | 2 | 2 |
| | Solvents | |
| $H_2O$ | 62 | 65 |
| Ethanol | 0.5 | 0.5 |
| STS (sodium p-toluene sulfonate (40%) | 3.75 | 1.5 |
| Mono propylene glycol | 2 | 2 |
| | Builder | |
| Diethylene triamine penta acetic acid (DTPA) | 1.5 | 1.5 |
| Triethanolamine (TEA) | 0.5 | 0.5 |
| | Stabilizer | |
| Boric acid | 1.5 | 1.5 |
| | Minors | |
| 10N NaOH (for adjustment to pH 8.0) | 0.8 | 0.8 |

Assay for Measurement of Free Calcium Ions

The following assay may be used for the measurement of free calcium ions in solution, and thus for the determination of chelating agents (chelants) ability to reduce the concentration of free calcium ions ($Ca^{2+}$) from, e.g., 2.0 mM to 0.10 mM at pH 8.

Assay Principle:

Various amounts of chelants are added to a solution of 2.0 mM $Ca^{2+}$ and the free $Ca^{2+}$ concentration is determined by using a Calcium Ion Selective Electrode at fixed pH and temperature. The concentration of chelant necessary to reduce the concentration of free calcium from 2.0 mM to 0.10 mM can be determined from a plot of the free calcium concentration measured versus the concentration of chelant.

In the present assay the concentration of chelant necessary to reduce the concentration of free calcium from 2.0 mM to 0.10 mM is measured at pH 8, at 21° C., in potassium chloride and 49 mM EPPS.

Solutions:

Electrolyte solution: 4 M potassium chloride in ultrapure water (Milli-Q water).

pH 8 buffer: 50 mM EPPS (4-(2-Hydroxyethyl)piperazine-1-propanesulfonic acid) adjusted to pH 8.0 using minimum amounts of 1 N sodium hydroxide.

Calcium stock solution: 25 mM $Ca^{2+}$ in pH 8 buffer, made from $CaCl_2 \cdot 2H_2O$.

Chelant stock solution: 15 mM chelant (on a 100% dry chelator basis) in pH 8 buffer, re-adjusted to pH 8.0 using minimum amounts of 1 M NaOH or 1 M HCl.

Ultra pure water (Milli Q water) is used for preparation of all buffers and solutions.

Equipment:

Calcium Ion Selective Electrode from Thermo Scientific (cat. No. 9720BNWP) calibrated against a Calcium chloride standard solution. The electrode is calibrated as described by the guidelines following the electrode.

Procedure:

A series of vials are prepared, each containing 4 mL of the calcium stock solution (final concentration 2.0 mM), 1 mL electrolyte solution (final concentration 80 mM potassium chloride), chelant stock solution in various amounts (0-45 mL) and using the pH 8 buffer for adjusting the total volume to 50 mL. The final concentration of EPPS in the assay is 49 mM.

After mixing, the concentration of free $Ca^{2+}$ is measured by the calcium electrode. The free calcium concentration should be determined at a sufficient number of different chelant concentrations for each chelant tested, ensuring that the data set covers the entire range from 2.0 mM free calcium ions to a value below 0.10 mM or the final chelant concentration in the assay is higher than 10.0 mM. A suitable number of data points are 8 or more. The chelant concentration required to lower the initial 2.0 mM free calcium ions to 0.10 mM is obtained from a plot of the measured free calcium ion concentration versus chelator concentration by interpolation.

The solutions are equilibrated to the desired temperature, which in the present assay is 21° C.

Determination of Log K

Chelating agents can also be characterized by the binding constant of the chelating agent (chelator) and calcium ions. This constant can be determined by ITC (isothermal titration calorimetry) as described by Nielsen et al., 2003, *Analytical Biochemistry* 314: 227-234 and Wiseman et al., 1989, *Analytical Biochemistry* 179: 131-137.

All glassware and plastic bottles used are washed with a 1% (w/w) EDTA solution and subsequently rinsed thoroughly in Chelex 100 treated ultrapure water (Milli-Q water). Solutions are stored in plastic bottles and kept at 5° C. until use.

Buffers:

20 mM HEPES (2-[4-(2-hydroxyethyl)-1-piperazinyl]-ethanesulfonic acid), pH 8 prepared with ultrapure water (Milli-Q water)

20 mM glycine, pH 10 prepared with ultrapure water (Milli-Q water)

Solutions:

125 μM chelant in 20 mM HEPES, pH 8 or 125 μM chelant in 20 mM glycine, pH 10

4 mM $CaCl_2$ in 20 mM HEPES, pH 8 or 4 mM $CaCl_2$ in 20 mM glycine, pH 10

Ultrapure water (Milli-Q water)

All buffers are passed through Chelex 100 columns (Sigma Aldrich C-7901, matrix 1% cross-linked polystyrene matrix active group iminodiacetic acid (sodium form) matrix attachment through methyl group to aromatic rings) to remove calcium ions. All solutions are degassed by stirring under vacuum before the experiments.

Instrument:

MCS-ITC (MicroCal Inc., Northampton, MA, USA)

Procedure

The reference cell is filled with ultrapure water (Milli-Q water). The sample cell is filled with the chelant solution at the selected pH and the syringe is filled with the calcium solution at the selected pH. The solutions are equilibrated to the desired temperature, e.g., 19° C.

The chelator solution in the sample cell is then titrated with 30-40 aliquots of 8 μL of the calcium solution.

The obtained signals from the ITC are then integrated using the Origin software supplied by MicroCal Inc. To obtain the binding isotherms, regression routines are made using the same software package. These data are then fitted to a model using the routines embedded in the Origin software. Presently preferred is the "OneSites" model which gives the best fit for most of the commonly used chelating agents, i.e., the residuals are evenly distributed around zero. From the K value the log K is calculated as the logarithm (base 10) of the K value.

Assays for Determining Wash Performance

In order to assess the wash performance of the alpha-amylase variants in a detergent composition, washing experiments may be performed. The enzymes are tested using the Automatic Mechanical Stress Assay (AMSA) or the wash performing test using beakers. With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress in a regular, periodic oscillating manner. For further description see WO 02/42740, especially the paragraph "Special method embodiments" at page 23-24.

General Wash Performance Description:

A test solution comprising water (15° dH), 0.8 g/L detergent, e.g., model detergent A or B as described above, or 50 mM HCO3−, and the enzyme of the invention, e.g., at concentration of 0, 0.2, 0.4, 0.8 and/or 1.2 mg enzyme protein/L, is prepared. Fabrics stained with starch (e.g., CS-28 from Center For Testmaterials BV, P.O. Box 120, 3133 KT, Vlaardingen, The Netherlands) is added and washed for 30 minutes at 20° C. After thorough rinse under running tap water and drying in the dark, the light intensity or reflectance values of the stained fabrics are subsequently measured as a measure for wash performance. The test with 0 mg enzyme protein/L is used as a blank to obtain a delta remission value. Preferably mechanical action is applied during the wash step, e.g., in the form of shaking, rotating or stirring the wash solution with the fabrics.

The AMSA wash performance experiments may be conducted under the experimental conditions specified below:

| Detergent | Model detergent A or B |
|---|---|
| Detergent dosage | 0.8 g/L |
| Test solution volume | 160 micro L |
| pH | As is |
| Wash time | 30 minutes |
| Temperature | 20° C. |
| Water hardness | 15° dH |
| Enzyme concentration in test solution | 0; 0.2; 0.4; 0.8; 1.2 mg/L |
| Test material | CS-28 (Rice starch on cotton) |

Water hardness was adjusted to 15° dH by addition of $CaCl_2$, $MgCl_2$, and $NaHCO_3$ ($Ca^{2+}$:$Mg^{2+}$:$HCO_3^-$=4:1:7.5, molar basis) to the test system. After washing the textiles were flushed in tap water and dried in the dark.

The performance of the enzyme variant is measured as the brightness of the color of the textile washed with that specific amylase. Brightness can also be expressed as the intensity of the light reflected from the sample when illuminated with white light. When the sample is stained the intensity of the reflected light is lower, than that of a clean sample. Therefore, the intensity of the reflected light can be used to measure wash performance of an amylase.

Color measurements are made with a professional flatbed scanner (Kodak iQsmart, Kodak), which is used to capture an image of the washed textile.

To extract a value for the light intensity from the scanned images, 24-bit pixel values from the image are converted into values for red (r), green (g) and blue (b), also known as RGB value.

The intensity value (Int) is calculated by adding the RGB values together as vectors and then taking the length of the resulting vector:

$$Int=\sqrt{r^2+g^2+b^2}.$$

Textiles: Textiles sample CS-28 (rice starch on cotton) can be obtained from Center For Test materials BV, P.O. Box 120, 3133 KT Vlaardingen, the Netherlands.

The wash performance test using beakers is an assay in a small scale model of a top loaded washing machine and used to evaluate the washing performance of amylases. The beaker wash performance test, using 250 mL beakers and a paddle stirrer providing oscillating rotational motion, 180° in each direction, with a frequency of 80 per minute, comprises the following steps: providing 100 mL wash solution (6° C., 15° dH, pH 8.0) containing 50 mM $NaHCO_3$ and 0.4 mg/L enzyme; adding two swatches of CS-28 (5×5 cm) and two swatches of EMPA 162 (5×5 cm) to the wash solution to start the wash; setting the agitation speed to 80 rpm; stopping the agitation after 60 minutes, rinsing the swatches under cold running tap water; drying the rinsed swatches in the dark over night; and evaluating the wash performance by measuring the remission of incident light at 460 nm using Color Eye as described below.

Equipment and Materials

Water bath (5° C.) with circulation; glass beakers (250 mL); one rotating arm per beaker with capacity of 100 mL of washing solution; test swatches: CS-28 (rice starch on cotton) from Center for Testmaterials BV, Vlaardingen, The Netherlands and EMPA 162 (rice starch on cotton/polyester) from EMPA Testmaterials AG, St. Gallen, Switzerland, the swatches are cut into 5×5 cm.

Wash solution: 50 mM $NaHCO_3$ buffer, pH 8.0, water hardness: 15° dH, Calcium:Magnesium ratio 4:1.

Amylase stock solution: 1 mg enzyme protein per mL. A solution of 0.1% (w/v) Triton™ X-100 (2-[4-(2,4,4-trimethylpentan-2-yl)phenoxylethanol) and 0.1 mM $CaCl_2$) in ultrapure water (MilliQ water) is used for dilution of amylase (amylase dilution buffer).

Color Eye Measurement

Wash performance is expressed as a delta remission value (ΔRem). Light reflectance evaluations of the swatches were done using a Macbeth Color Eye 7000 reflectance spectrophotometer with very small oval aperture, i.e., 0.7 $cm^2$ (~0.7×1.0 cm). The measurements were made without UV in the incident light and remission at 460 nm was extracted. The swatch to be measured was placed on top of another swatch of the same type before being measured to reduce reflection from the piston pushing the swatch up against the measuring opening. Delta remission values for individual swatches were calculated by subtracting the remission value of the swatch washed without added amylase (control) from the remission value of the swatch washed with amylase.

Assays for Measurement of Amylolytic Activity (Alpha-Amylase Activity)

EnzCheck Assay

The amylase activity or residual amylase activity can be determined by the following EnzCheck assay. The substrate is a corn starch derivative, DQ™ starch (corn starch BODIPY FL conjugate), which is corn starch labeled with BODIPY® FL (4,4-difluoro-5,7-dimethyl-4-bora-3a,4a-diaza-s-indacene-3-propionic acid) dye to such a degree that the fluorescence is quenched. One vial containing approx. 1 mg lyophilized substrate is dissolved in 100 μL 50 mM sodium acetate pH 4.0. The vial is vortexed for 20 seconds and left at room temperature, in the dark, with occasional mixing until dissolved. Then 950 μL 10 mM sodium acetate, 0.01% (w/V) TRITON™ X100 ((polyethylene glycol p-(1,1,3,3-tetramethylbutyl)-phenyl ether ($C_{14}H_{22}O(C_2H_4O)_n$ (n=9-10)), pH 5.0 is added, vortexed thoroughly and stored at room temperature, in the dark until ready to use. From 1 mL of this solution, the substrate working solution was prepared by mixing with 5 mL 50 mM HEPES, 0.01% (w/V) TRITON™ X100, 1 mM $CaCl_2$, pH 7.0.

The enzyme containing detergent is diluted to a concentration of 15 ng enzyme protein/ml (6826.7 times dilution) in 50 mM HEPES, 0.01% TRITON™ X100, 1 mM $CaCl_2$, pH 7.0.

For the assay, 25 μL of the substrate working solution is mixed for 10 second with 25 μL of the diluted enzyme in a black 384 well microtiter plate. The fluorescence intensity is measured (excitation: 485 nm, emission: 555 nm) once every second minute for 30 minutes in each well at 25° C. and the $V_{max}$ is calculated as the slope of the plot of fluorescence intensity against time. The plot should be linear and the residual activity assay has to been adjusted so that the diluted reference enzyme solution is within the linear range of the activity assay.

In a few instances there is a significant interference from the detergent without amylase on the assay. In such cases alternative amylase assays can be used. Interference from a detergent on an amylase assay can be tested by adding a known amount of amylase to the detergent at two levels and then measure the activity of the two samples. If the difference in the measured activities corresponds to the differences in the levels between the added amylases, the assay can be used to determine the residual activity of the amylase after storage.

PNP-G7 Assay

The alpha-amylase activity may be determined by a method employing the PNP-G7 substrate. PNP-G7 which is an abbreviation for 4,6-ethylidene($G_7$)-p-nitrophenyl($G_1$)-α, D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm). Kits containing PNP-G7 substrate and alpha-Glucosidase is manufactured by Roche/Hitachi (cat. No. 11876473).

Reagents:

The G7-PNP substrate from this kit contains 22 mM 4,6-ethylidene-G7-PNP and 52.4 mM HEPES (2-[4-(2-hydroxyethyl)-1-piperazinyl]-ethanesulfonic acid), pH 7.0).

The alpha-glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-PNP substrate. This substrate working solution is made immediately before use.

Dilution buffer: 50 mM EPPS, 0.01% (w/v) TRITON™ X100 (polyethylene glycol p-(1,1,3,3-tetramethylbutyl)-phenyl ether ($C_{14}H_{22}O(C_2H_4O)_n$ (n=9-10))), 1 mM $CaCl_2$, pH 7.0.

Procedure:

The amylase sample to be analyzed was diluted in dilution buffer to ensure the pH in the diluted sample is 7. The assay was performed by transferring 20 μl diluted enzyme samples to 96 well microtiter plate and adding 80 μl substrate working solution. The solution was mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Determination of Percentage Point (Pp)

The percentage point (pp) improvement in residual activity (stability) of the variant relative to the parent is calculated as the difference between the residual activity of the variant and the residual activity of the parent, i.e., the residual activity of the variant minus the residual activity of the parent.

EXAMPLES

Example 1: Preparation of Variants

The amylase variants of SEQ ID NO: 6 (SP722) were prepared by standard procedures, in brief: Introducing random and/or site-directed mutations into the gene, transforming *Bacillus subtilis* host cells with the mutated genes, fermenting the transformed host cells (e.g., as described in Example 1 of WO 2004/111220), and purifying the amylase from the fermentation broth. The reference amylase (SEQ ID NO: 6) was produced recombinantly in *Bacillus subtilis* in a similar manner.

Example 2: Characterization of Chelating Agents

Example 2a

Measure of Free Calcium Ions

Chelating agents (chelants) may be ranked by their ability to reduce the concentration of free calcium ions ($Ca^{21}$) from 2.0 mM to 0.10 mM at pH 8 developed from a method described by Nagarajan et al., 1984, *JAOCS* 61(9): 1475-1478. The assay is described above under "Materials and Methods" for measuring of free calcium ions was used. Accordingly, the concentration of chelant necessary to reduce the water hardness from 2.0 mM to 0.10 mM was determined as described above. The experiment was carried out with the pH 8 buffer at 21° C.

The final concentrations of chelant used and the free $Ca^{2+}$ concentration measured are shown in table 2.1 below.

TABLE 2.1

Concentration of free $Ca^{2+}$ determined in a mixture of 2.0 mM $Ca^{2+}$ and various amounts of chelating agent at pH 8.

| mL Calcium stock solution | mL electrolyte solution | mL pH 8 buffer | mL chelant | mM chelant final concentration |
|---|---|---|---|---|
| 4 | 1 | 45.0 | 0.0 | 0.00 |
| 4 | 1 | 44.0 | 1.0 | 0.30 |
| 4 | 1 | 43.0 | 2.0 | 0.60 |
| 4 | 1 | 41.0 | 4.0 | 1.20 |
| 4 | 1 | 39.0 | 6.0 | 1.80 |
| 4 | 1 | 38.5 | 6.5 | 1.95 |
| 4 | 1 | 38.0 | 7.0 | 2.10 |
| 4 | 1 | 37.5 | 7.5 | 2.25 |
| 4 | 1 | 37.0 | 8.0 | 2.40 |
| 4 | 1 | 36.5 | 8.5 | 2.55 |
| 4 | 1 | 36.0 | 9.0 | 2.70 |
| 4 | 1 | 35.5 | 9.5 | 2.85 |
| 4 | 1 | 35.0 | 10.0 | 3.00 |
| 4 | 1 | 32.5 | 12.5 | 3.75 |
| 4 | 1 | 30.0 | 15.0 | 4.50 |
| 4 | 1 | 25.0 | 20.0 | 6.00 |
| 4 | 1 | 20.0 | 25.0 | 7.50 |
| 4 | 1 | 15.0 | 30.0 | 9.00 |
| 4 | 1 | 10.0 | 35.0 | 10.50 |

From these data, the concentration of chelating agent necessary to reduce the free $Ca^{2+}$ concentration from 2.0 mM to below 0.10 mM were determined by interpolation.

A number of chelants were characterized using this assay and the chelator concentrations necessary to reduce the concentration of free calcium ions from 2.0 mM to 0.10 mM at pH 8.0 in 49 mM EPPS buffer and 80 mM potassium chloride are shown in Table 2.2.

TABLE 2.2

| | mM | Relative to citrate |
|---|---|---|
| Citrate | 8.36 | 1.00 |
| EGTA | 2.60 | 0.33 |
| EDTA | 1.90 | 0.21 |
| HEDP | 1.60 | 0.20 |
| DTPA | 1.87 | 0.24 |
| DTPMP | 1.17 | 0.15 |
| MGDA | 2.56 | 0.33 |

Example 2b

Determination of Log K

Alternatively, the chelating agents can be characterized by the binding constant of the chelating agent (chelator) and calcium ions. This constant can be determined by ITO (isothermal titration calorimetry) as described by Nielsen et al., 2003, *Analytical Biochemistry* 314: 227-234 and Wiseman et al., 1989, *Analytical Biochemistry* 179: 131-137. The procedure for the determination of log K is described in detail above under "Materials and Methods".

Using this procedure for determination of log K, the following log K values for several chelating agents were determined at pH 10 (Table 2.3).

TABLE 2.3

| | Log K | Log K relative to log K for citrate |
|---|---|---|
| Citrate | 3 | 1.00 |
| EGTA | 9 | 3.0 |
| EDTA | 8 | 2.7 |

TABLE 2.3-continued

| | Log K | Log K relative to log K for citrate |
|---|---|---|
| HEDP | 6 | 2.0 |
| DTPA | 7 | 2.7 |
| MGDA | 5 | 1.3 |

Example 3: Residual Activity after Incubation with Chelating Agent

EnzChek Assay

The amylase activity or residual amylase activity is in the present invention determined by the EnzCheck assay as described above. In general the residual amylase activity in model detergent B was determined after incubation at 31° C. for 18 hours the activity was then compared to the activity of a reference incubated at 4° C. for 18 hours as described above.

Test of the Stability of Amylase Variants in Detergent with 1.5% DTPA as Chelant For the determination of the amylase stability in detergent the enzymes to be tested were adjusted to a concentration of 0.6 mg/ml of enzyme protein by dilution in 20 mM HEPES, 0.1% (w/V) Triton™ X-100 (2-[4-(2,4,4-trimethylpentan-2-yl)phenoxy]ethanol), pH 8.0. If the starting amylase concentration is too low, it can be concentrated, by ultra filtration (UF) using a UF membrane with a cut off of 10 kDa.

25 μL of the amylase solution and 125 μL detergent (model detergent B) were transferred to a 96 well microtiter plate in 4 replicates. One small magnet (5×2 mm) was placed in each well, and the blend was mixed for 5 minutes at room temperature on a magnetic stirrer. Two identical plates were prepared. One of the plates was incubated at 4° C. for 18 hours (reference sample) and the other plate was incubated at 31° C. for 18 hours (31° C. sample).

Immediately after incubation, the samples on the plates were analyzed for amylase activity as described in the EnzCheck Assay for determination of residual amylase activity in detergents. It should be noted that in order to reduce interference from other detergent ingredients than the enzyme on the assay, both reference and 31° C. sample were diluted to the same protein concentration. The activity of both the reference samples and the 31° C. samples were determined on same 384-well plate. It was ensured that the reference amylase was included on all test microtiter plates The residual activity was calculated as 100*$V_{max}$ (31° C. sample)/$V_{max}$ (reference sample).

The result is shown in Table 3.1 using either SP722 or SP722+D183* G184* as reference amylase (parent). The percentage point (pp) improvement in residual activity of the variant relative to the parent is calculated as the difference between the residual activity of the variant and that of the parent.

TABLE 3.1

| | Residual activity (%) | pp improvement in residual activity relative to parent | |
|---|---|---|---|
| Enzyme | | SP722 | SP722 + D183* G184* |
| SP722 (parent) | 12 | 0 | — |
| SP722 + D183* G184* (parent) | 65 | 53 | 0 |
| SP722 + D183* G184* N195F | 88 | 76 | 23 |
| SP722 + D183* G184* N195L | 79 | 67 | 14 |
| SP722 + D183* G184* N197F | 95 | 83 | 30 |
| SP722 + D183* G184* N197L | 81 | 69 | 16 |
| SP722 + D183* G184* Y243F | 80 | 68 | 15 |
| SP722 + D183* G184* A186R, N195F | 79 | 67 | 14 |
| SP722 + D183* G184* H210Y | 74 | 62 | 9 |
| SP722 + D183* G184* V206L | 91 | 79 | 26 |
| SP722 + D183* G184* V213A | 87 | 75 | 22 |
| SP722 + Q174R D183* G184* E212V | 83 | 71 | 18 |
| SP722 + D183* G184* V206L E212G G304V A447V | 80 | 68 | 15 |
| SP722 + N116T G133E K142R D183* G184*Y198N V206L | 90 | 78 | 25 |
| SP722 + G133E D183* G184* N195Y Y198N Y200F | 83 | 71 | 18 |
| SP722 + N116T D183* G184* N195Y Y198N | 79 | 67 | 14 |
| SP722 + K142R P146S G149K D183* G184* N195Y Y198N V206I | 80 | 68 | 15 |
| SP722 + D134Y D183* G184* | 72 | 60 | 7 |
| SP722 + T151R D183* G184* H210Y K320N R359I N418D | 78 | 66 | 13 |
| SP722 + G147E G149R Q169E D183* G184* Y198N Y203F V206L | 87 | 75 | 22 |
| SP722 + G133E G149R D183* G184* N195Y Y198N Y203F V206L | 91 | 79 | 26 |
| SP722 + G147E Y152H Q169E D183* G184* Y198N V206L | 90 | 78 | 25 |
| SP722 + D183* G184* N195F V206L | 98 | 86 | 33 |
| SP722 + D183* G184* N195F Y243F | 100 | 88 | 35 |
| SP722 + D183* G184* N195F H210Y | 93 | 81 | 28 |
| SP722 + D183* G184* V206L H210Y | 95 | 83 | 30 |
| SP722 + D183* G184* V213A | 93 | 81 | 28 |
| SP722 + D183* G184* S193T | 85 | 73 | 20 |
| SP722 + D183* G184* A186T N195F | 96 | 84 | 31 |
| SP722 + D183* G184* N195F V206L Y243F | 94 | 82 | 29 |
| SP722 + D183* G184* V206L Y243F | 98 | 86 | 33 |

TABLE 3.1-continued

| | Residual activity (%) | pp improvement in residual activity relative to parent | |
|---|---|---|---|
| SP722 + D183* G184* N195Y | 93 | 81 | 28 |
| SP722 + G133D G149R D183* G184* Y198N V206L | 92 | 80 | 27 |
| SP722 + N116T G133E G147E Y152H D183* G184* Y198N Y203F V206L | 94 | 82 | 29 |
| SP722 + G147E G149R D183* G184* N195F Y198N V206L | 96 | 84 | 31 |
| SP722 + G133E K142R D183* G184* N195F Y198N | 95 | 83 | 30 |
| SP722 + G133E G149R Y152H D183* G184* N195Y Y198N V206L | 97 | 85 | 32 |
| SP722 + N116T Q129L K142R D183* G184* N195Y Y198N Y203F V206L | 101 | 89 | 36 |
| SP722 + G133E G149R Y152H D183* G184* N195Y Y198N Y203F V206L | 101 | 89 | 36 |
| SP722 + N116T G133E G149R D183* G184*Y198N Y203F V206L | 104 | 92 | 39 |
| SP722 + D183* G184* N195F V206Y Y243F | 109 | 97 | 44 |
| SP722 + D183* G184* N195F V206C Y243F | 113 | 101 | 48 |
| SP722 + D183* G184* N195F V206T Y243F | 109 | 97 | 44 |
| SP722 + D183* G184* N195F V206N Y243F | 99 | 87 | 34 |
| SP722 + D183* G184* N195F V206C | 101 | 89 | 36 |
| SP722 + D183* G184* N195F V206H | 105 | 93 | 40 |
| SP722 + D183* G184* N195F V206Y | 110 | 98 | 45 |
| SP722 + D183* G184* N195F V206L | 111 | 99 | 46 |
| SP722 + D183* G184* N195F V206G Y243F | 104 | 92 | 39 |
| SP722 + D183* G184* V206F Y243F | 104 | 92 | 39 |
| SP722 + D183* G184* N195F V206I Y243F | 105 | 93 | 40 |
| SP722 + D183* G184* N195F V206F Y243F | 92 | 80 | 27 |
| SP722 + D183* G184* N195F V206S Y243F | 104 | 92 | 39 |
| SP722 + D183* G184* A186T N195F | 103 | 91 | 38 |
| SP722 + D183* G184* N195F V206L H210Y | 102 | 90 | 37 |
| SP722 + D183* G184* S193T V206L | 101 | 89 | 36 |
| SP722 + D183* G184* S193T V213A | 108 | 96 | 43 |
| SP722 + D183* G184* S193T Y243F | 103 | 91 | 38 |
| SP722 + D183* G184* N195F V206N | 107 | 95 | 42 |

The results clearly show that the variants of the invention are considerably more resistant to the presence of strong chelating agents than the reference alpha-amylase. In a few instances the residual activity is above 100, reflecting the analytical variance of the assay.

The results show that the variants of the invention also at pH 8.0 have improved stability compared with the reference alpha-amylase, which may be SEQ ID NO: 6 (SP722) or SEQ ID NO: 6+D183* G184*, which is SEQ ID NO: 6 wherein amino acid 183 and 184 has been deleted.

Example 4: Residual Activity after Incubation with Chelating Agent at pH8 and pH10

In this example the above-described PNP-G7 assay is used to determine the residual amylase activity after incubation in the presence of the chelating agent DTPA, but the principle is the same as above for determine activity using the EnzCheck assay. In general the residual amylase activity was determined after incubation in a buffer containing a chelating agent at either pH 8 and 49° C. or pH 10 and 42° C. for 1 hour and the activity is then compared to the activity of a reference incubated at 4° C. for 1 hour as described above under "Materials and Methods".

Test of Stability of Amylase Variants after Incubation with Chelating Agent at pH8 and pH10 in Buffer Principle:

Enzyme samples were incubated in buffer pH 8.0 with 1.5% final concentration of DTPA at 49° C. for 1 h and reference samples were incubated at 4° C. for 1 h. In addition, enzyme samples were incubated in buffer pH 10.0 with 1.5% final concentration of DTPA at 42° C. for 1 h and their reference samples were incubated at 4° C. for 1 h. After incubation the residual activity was determined using the PNP-G7 amylase activity assay.

Reagents:

pH 8 buffer with DTPA: 50 mM EPPS, 0.01% TRITON™ X100, 1.875% DTPA (Diethylene triamine pentaacetic acid, cas no. 67-43-6), pH8.0 pH 10 buffer with DTPA: 50 mM EPPS, 0.01% TRITON™ X100, 1.875% DTPA (Diethylene triamine pentaacetic acid, cas no. 67-43-6), pH 10.0

Amylase solutions: 0.25 and 0.5 mg active amylase protein/mL in 5 mM EPPS, 0.01% TRITON™ X-100, pH 8.0

Procedure:

160 µL buffer (pH 8 buffer with DTPA or pH 10 buffer with DTPA) and 40 µL of the amylase solutions were transferred to a 96-well PCR microtiter plate in duplicate and the content was mixed for 1 minutes (PCR: Polymerase Chain Reaction). Final concentration of DTPA was 1.5% in each well. 20 µl from each well was transferred to a new PCR microtiter plate (PCR MTP), which was placed at 4° C. (reference sample). The PCR MTP was incubated in PCR machine for 1 h at 49° C. when buffer had pH 8.0 (pH 8, 49° C. samples) and for 1 h at 42° C. when buffer had pH 10.0 (pH 10, 42° C. samples).

Immediately after incubation, the samples on PCR plates were diluted ten-fold in dilution buffer and analyzed for amylase activity as described in PNP-G7 assay. It should be noted, that in order to reduce interference from the chelating agent, here DTPA, on the assay, both reference and pH 8, 49° samples/pH10, 42° C. samples were diluted to the same concentration before being analyzed for residual activity. The activity of both the reference samples and the pH 8, 49° C. samples or pH 10, 42° C. samples were determined on the same 96 well plate. It was ensured that the parent amylase was included on all test microtiter plates. The residual activity was calculated as 100*$V_{max}$ (pH 8, 42° C. or pH 10, 49° C. sample)/$V_{max}$ (reference sample) and the results are shown in table 4.1. The percentage points (pp) improvements are calculated as the residual activity of the variant minus the residual activity of the parent.

TABLE 4

| | pH 8, 49° C. | | | pH 10, 42° C. | | |
|---|---|---|---|---|---|---|
| | Residual activity (%) | pp point improvement of variant relative to parent | | Residual activity (%) | pp improvement of Ivariant relative to parent | |
| Enzyme | | SP722 | SP722 + D183* 184* | | SP722 | SP722 + D183* 184* |
| SP722 (parent) | 1 | 0 | | 8 | 0 | |
| SP722 + D183* G184* (Parent) | 20 | — | 0 | 20 | — | 0 |
| SP722 + D183* G184* N195F V206L Y243F | 97 | 96 | 77 | 93 | 85 | 73 |
| SP722 + D183* G184* N195F V206Y Y243F | 97 | 96 | 77 | 100 | 92 | 80 |
| SP722 + D183* G184* N195F V206N Y243F | 96 | 95 | 75 | 92 | 84 | 64 |
| SP722 + D183* G184* N195F V206F Y243F | 101 | 100 | 80 | 97 | 89 | 69 |
| SP722 + D183* G184* N195F V206H | 92 | 92 | 72 | 88 | 80 | 60 |
| SP722 + D183* G184* N195F V206Y | 95 | 94 | 74 | 96 | 88 | 68 |
| SP722 + D183* G184* V206F Y243F | 87 | 86 | 66 | 89 | 81 | 61 |
| SP722 + D183* G184* N195F V206L H210Y | 98 | 97 | 77 | 96 | 88 | 68 |
| SP722 + D183* G184* S193T V206L | 79 | 78 | 58 | 73 | 65 | 45 |
| SP722 + D183* G184* G133E G149R N195Y Y203F V206L | 90 | 89 | 69 | 83 | 75 | 55 |

The results clearly show that the variants of the invention are highly stable and have high residual activity after incubation at pH 8 49° C. and pH 10 42° C. for 1 hour both when comparing the residual activities of the variants with that of the parent and when looking at the percentage point improvement of the variants. In comparison SP722+0183* G184* amylase has 20% residual activity and SP722 has even less residual activity.

Example 5: Residual Activity after Incubation in Buffer with 1.5% (w/v) DTPA at pH8 and pH10

In this example the above-described PNP-G7 assay is used to determine the residual amylase activity SP722 variants after incubation in the presence of the chelating agent DTPA. In general the residual amylase activity was determined after incubation in a buffer containing a chelating agent at either pH 8 or pH 10 at the indicated temperatures and incubation times and the activity is then compared to the activity of a reference incubated at 4° C. as described above under "Materials and Methods".

Test of Stability of Amylase Variants after Incubation with Chelating Agent at pH8 and PH10 in Buffer Principle:

Enzyme samples were incubated in buffer pH 8.0 with 1.5% (w/v) final concentration of DTPA at indicated temperature and incubation time and reference samples were incubated at 4° C. at same incubation time. In addition, enzyme samples were incubated in buffer pH 10.0 with 1.5% (w/v) final concentration of DTPA at indicated temperature and incubation time and their reference samples were incubated at 4° C. at same incubation time. After incubation the residual activity was determined using the PNP-G7 amylase activity assay.

Reagents:

pH 8 buffer with DTPA: 50 mM EPPS, 0.01% (w/v) TRITON™ X100, 1.875% (w/v) DTPA (Diethylene triamine pentaacetic acid, cas no. 67-43-6), pH8.0 pH 10 buffer with DTPA: 50 mM Glycine, 0.01% (w/v) TRITON™ X100, 1.875% (w/v) DTPA (Diethylene triamine pentaacetic acid, cas no. 67-43-6), pH 10.0

Amylase solutions: 0.25 and 0.5 mg active amylase protein/mL in 5 mM EPPS, 0.01% TRITON™ X-100, pH 8.0

Procedure:

160 µL buffer (pH 8 buffer with DTPA or pH 10 buffer with DTPA) and 40 µL of the amylase solutions were transferred to a 96-well PCR microtiter plate in duplicate and the content was mixed for 1 minutes (PCR: Polymerase Chain Reaction). Final concentration of DTPA was 1.5% (w/v) in each well. 20 µl from each well was transferred to a microtiter plate (MTP), which was placed at 4° C. (reference sample). The PCR MTP (stressed sample) was incubated in PCR machine as indicated in table below.

Immediately after incubation, the samples on PR plates were diluted ten-fold in dilution buffer and analyzed for amylase activity as described in PNP-G7 assay. It should be noted, that in order to reduce interference from the chelating agent, here DTPA, on the assay, both reference and stressed samples were diluted to the same concentration before being analyzed for residual activity. The activity of both the reference samples and the stressed were determined on the same 96 well plate. It was ensured that the parent amylase was included on all test microtiter plates. The residual activity was calculated as 100*$V_{max}$ (stressed sample)/$V_{max}$ (reference sample). The percentage point (pp) improvement in the stability of the variants relative to the parent is calculated as the residual activity of the variant minus the residual activity of the parent. The results are shown in table 5.1.

TABLE 5.1

| SP722 variants with DTPA chelator | | | | |
|---|---|---|---|---|
| | pH 8, 49° C., 10 minutes, 1.5% DTPA | | pH 10, 42° C., 20 minutes, 1.5% DTPA | |
| Enzyme | Residual activity (%) | pp improvement in residual activity relative to parent | Residual activity (%) | pp improvement in residual activity relative to parent |
| SP722 (parent) | 29 | 0 | 25 | 0 |
| SP722 + N195F | 51 | 22 | 42 | 17 |
| SP722 + V206L | 36 | 7 | 32 | 7 |
| SP722 + V206Y | 48 | 19 | 141 | 16 |
| SP722 + Y243F | 34 | 5 | 35 | 10 |
| SP722 + N195F V206L | 68 | 39 | 62 | 37 |
| SP722 + N195F V206L Y243F | 78 | 49 | 77 | 52 |

From the residual activities it is clearly seen that the variants of SP722 is more stable in the presence of DTPA, which is also reflected in the percentage points improvements in the stability of the variant compared to the parent.

Example 6: Residual Activity after Incubation with HEDP at pH 10

In this example the above-described PNP-G7 assay is used to determine the residual amylase activity after incubation in the presence of the chelating agent HEDP. In general the residual amylase activity was determined after incubation in a buffer containing a chelating agent at pH 10 at the indicated temperatures and incubation times and the activity is then compared to the activity of a reference incubated at 4° C. as described above under Materials and Methods.

Test of Stability of Amylase Variants after Incubation with Chelating Agent at PH10 in Buffer Principle:

Enzyme samples were incubated in buffer pH 10.0 with 1.5% (w/v) final concentration of HEDP at indicated temperature and incubation time and reference samples were incubated at 4° C. at same incubation time. After incubation the residual activity was determined using the PNP-G7 amylase activity assay.

Reagents:

pH 10 buffer with HEDP: 50 mM Glycine, 0.01% (w/v) TRITON™ X100, 1.875% (w/v) HEDP (1-Hydroxyethylidenediphosphonic acid, cas no 2809-21-4), pH 10.0

Amylase solutions: 0.25 and 0.5 mg active amylase protein/mL in 5 mM EPPS, 0.01% (w/v) TRITON™ X-100, pH 8.0

Procedure:

160 µL buffer (pH 10 buffer with HEDP) and 40 µL of the amylase solutions were transferred to a 96-well PCR microtiter plate in duplicate and the content was mixed for 1 minute (PCR: Polymerase Chain Reaction). Final concentration of HEDP was 1.5% (w/v) in each well. 20 µl from each well was transferred to a microtiter plate (MTP), which was placed at 4° C. (reference sample). The PCR MTP (stressed sample) was incubated in PCR machine as indicated in table 6.1 below. The residual activity was calculated as 100*$V_{max}$ (stressed sample)/$V_{max}$ (reference sample). The percentage point (pp) improvement in the stability of the variants relative to the parent is calculated as the residual activity of the variant minus the residual activity of the parent.

TABLE 6.1

| SP722 and variant thereof with HEDP | | |
|---|---|---|
| | pH 10, 42° C., 20 minutes, 1.5% HEDP | |
| Enzyme | Residual activity (%) | pp improvement relative to parent |
| SP722 (parent) | 44 | 0 |
| SP722 + N195F V206L Y243F | 76 | 32 |

The results clearly show that the variant is more stable when incubated in the presence of HEDP compared to the parent.

Example 7: Stability of SP722+D183* G184* and Variants Thereof with 1.5% (w/v) HEDP In this example the above-described PNP-G7 assay is used to determine the residual amylase activity after incubation in the presence of the chelating agent HEDP. In general, the residual amylase activity was determined after incubation in a buffer containing a chelating agent at either pH 8 or pH 10 at the indicated temperatures and incubation times and the activity is then compared to the activity of a reference incubated at 4° C. as described above under Materials and Methods.

Test of Stability of Amylase Variants after Incubation with Chelating Agent at PH 8 and PH 10 in Buffer Principle:

Enzyme samples were incubated in buffer pH 8.0 with 1.5% (w/v) final concentration of HEDP at indicated temperature and incubation time and reference samples were incubated at 4° C. at same incubation time. In addition, enzyme samples were incubated in buffer pH10.0 with 1.5% (w/v) final concentration of HEDP at indicated temperature and incubation time and their reference samples were incubated at 4° C. at same incubation time. After incubation the residual activity was determined using the PNP-G7 amylase activity assay.

Reagents:

- pH 8 buffer with HEDP: 50 mM EPPS, 0.01% (w/v) TRITON™ X100, 1.875% (w/v) HEDP (1-Hydroxyethylidenediphosphonic acid, cas no 2809-21-4), pH 8.0
- pH 10 buffer with HEDP: 50 mM Glycine, 0.01% (w/v) TRITON™ X100, 1.875% (w/v) HEDP (1-Hydroxyethylidenediphosphonic acid, cas no 2809-21-4), pH 10.0
- Amylase solutions: 0.25 and 0.5 mg active amylase protein/mL in 5 mM EPPS, 0.01% (w/v) TRITON™ X-100, pH 8.0

Procedure:

160 μL buffer (pH 8 buffer with HEDP or pH 10 buffer with HEDP) and 40 μL of the amylase solutions were transferred to a 96-well PCR microtiter plate in duplicate and the content was mixed for 1 minutes (PCR: Polymerase Chain Reaction). Final concentration of HEDP was 1.5% (w/v) in each well. 20 μl from each well was transferred to a microtiter plate (MTP), which was placed at 4° C. (reference sample). The PCR MTP (stressed sample) was incubated in PCR machine as indicated in table 7.1 below. The residual activity was calculated as $100*V_{max}$ (stressed sample)/$V_{max}$ (reference sample). The percentage point (pp) improvement in the stability of the variants relative to the parent is calculated as the residual activity of the variant minus the residual activity of the parent.

TABLE 7-1

SP722 + D183* G184* variants with HEDP

| | pH 8, 50° C., 210 minutes, 1.5% HEDP | | pH 10, 42° C., 60 minutes, 1.5% HEDP | |
|---|---|---|---|---|
| Enzyme | Residual activity (%) | pp improvement relative to parent | Residual activity (%) | pp improvement relative to parent |
| SP722 + D183* G184* (parent) | 16 | 0 | 16 | 0 |
| SP722 + D183* G184* N195F V206Y Y243F | 96 | 80 | 95 | 79 |
| SP722 + D183* G184* S193T V206L | 61 | 45 | 62 | 46 |
| SP722 + D183* G184* G133E G149R N195Y Y203F V206L | 82 | 66 | 74 | 58 |

The results clearly shows that the variants of SP722+D183* G184* are much more stable when incubated in the presence of HEDP as chelating agent.

Example 8: Stability of AA560 Variants in the Presence of 1.5% (w/v) DTPA or 1.5% (w/v) HEDP In this example the above-described PNP-G7 assay is used to determine the residual amylase activity after incubation in the presence of the chelating agent DTPA or HEDP. In general the residual amylase activity was determined after incubation in a buffer containing a chelating agent at either pH 8 or pH 10 at the indicated temperatures and incubation times and the activity is then compared to the activity of a reference incubated at 4° C. as described above under "Materials and Methods".

Test of Stability of Amylase Variants after Incubation with Chelating Agent at PH8 and PH10 in Buffer Principle:

Enzyme samples were incubated in buffer pH 8.0 with 1.5% (w/v) final concentration of DTPA or HEDP at indicated temperature and incubation time and reference samples were incubated at 4° C. at same incubation time. In addition, enzyme samples were incubated in buffer pH10.0 with 1.5% (w/v) final concentration of DTPA or HEDP at indicated temperature and incubation time and their reference samples were incubated at 4° C. at same incubation time. After incubation the residual activity was determined using the PNP-G7 amylase activity assay.

Reagents:

- pH 8 buffer with DTPA: 50 mM EPPS, 0.01% (w/v) TRITON™ X100, 1.875% (w/v) DTPA (Diethylene triamine pentaacetic acid, cas no. 67-43-6), pH 8.0
- pH 10 buffer with DTPA: 50 mM Glycine, 0.01% (w/v) TRITON™ X100, 1.875% (w/v) DTPA (Diethylene triamine pentaacetic acid, cas no. 67-43-6), pH 10.0
- pH 8 buffer with HEDP: 50 mM EPPS, 0.01% (w/v) TRITON™ X100, 1.875% (w/v) HEDP (1-Hydroxyethylidenediphosphonic acid, cas no 2809-21-4), pH 8.0
- pH 10 buffer with HEDP: 50 mM Glycine, 0.01% (w/v) TRITON™ X100, 1.875% (w/v) HEDP (1-Hydroxyethylidenediphosphonic acid, cas no 2809-21-4), pH 10.0

Amylase solutions: 0.25 and 0.5 mg active amylase protein/mL in 5 mM EPPS, 0.01% (w/v) TRITON™ X-100, pH 8.0

Procedure:

160 µL buffer (pH 8 buffer with DTPA or HEDP or pH 10 buffer with DTPA or HEDP) and 40 µL of the amylase solutions were transferred to a 96-well PCR microtiter plate in duplicate and the content was mixed for 1 minutes (PCR: Polymerase Chain Reaction). Final concentration of DTPA or HEDP was 1.5% (w/v) in each well. 20 µl from each well was transferred to a microtiter plate (MTP), which was placed at 4° C. (reference sample). The PCR MTP (stressed sample) was incubated in PCR machine as indicated in table 8.1 and 8.2 below. The residual activity was calculated as $100*V_{max}$ (stressed sample)/$V_{max}$ (reference sample). The percentage point (pp) improvement in the stability of the variants relative to the parent is calculated as the residual activity of the variant minus the residual activity of the parent.

TABLE 8.1

AA560 variants with DTPA

| | pH 8, 49° C., 150 minutes, 1.5% DTPA | | pH 10, 42° C., 60 minutes, 1.5% DTPA | |
|---|---|---|---|---|
| Enzyme | Residual activity (%) | pp improvement relative to parent | Residual activity (%) | pp improvement relative to parent |
| AA560 + 118K D183* G184* N195F R320K R458K (parent) | 20 | 0 | 21 | 0 |
| Parent + I206L | 49 | 29 | 45 | 24 |
| Parent + I206Y | 77 | 57 | 78 | 57 |
| Parent + Y243F | 31 | 11 | 36 | 15 |

TABLE 8.2

AA560 variants with HEDP

| | pH 8, 50° C., 210 minutes, 1.5% HEDP | | pH 10, 42° C., 60 minutes, 1.5% HEDP | |
|---|---|---|---|---|
| Enzyme | Residual activity (%) | pp improvement relative to parent | Residual activity (%) | pp improvement relative to parent |
| AA560 + 118K D183* G184* N195F R320K R458K (parent) | 60 | 0 | 19 | 0 |
| Parent + I206L | 68 | 8 | 38 | 19 |
| Parent + I206Y | 85 | 25 | 72 | 53 |
| Parent + Y243F | 59 | −1 | 34 | 15 |

Various references are cited herein, the disclosures of which are incorporated by reference in their entireties.

Example 9: Residual Activity after Incubation in Detergent with Chelating Agent In this example the PNP-G7 assay is used to determine the residual amylase activity after incubation in the detergent in the presence of chelating agents, as described in above under "Materials and Methods".

In general, the residual amylase activity was determined after incubation in detergent C (Table 9.1), containing chelating agents DTPMP and HEDP at pH 8.2 after 3 weeks and 6 weeks 30° C. The residual activity of the amylase is then compared to the activity of the amylase in the freshly made detergent at day zero (before incubation) as described below.

TABLE 9.1

| Detergent C | |
|---|---|
| Detergent C Ingredient | Composition of Detergent used for stability testing Composition (wt % of composition) |
| $C_{11.8}$ Alkylbenzene sulfonate | 5.89 |
| Citric acid | 2.56 |
| $C_{12-18}$ fatty acid | 2.56 |
| Sodium $C_{12-14}$ alkyl ethoxy 3 sulfate | 1.96 |
| $C_{14-15}$ alkyl-7-ethoxylate | 1.94 |
| $C_{12-14}$ Alkyl-7-ethoxylate | 2.21 |
| Boric Acid | 0.5 |
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulphated or sulphonated variants thereof | 1.46 |
| DTPMP (Diethylene triamine penta (methylene phosphonic acid) | 0.19 |
| HEDP (Hydroxyethane diphosphonic acid) | 1.6 |
| Ethanol | 1.95 |
| Propylene Glycol | 1.5 |
| Monoethanolamine | 5.15 |
| Water, Aesthetics (Dyes, perfumes), pH adjusters (sodium hydroxide) and Minors (Enzymes, solvents, structurants, brighteners) | Balance to pH 8.2 |

Test of Stability of Amylase Variants after Incubation in Detergent C with Chelating Agents at pH 8.2

Method

Detergent C, pH 8.2, samples were prepared each containing an amylase variant of the invention or the SEQ ID NO: 6 (SP722) with the following two deletions D183*+G184*—also ref to as SP722+D183* G184*. Each detergent sample was determined for the initial residual enzyme activity before incubation (reference samples).

The residual enzyme activity for each sample was determined after incubation at 30° C. for 3 weeks and 6 weeks and compared to their reference sample. The residual activity was determined using the PNP-G7 amylase activity assay.

Amylase solutions: 13.77 mg active amylase protein in 100 g detergent C, pH 8.2.

Procedure:

Detergent C, 5 g pH 8.2 containing the amylase was placed in duplicate into a 7 ml glass vial with an air-tight lid. The residual enzyme activity was determined for the initial samples, in duplicate, before incubation.

The samples were placed into an incubator for 3 weeks and 6 weeks at 30° C. Immediately after incubation, the samples were analysed for residual amylase activity as described in PNP-G7 assay. In this test the residual activity of 100% equals no loss of amylase activity compared to initial residual enzyme activity before incubation (reference sample). The percentage point (pp) improvement in residual activity (stability) of the variant relative to the parent is calculated as the difference between the residual activity of the variant and the residual activity of the parent.

TABLE 9.2

| | Residual activity pH 8.2, 30° C. | | pp improvement in residual activity relative to parent | |
|---|---|---|---|---|
| | 3 Weeks | 6 Weeks | 3 Weeks | 6 Weeks |
| SP722 + D183* G184* (parent) | 19 | 3 | | |
| SP722 + D183* G184* N195F | 67 | 47 | 48 | 44 |
| SP722 + D183* G184* N195F H210Y | 82 | 78 | 63 | 75 |
| SP722 + D183* G184* N195F V206L | 87 | 83 | 68 | 80 |
| SP722 + D183* G184* N195F V206Y | 98 | 97 | 79 | 94 |
| SP722 + D183* G184* N195F V206Y Y243F | 100 | 97 | 81 | 94 |

The results clearly show that the variants of the invention are highly stable and have high residual activity after incubation in detergent C at pH 8.2, 3 weeks and 6 weeks 30° C. In comparison SP722+D183* G184* amylase has 19% after 3 weeks and 3% after 6 weeks residual activity.

Various references are cited herein, the disclosures of which are incorporated by reference in their entireties.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as “40 mm” is intended to mean “about 40 mm”.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

```
                              SEQUENCE LISTING


Sequence total quantity: 26
SEQ ID NO: 1             moltype = DNA  length = 1440
FEATURE                  Location/Qualifiers
source                   1..1440
                         mol_type = genomic DNA
                         organism = Bacillus sp.
CDS                      1..1440
SEQUENCE: 1
gatggattga acggtacgat gatgcagtat tatgagtggc atttggaaaa cgacgggcag  60
cattggaatc ggttgcacga tgatgccgca gctttgagtg atgctggtat tacagctatt  120
tggattccgc cagcctacaa aggtaatagt caggcggatg ttgggtacgg tgcatacgat  180
ctttatgatt taggagagtt caatcaaaag ggtactgttc gaacgaaata cggaactaag  240
gcacagcttg aacgagctat tgggtccctt aaatctaatg atatcaatgt atacggagat  300
gtcgtgatga atcataaaat gggagctgat tttacggagg cagtgcaagc tgttcaagta  360
aatccaacga atcgttggca ggatatttca ggtgcctaca cgattgatgc gtggacgggt  420
ttcgactttt cagggcgtaa caacgcctat tcagatttta agtggagatg gttccatttt  480
aatggtgttg actgggatca gcgctatcaa gaaaatcata ttttccgctt tgcaaatacg  540
aactggaact ggcgagtgga tgaagagaac ggtaattatg attacctgtt aggatcgaat  600
atcgacttta gtcatccaga agtacaagat gagttgaagg attggggtag ctggtttacc  660
gatgagttag atttggatgg ttatcgttta gatgctatta aacatattcc attctggtat  720
acatctgatt gggttcggca tcagcgcaac gaagcagatc aagatttatt tgtcgtaggg  780
gaatattgga aggatgacgt aggtgctctc gaattttatt tagatgaaat gaattgggag  840
atgtctctat tcgatgttcc acttaattat aatttttacc gggcttcaca acaaggtgga  900
agctatgata tgcgtaatat tttacgagga tctttagtag aagcgcatcc gatgcatgca  960
gttacgtttg ttgataatca tgatactcag ccaggggagt cattagagtc atgggttgct  1020
gattggttta agccacttgc ttatgcgaca attttgacgc gtgaaggtgg ttatccaaat  1080
gtattttacg gtgattacta tggattcct aacgataaca tttcagctaa aaaagatatg  1140
attgatgagc tgcttgatgc acgtcaaaat tacgcatatg gcacgcagca tgactatttt  1200
gatcattggg atgttgtagg atggactagg gaaggatctt cctccagacc taattcaggc  1260
cttgcgacta ttatgtcgaa tggacctggt ggttccaagt ggatgtatgt aggacgtcag  1320
aatgcaggac aaacatggac agatttaact ggtaataacg gagcgtccgt tacaattaat  1380
ggcgatggat ggggcgaatt ctttacgaat ggaggatctg tatccgtgta cgtgaaccaa  1440

SEQ ID NO: 2             moltype = AA  length = 480
FEATURE                  Location/Qualifiers
source                   1..480
                         mol_type = protein
                         organism = Bacillus sp.
SEQUENCE: 2
DGLNGTMMQY YEWHLENDGQ HWNRLHDDAA ALSDAGITAI WIPPAYKGNS QADVGYGAYD  60
LYDLGEFNQK GTVRTKYGTK AQLERAIGSL KSNDINVYGD VVMNHKMGAD FTEAVQAVQV  120
NPTNRWQDIS GAYTIDAWTG FDFSGRNNAY SDFKWRWFHF NGVDWDQRYQ ENHIFRFANT  180
NWNWRVDEEN GNYDYLLGSN IDFSHPEVQD ELKDWGSWFT DELDLDGYRL DAIKHIPFWY  240
TSDWVRHQRN EADQDLFVVG EYWKDDVGAL EFYLDEMNWE MSLFDVPLNY NFYRASQQGG  300
SYDMRNILRG SLVEAHPMHA VTFVDNHDTQ PGESLESWVA DWFKPLAYAT ILTREGGYPN  360
VFYGDYYGIP NDNISAKKDM IDELLDARQN YAYGTQHDYF DHWDVVGWTR EGSSSRPNSG  420
LATIMSNGPG GSKWMYVGRQ NAGQTWTDLT GNNGASVTIN GDGWGEFFTN GGSVSVYVNQ  480

SEQ ID NO: 3             moltype = DNA  length = 1476
FEATURE                  Location/Qualifiers
source                   1..1476
                         mol_type = genomic DNA
                         organism = Bacillus circulans
CDS                      1..1476
SEQUENCE: 3
aagagaaatc ataccatgat gcagtttttt gaatggcacc tggctgcaga cggagatcat  60
tggaagcgac tggctgaaat ggccccggaa ttgaaagcca aaggcattga tacggtatgg  120
gtgcctcctg tgaccaaagc cgtatcagct gaggatacag gttatggtgt atatgatctg  180
tatgatttgg gtgaatttga ccaaaagggt accgtgcgta ccaaatacgg caccaagcag  240
gaactgatag aggccattgc tgagtgtcag aagaacggaa tcgccgtcta tgtggatctg  300
gttatgaatc acaaggccgg agcagatgag acggaagttt ttaaagtgat tgaggttgat  360
cccaatgatc gaacgaagga aatttctgag ccgttcgaaa ttgagggctg gaccaaattc  420
acattcccgg gtcgcgggga tcaatactcc tcttttaaat ggaactctga acacttcaat  480
ggcacggact ttgatgccag ggaagaacga acaggtgtat tccgcatcgc aggagagaat  540
aaaaaatgga atgagaatgt cgatgatgag tttggtaact atgactatct gatgttcgcc  600
aatatagatt ataaccaccc ggatgttcgg cgcgagatga tcgattgggg gaaatggctg  660
atcgataccc ttcagtgcgg tgggttccgg ctggatgcga ttaagcatat caaccatgaa  720
ttcattaagg agttcgcagc agagatgatc cgcaaacgcg gtcaggattt ctacatcgta  780
ggcgagttct ggaactcgaa cctggatgca tgtcgtgaat tccttgatac ggtagactat  840
cagatcgacc tgtttgatgt gtctcttcac tacaagttgc atgaggcttc gcttaaaggc  900
agagactttg atctctccaa aatttttgat gacaccttgg tgcagaccca tcctacccat  960
gcggtaacct tcgtagataa ccatgactcc caacctcatg aagcgttgga atcatggatt  1020
ggtgattggt ttaagccgag cgcttatgcg ttgacgctat tacgtcgtga tggctatccg  1080
gttgtatttt acggcgatta ttatggcatt ggtggtcctg aacctgtgga tggcaaaaaa  1140
gaaattctgg acattctgct gtctgcccgt tgcaacaaag cgtatggaga gcaggaagat  1200
```

```
tacttcgatc acgccaatac gattggctgg gtacgtcgtg gcgtagagga aatcgaaggt  1260
tccggttgtg cagtggtcat ctccaacggg gatgacggtg agaagagaat gttcatcgga  1320
gagcatcgtg ctggtgaagt ctgggtggat ctgacgaaga gctgtgatga tcagattacc  1380
attgaggaag acggctgggc caccttccat gtgtgcggtg gaggtgtctc ggtatgggct  1440
cttcctgaac agaatgagga ctgcgctgac gctgag                            1476

SEQ ID NO: 4           moltype = AA  length = 492
FEATURE                Location/Qualifiers
source                 1..492
                       mol_type = protein
                       organism = Bacillus circulans
SEQUENCE: 4
KRNHTMMQFF EWHLAADGDH WKRLAEMAPE LKAKGIDTVW VPPVTKAVSA EDTGYGVYDL  60
YDLGEFDQKG TVRTKYGTKQ ELIEAIAECQ KNGIAVYVDL VMNHKAGADE TEVFKVIEVD  120
PNDRTKEISE PFEIEGWTKF TFPGRGDQYS SFKWNSEHFN GTDFDAREER TGVFRIAGEN  180
KKWNENVDDE FGNYDYLMFA NIDYNHPDVR REMIDWGKWL IDTLQCGGFR LDAIKHINHE  240
FIKEFAAEMI RKRGQDFYIV GEFWNSNLDA CREFLDTVDY QIDLFDVSLH YKLHEASLKG  300
RDFDLSKIFD DTLVQTHPTH AVTFVDNHDS QPHEALESWI GDWFKPSAYA LTLLRRDGYP  360
VVFYGDYYGI GGPEPVDGKK EILDILLSAR CNKAYGEQED YFDHANTIGW VRRGVEEIEG  420
SGCAVVISNG DDGEKRMFIG EHRAGEVWVD LTKSCDDQIT IEEDGWATFH VCGGGVSVWA  480
LPEQNEDCAD AE                                                      492

SEQ ID NO: 5           moltype = DNA  length = 1455
FEATURE                Location/Qualifiers
source                 1..1455
                       mol_type = genomic DNA
                       organism = Bacillus sp.
CDS                    1..1455
SEQUENCE: 5
catcataatg ggacaaatgg gacgatgatg caatactttg aatggcactt gcctaatgat  60
gggaatcact ggaatagatt aagagatgat gctagtaatc taagaaatag aggtataacc  120
gctatttgga ttccgcctgc ctggaaaggg acttcgcaaa atgatgtggg gtatggagcc  180
tatgatcttt acgatttagg ggaatttaat caaaagggga cggttcgtac taagtatggg  240
acacgtagtc aattggagtc tgccatccat gctttaaaga ataatggcgt tcaagtttat  300
ggggatgtag tgatgaacca taaaggagga gctgatgcta cagaaaacgt tcttgctgtc  360
gaggtgaatc caaataaccg gaatcaagaa atatctgggg actacacaat tgaggcttgg  420
actaagtttg attttccagg gaggggtaat acatactcag actttaaatg gcgttggtat  480
catttcgatg gtgtagattg ggatcaatca cgacaattcc aaaatcgtat ctacaaattc  540
cgaggtgatg gcaaagcttg ggattgggaa gtagattcgg aaaatggaaa ttatgattat  600
ttaatgtatg cagatgtaga tatggatcat ccggaggtag taaatgagct tagaagatgg  660
ggagaatggt atacaaatac attaaatctt gatggattta ggatcgatgc ggtgaagcat  720
attaaatata gctttacacg tgattggttg acccatgtaa gaaacgcaac gggaaaagaa  780
atgtttgctg ttgctgaatt ttggaaaaat gatttaggtg ccttggagaa ctatttaaat  840
aaaacaaact ggaatcattc tgtctttgat gtcccccttc attataatct ttataacgcg  900
tcaaatagtg gaggcaacta tgacatggca aaacttctta atggaacggt tgttcaaaag  960
catccaatgc atgccgtaac ttttgtggat aatcacgatt ctcaacctgg ggaatcatta  1020
gaatcatttg tacaagaatg gtttaagcca cttgcttatg cgcttatttt aacaagagaa  1080
caaggctatc cctctgtctt ctatggtgac tactatggaa ttccaacaca tagtgtccca  1140
gcaatgaaag ccaagattga tccaatctta gaggcgcgtc aaaattttgc atatggaaca  1200
caacatgatt attttgacca tcataatata atcggatgga cacgtgaagg aaataccacg  1260
catcccaatt caggacttgc gactatcatg tcggatgggc caggggggaga gaaatggatg  1320
tacgtagggc aaaataaagc aggtcaagtt tggcatgaca taactggaaa taaaccagga  1380
acagttacga tcaatgcaga tggatgggct aatttttcag taaatggagg atctgtttcc  1440
atttgggtga aacga                                                   1455

SEQ ID NO: 6           moltype = AA  length = 485
FEATURE                Location/Qualifiers
source                 1..485
                       mol_type = protein
                       organism = Bacillus sp.
SEQUENCE: 6
HHNGTNGTMM QYFEWHLPND GNHWNRLRDD ASNLRNRGIT AIWIPPAWKG TSQNDVGYGA  60
YDLYDLGEFN QKGTVRTKYG TRSQLESAIH ALKNNGVQVY GDVVMNHKGG ADATENVLAV  120
EVNPNNRNQE ISGDYTIEAW TKFDFPGRGN TYSDFKWRWY HFDGVDWDQS RQFQNRIYKF  180
RGDGKAWDWE VDSENGNYDY LMYADVDMDH PEVVNELRRW GEWYTNTLNL DGFRIDAVKH  240
IKYSFTRDWL THVRNATGKE MFAVAEFWKN DLGALENYLN KTNWNHSVFD VPLHYNLYNA  300
SNSGGNYDMA KLLNGTVVQK HPMHAVTFVD NHDSQPGESL ESFVQEWFKP LAYALILTRE  360
QGYPSVFYGD YYGIPTHSVP AMKAKIDPIL EARQNFAYGT QHDYFDHHNI IGWTREGNTT  420
HPNSGLATIM SDGPGGEKWM YVGQNKAGQV WHDITGNKPG TVTINADGWA NFSVNGGSVS  480
IWVKR                                                              485

SEQ ID NO: 7           moltype = DNA  length = 1455
FEATURE                Location/Qualifiers
source                 1..1455
                       mol_type = genomic DNA
                       organism = Bacillus sp.
CDS                    1..1455
SEQUENCE: 7
catcataacg gtacgaacgg gacaatgatg caatactttg aatggtatct acctaatgac  60
```

-continued

```
ggaaatcatt ggaatcgatt aaactctgat gcgagtaacc ttaaaagcaa agggattaca  120
gcggtgtgga ttcctccagc atggaagggc gcttctcaaa atgacgtagg atacggagcc  180
tatgacctgt atgatctggg agaatttaat caaaaaggta ccgtccgtac aaaatatgga  240
acacgtagtc agttacaagc tgcggtaacc tccttaaaaa ataatggaat tcaagtatat  300
ggtgacgttg ttatgaatca caaaggtggc gcagacgcta ctgaaatggt aagggccgtt  360
gaagtgaatc ccaataaccg taaccaagaa gtgactggtg aatataccat tgaagcttgg  420
actagatttg attttccagg gcgaggaaat actcattcta gctttaaatg gagatggtat  480
cattttgatg gtgtggattg ggatcagtca cgtagactga acaatcgcat ctataaattt  540
agaggtcatg gcaaagcttg ggattgggaa gttgatacgg aaaatggtaa ttatgattat  600
ttaatgtacg ctgatattga tatggatcac ccagaagtag taaatgaatt aagaaattgg  660
ggtgtttggt acacaaacac attaggactc gatggattta gaatagatgc ggttaaacat  720
ataaagtata gctttacgcg cgattggatt aatcacgtta gaagtgcaac aggtaaaaat  780
atgtttgcgg ttgctgagtt ttggaagaat gatttaggtg caattgaaaa ctatctgcag  840
aaaacaaact ggaaccattc agtctttgat gtgccgttac attataatct ttataatgca  900
tcaaaaagcg gagggaacta tgatatgcga aacatattta atggaacggt tgttcaacga  960
catccaagtc atgctgtaac atttgttgat aatcatgatt cgcagcctga agaagcatta  1020
gaatcttttg ttgaagaatg gtttaaacca ttagcgtatg cgcttacatt aacgcgtgaa  1080
caaggatacc cttctgtatt ttacggagat tattatggga ttccaacaca tggagtgcca  1140
gcaatgagat caaaaatcga tccgatttta gaagcacgtc aaaagtatgc atacggaaaa  1200
caaaatgatt acttagacca tcataatatc attggttgga cgcgtgaagg gaatacagca  1260
caccccaatt caggtctagc taccatcatg tctgatggag cgggtggaag taagtggatg  1320
tttgttgggc gtaataaggc tggtcaagta tggagtgata ttacaggaaa ccgtacaggt  1380
acggttacaa tcaatgcaga cggttggggc aatttctctg tgaatggagg gtcagtttct  1440
atttgggtca acaaa                                                   1455
```

```
SEQ ID NO: 8           moltype = AA  length = 485
FEATURE                Location/Qualifiers
source                 1..485
                       mol_type = protein
                       organism = Bacillus sp.
SEQUENCE: 8
HHNGTNGTMM QYFEWYLPND GNHWNRLNSD ASNLKSKGIT AVWIPPAWKG ASQNDVGYGA  60
YDLYDLGEFN QKGTVRTKYG TRSQLQAAVT SLKNNGIQVY GDVVMNHKGG ADATEMVRAV  120
EVNPNNRNQE VTGEYTIEAW TRFDFPGRGN THSSFKWRWY HFDGVDWDQS RRLNNRIYKF  180
RGHGKAWDWE VDTENGNYDY LMYADIDMDH PEVVNELRNW GVWYTNTLGL DGFRIDAVKH  240
IKYSFTRDWI NHVRSATGKN MFAVAEFWKN DLGAIENYLQ KTNWNHSVFD VPLHYNLYNA  300
SKSGGNYDMR NIFNGTVVQR HPSHAVTFVD NHDSQPEEAL ESFVEEWFKP LAYALTLTRE  360
QGYPSVFYGD YYGIPTHGVP AMRSKIDPIL EARQKYAYGK QNDYLDHHNI IGWTREGNTA  420
HPNSGLATIM SDGAGGSKWM FVGRNKAGQV WSDITGNRTG TVTINADGWG NFSVNGGSVS  480
IWVNK                                                              485
```

```
SEQ ID NO: 9           moltype = DNA  length = 1458
FEATURE                Location/Qualifiers
source                 1..1458
                       mol_type = genomic DNA
                       organism = Bacillus sp.
CDS                    1..1458
SEQUENCE: 9
caccataatg gtacgaacgg cacaatgatg cagtactttg aatggtatct accaaatgac  60
ggaaaccatt ggaatagatt aaggtctgat gcaagtaacc taaaagataa agggatctca  120
gcggtttgga ttcctcctgc atggaagggt gcctctcaaa atgatgtggg gtatggtgct  180
tatgatctgt atgatttagg agaattcaat caaaaaggaa ccattcgtac aaaatatgga  240
acgcgcaatc agttacaagc tgcagttaac gccttgaaaa gtaatggaat tcaagtgtat  300
ggcgatgttg taatgaatca taaaggggga gcagacgcta ccgaaatggt tagggcggtt  360
gaagtaaacc cgaataatag aaatcaagaa gtgtccggtg aatatacaat tgaggcttgg  420
acaaagtttg actttcctgg acgaggtaat acccattcaa acttcaaatg gagatggtat  480
cactttgatg gagtagattg ggatcagtca cgtaagctga acaatcgaat ttataaattt  540
agaggtgatg gaaaagggtg ggattgggaa gtcgatacag aaaacggtaa ctatgattac  600
ctaatgtatg cagatattga catggatcac ccagaggtag tgaatgagct aagaaattgg  660
ggtgtttggt atacgaatac attaggcctt gatggtttta gaatagatgc agtaaaacat  720
ataaaataca gctttactcg tgattggatc aatcatgtta gaagtgcaac tggcaaaaat  780
atgtttgcgg ttgcggaatt ttggaaaaat gatttaggtg ctattgaaaa ctatttaaac  840
aaaacaaact ggaaccattc agtctttgat gttccgctgc actataacct ctataatgct  900
tcaaaaagcg gagggaatta tgatatgagg caaatattta atggtacagt cgtgcaaaga  960
catccaatgc atgctgttac atttgttgat aatcatgatt cgcaacctga agaagcttta  1020
gagtcttttg ttgaagaatg gttcaaacca ttagcgtatg ctttgacatt aacacgtgaa  1080
caaggctacc cttctgtatt ttatggagat tattatggca ttccaacgca tggtgtacca  1140
gcgatgaaat cgaaaattga cccgattcta gaagcgcgtc aaaagtatgc atatggaaga  1200
caaaatgact acttagacca tcataatatc attggttgga cacgtgaagg gaatacagca  1260
cacccccaact ctggtttagc tactatcatg tccgatggag caggaggaaa taagtggatg  1320
tttgttgggc gtaataaagc tggtcaagtt tggaccgata tcactggaaa tcgtgcaggt  1380
actgttacga ttaatgctga tggatggggt aatttttctg taaatggagg atcagtttct  1440
atttgggtaa acaaataa                                                1458
```

```
SEQ ID NO: 10          moltype = AA  length = 485
FEATURE                Location/Qualifiers
source                 1..485
                       mol_type = protein
                       organism = Bacillus sp.
```

-continued

```
SEQUENCE: 10
HHNGTNGTMM QYFEWYLPND GNHWNRLRSD ASNLKDKGIS AVWIPPAWKG ASQNDVGYGA  60
YDLYDLGEFN QKGTIRTKYG TRNQLQAAVN ALKSNGIQVY GDVVMNHKGG ADATEMVRAV  120
EVNPNNRNQE VSGEYTIEAW TKFDFPGRGN THSNFKWRWY HFDGVDWDQS RKLNNRIYKF  180
RGDGKGWDWE VDTENGNYDY LMYADIDMDH PEVVNELRNW GVWYTNTLGL DGFRIDAVKH  240
IKYSFTRDWI NHVRSATGKN MFAVAEFWKN DLGAIENYLN KTNWNHSVFD VPLHYNLYNA  300
SKSGGNYDMR QIFNGTVVQR HPMHAVTFVD NHDSQPEEAL ESFVEEWFKP LAYALTLTRE  360
QGYPSVFYGD YYGIPTHGVP AMKSKIDPIL EARQKYAYGR QNDYLDHHNI IGWTREGNTA  420
HPNSGLATIM SDGAGGNKWM FVGRNKAGQV WTDITGNRAG TVTINADGWG NFSVNGGSVS  480
IWVNK                                                            485

SEQ ID NO: 11          moltype = DNA  length = 1455
FEATURE                Location/Qualifiers
source                 1..1455
                       mol_type = genomic DNA
                       organism = Bacillus sp.
CDS                    1..1455
SEQUENCE: 11
catcataatg gaacaaatgg tactatgatg caatatttcg aatggtattt gccaaatgac  60
gggaatcatt ggaacaggtt gagggatgac gcagctaact taaagagtaa agggataaca  120
gctgtatgga ttccacctgc atggaagggg acttcccaga atgatgtagg ttatggagcc  180
tatgatttat atgatcttgg agagtttaac cagaagggga cggttcgtac aaaatatgga  240
acacgcaacc agctgcaggc tgccgtgaca tctttaaaaa ataacggcat tcaggtatat  300
ggtgatgtcg tcatgaatca taaaggtgga gcagatggta cggaaattgt aaatgcggta  360
gaagtgaatc ggagcaaccg aaaccaggaa acctcaggag agtatgcaat agaagcgtgg  420
acaaagtttg atttcctgg aagaggaaat aaccattcca gctttaagtg gcgctggtat  480
cattttgatg ggacagattg ggatcagtca cgccagcttc aaaacaaaat atataaattc  540
aggggaacag gcaaggcctg ggactgggaa gtcgatacag agaatggcaa ctatgactat  600
cttatgtatg cagacgtgga tatggatcac ccagaagtaa tacatgaact tagaaactgg  660
ggagtgtggt atacgaatac actgaacctt gatggattta gaatagatgc agtgaaacat  720
ataaaatata gctttacgag agattggctt acacatgtgc gtaacaccac aggtaaacca  780
atgtttgcag tggctgagtt ttggaaaaat gaccttggtg caattgaaaa ctatttgaat  840
aaaacaagtt ggaatcactc ggtgtttgat gttcctctcc actataattt gtacaatgca  900
tctaatagcg gtggttatta tgatatgaga aatattttaa atggttctgt ggtgcaaaaa  960
catccaacac atgccgttac ttttgttgat aaccatgatt ctcagcccgg ggaagcattg  1020
gaatcctttg ttcaacaatg gtttaaacca cttgcatatg cattggttct gacaagggaa  1080
caaggttatc cttccgtatt ttatggggat tactacggta tcccaaccca tggtgttccg  1140
gctatgaaat ctaaaataga ccctcttctg caggcacgtc aaacttttgc ctatggtacg  1200
cagcatgatt actttgatca tcatgatatt atcggttgga caagagaggg aaatagctcc  1260
catccaaatt caggccttgc caccattatg tcagatggtc caggtggtaa caaatggatg  1320
tatgtgggga aaaataaagc gggacaagtt tggagagata ttaccggaaa taggacaggc  1380
accgtcacaa ttaatgcaga cggatggggt aatttctctg ttaatggagg gtccgtttcg  1440
gtttgggtga agcaa                                                 1455

SEQ ID NO: 12          moltype = AA  length = 485
FEATURE                Location/Qualifiers
source                 1..485
                       mol_type = protein
                       organism = Bacillus sp.
SEQUENCE: 12
HHNGTNGTMM QYFEWYLPND GNHWNRLRDD AANLKSKGIT AVWIPPAWKG TSQNDVGYGA  60
YDLYDLGEFN QKGTVRTKYG TRNQLQAAVT SLKNNGIQVY GDVVMNHKGG ADGTEIVNAV  120
EVNRSNRNQE TSGEYAIEAW TKFDFPGRGN NHSSFKWRWY HFDGTDWDQS RQLQNKIYKF  180
RGTGKAWDWE VDTENGNYDY LMYADVDMDH PEVIHELRNW GVWYTNTLNL DGFRIDAVKH  240
IKYSFTRDWL THVRNTTGKP MFAVAEFWKN DLGAIENYLN KTSWNHSVFD VPLHYNLYNA  300
SNSGGYYDMR NILNGSVVQK HPTHAVTFVD NHDSQPGEAL ESFVQQWFKP LAYALVLTRE  360
QGYPSVFYGD YYGIPTHGVP AMKSKIDPLL QARQTFAYGT QHDYFDHHDI IGWTREGNSS  420
HPNSGLATIM SDGPGGNKWM YVGKNKAGQV WRDITGNRTG TVTINADGWG NFSVNGGSVS  480
VWVKQ                                                            485

SEQ ID NO: 13          moltype = DNA  length = 1452
FEATURE                Location/Qualifiers
source                 1..1452
                       mol_type = genomic DNA
                       organism = Bacillus amyloliquefaciens
CDS                    1..1449
SEQUENCE: 13
gtaaatggca cgctgatgca gtattttgaa tggtatacgc cgaacgacgg ccagcattgg  60
aaacgattgc agaatgatgc ggaacattta tcggatatcg gaatcactgc cgtctggatt  120
cctcccgcat acaaaggatt gagccaatcc gataacggat acggacctta tgatttgtat  180
gatttaggag aattccagca aaaagggacg gtcagaacga aatacggcac aaaatcagag  240
cttcaagatg cgatcggctc actgcattcc cggaacgtcc aagtatacgg agatgtggtt  300
ttgaatcata aggctggtgc tgatgcaaca gaagatgtaa ctgccgtcga agtcaatccg  360
gccaatagaa atcaggaaac ttcggaggaa tatcaaatca aagcgtggac ggattttcgt  420
tttccgggcc gtggaaacac gtacagtgat tttaaatggc attggtatca tttcgacgga  480
gcggactggg atgaatcccg gaagatcagc cgcatcttta agtttcgtgg ggaaggaaaa  540
gcgtgggatt gggaagtatc aagtgaaaac ggcaactatg actatttaat gtatgctgat  600
gttgactacg accaccctga tgtcgtggca gagacaaaaa aatggggtat ctggtatgcg  660
aatgaactgt cattagacgg cttccgtatt gatgccgcca aacatattaa attttcattt  720
```

-continued

```
ctgcgtgatt gggttcaggc ggtcagacag gcgacgggaa aagaaatgtt tacggttgcg  780
gagtattggc agaataatgc cgggaaactc gaaaactact tgaataaaac aagctttaat  840
caatccgtgt ttgatgttcc gcttcatttc aatttacagg cggcttcctc acaaggaggc  900
ggatatgata tgaggcgttt gctggacggt accgttgtgt ccaggcatcc ggaaaaggcg  960
gttacatttg ttgaaaatca tgacacacag ccgggacagt cattggaatc gacagtccaa  1020
acttggttta aaccgcttgc atacgccttt attttgacaa gagaatccgg ttatcctcag  1080
gtgttctatg gggatatgta cgggacaaaa gggacatcgc caaaggaaat tccctcactg  1140
aaagataata tagagccgat tttaaaagcg cgtaaggagt acgcatacgg gccccagcac  1200
gattatattg accacccgga tgtgatcgga tggacgaggg aaggtgacag ctccgccgcc  1260
aaatcaggtt tggccgcttt aatcacggac ggacccggcg gatcaaagcg gatgtatgcc  1320
ggcctgaaaa atgccggcga gacatggtat gacataacgg gcaaccgttc agatactgta  1380
aaaatcggat ctgacggctg ggagagtttt catgtaaacg atgggtccgt ctccatttat  1440
gttcagaaat aa                                                     1452

SEQ ID NO: 14          moltype = AA  length = 483
FEATURE                Location/Qualifiers
source                 1..483
                       mol_type = protein
                       organism = Bacillus amyloliquefaciens
SEQUENCE: 14
VNGTLMQYFE WYTPNDGQHW KRLQNDAEHL SDIGITAVWI PPAYKGLSQS DNGYGPYDLY  60
DLGEFQQKGT VRTKYGTKSE LQDAIGSLHS RNVQVYGDVV LNHKAGADAT EDVTAVEVNP  120
ANRNQETSEE YQIKAWTDFR FPGRGNTYSD FKWHWYHFDG ADWDESRKIS RIFKFRGEGK  180
AWDWEVSSEN GNYDYLMYAD VDYDHPDVVA ETKKWGIWYA NELSLDGFRI DAAKHIKFSF  240
LRDWVQAVRQ ATGKEMFTVA EYWQNNAGKL ENYLNKTSFN QSVFDVPLHF NLQAASSQGG  300
GYDMRRLLDG TVVSRHPEKA VTFVENHDTQ PGQSLESTVQ TWFKPLAYAF ILTRESGYPQ  360
VFYGDMYGTK GTSPKEIPSL KDNIEPILKA RKEYAYGPQH DYIDHPDVIG WTREGDSSAA  420
KSGLAALITD GPGGSKRMYA GLKNAGETWY DITGNRSDTV KIGSDGWGEF HVNDGSVSIY  480
VQK                                                               483

SEQ ID NO: 15          moltype = DNA  length = 1548
FEATURE                Location/Qualifiers
source                 1..1548
                       mol_type = genomic DNA
                       organism = Bacillus stearothermophilus
CDS                    1..1548
SEQUENCE: 15
gccgcaccgt ttaacggcac catgatgcag tattttgaat ggtacttgcc ggatgatggc  60
acgttatgga ccaaagtggc caatgaagcc aacaacttat ccagccttgg catcaccgct  120
ctttggctgc cgcccgctta caaaggaaca agccgcagcg acgtagggta cggagtatac  180
gacttgtatg acctcggcga attcaatcaa aaagggaccg tccgcacaaa atacggaaca  240
aaagctcaat atcttcaagc cattcaagcc gcccacgccg ctggaatgca agtgtacgcc  300
gatgtcgtgt tcgaccataa aggcggcgct gacggcacgg aatgggtgga cgccgtcgaa  360
gtcaatccgt ccgaccgcaa ccaagaaatc tcgggcacct atcaaatcca agcatggacg  420
aaatttgatt ttcccgggcg gggcaacacc tactccagct ttaagtggcg ctggtaccat  480
tttgacggcg ttgattggga cgaaagccga aaattgagcc gcatttacaa attccgcggc  540
atcggcaaag cgtgggattg ggaagtagac acggaaaacg gaaactatga ctacttaatg  600
tatgccgacc ttgatatgga tcatcccgaa gtcgtgaccg agctgaaaaa ctgggggaaa  660
tggtatgtca acacaacgaa cattgatggg ttccggcttg atgccgtcaa gcatattaag  720
ttcagttttt ttcctgattg gttgtcgtat gtgcgttctc agactggcaa gccgctattt  780
accgtcgggg aatattggag ctatgacatc aacaagttgc acaattacat tacgaaaaca  840
gacggaacga tgtctttgtt tgatgccccg ttacacaaca aattttatac cgcttccaaa  900
tcagggggcg catttgatat gcgcacgtta atgaccaata ctctcatgaa agatcaaccg  960
acattggccg tcaccttcgt tgataatcat gacaccgaac ccggccaagc gctgcagtca  1020
tgggtcgacc catggttcaa accgttggct tacgccttta ttctaactcg gcaggaagga  1080
tacccgtgcg tcttttatgg tgactattat ggcattccac aatataacat tccttcgctg  1140
aaaagcaaaa tcgatccgct cctcatcgcg cgcagggatt atgcttacgg aacgcaacat  1200
gattatcttg atcactccga catcatcggg tggacaaggg aagggggcac tgaaaaacca  1260
ggatccggac tggccgcact gatcaccgat gggccgggag gaagcaaatg gatgtacgtt  1320
ggcaaacaac acgctggaaa agtgttctat gaccttaccg gcaaccggag tgacaccgtc  1380
accatcaaca gtgatggatg gggggaattc aaagtcaatg gcggttcggt ttcggtttgg  1440
gttcctagaa aaacgaccgt ttctaccatc gctcggccga tcacaacccg accgtggact  1500
ggtgaattcg tccgttggac cgaaccacgg ttggtggcat ggccttga               1548

SEQ ID NO: 16          moltype = AA  length = 515
FEATURE                Location/Qualifiers
source                 1..515
                       mol_type = protein
                       organism = Bacillus stearothermophilus
SEQUENCE: 16
AAPFNGTMMQ YFEWYLPDDG TLWTKVANEA NNLSSLGITA LWLPPAYKGT SRSDVGYGVY  60
DLYDLGEFNQ KGTVRTKYGT KAQYLQAIQA AHAAGMQVYA DVVFDHKGGA DGTEWVDAVE  120
VNPSDRNQEI SGTYQIQAWT KFDFPGRGNT YSSFKWRWYH FDGVDWDESR KLSRIYKFRG  180
IGKAWDWEVD TENGNYDYLM YADLDMDHPE VVTELKNWGK WYVNTTNIDG FRLDAVKHIK  240
FSFFPDWLSY VRSQTGKPLF TVGEYWSYDI NKLHNYITKT DGTMSLFDAP LHNKFYTASK  300
SGGAFDMRTL MTNTLMKDQP TLAVTFVDNH DTEPGQALQS WVDPWFKPLA YAFILTRQEG  360
YPCVFYGDYY GIPQYNIPSL KSKIDPLLIA RRDYAYGTQH DYLDHSDIIG WTREGGTEKP  420
GSGLAALITD GPGGSKWMYV GKQHAGKVFY DLTGNRSDTV TINSDGWGEF KVNGGSVSVW  480
VPRKTTVSTI ARPITTRPWT GEFVRWTEPR LVAWP                             515
```

-continued

```
SEQ ID NO: 17          moltype = DNA  length = 1455
FEATURE                Location/Qualifiers
source                 1..1455
                       mol_type = genomic DNA
                       organism = Bacillus sp.
CDS                    1..1455
SEQUENCE: 17
catcataatg ggacgaatgg gaccatgatg cagtattttg aatggcattt gccaaatgac  60
gggaaccact ggaacaggtt acgagatgac gcagctaact taaagagtaa agggattacc  120
gctgtttgga ttcctcctgc atggaagggg acttcgcaaa atgatgttgg gtatggtgcc  180
tatgatttgt acgatcttgg tgagtttaac caaaagggaa ccgtccgtac aaaatatggc  240
acaaggagtc agttgcaagg tgccgtgaca tctttgaaaa ataacgggat tcaagtttat  300
ggggatgtcg tgatgaatca taaaggtgga gcagacggga cagagatggt aaatgcggtg  360
gaagtgaacc gaagcaaccg aaaccaagaa atatcaggtg aatacaccat tgaagcatgg  420
acgaaatttg atttccctgg aagaggaaat acccattcca actttaaatg gcgctggtat  480
cattttgatg ggacagattg ggatcagtca cgtcagcttc agaacaaaat atataaattc  540
agaggtaccg gaaaggcatg ggactgggaa gtagatatag agaacggcaa ctatgattac  600
cttatgtatg cagacattga tatggatcat ccagaagtaa tcaatgaact tagaaattgg  660
ggagtttggt atacaaatac acttaatcta gatggattta gaatcgatgc tgtgaaacat  720
attaaataca gctatacgag agattggcta acacatgtgc gtaacaccac aggtaaacca  780
atgtttgcag ttgcagaatt ttggaaaaat gaccttgctg caatcgaaaa ctatttaaat  840
aaaacaagtt ggaatcactc cgtgttcgat gttcctcttc attataattt gtacaatgca  900
tctaatagtg gtggctattt tgatatgaga aatattttaa atggttctgt cgtacaaaaa  960
caccctatac atgcagtcac atttgttgat aaccatgact ctcagccagg agaagcattg  1020
gaatcctttg ttcaatcgtg gttcaaacca ctggcatatg cattgattct gacaagggag  1080
caaggttacc cttccgtatt ttacggtgat tactacggta taccaactca tggtgttcct  1140
tcgatgaaat ctaaaattga tccacttctg caggcacgtc aaacgtatgc ctacggaacc  1200
caacatgatt attttgatca tcatgatatt atcggctgga cgagagaagg ggacagctcc  1260
cacccaaatt caggacttgc aactattatg tccgatgggc caggggggtaa taaatggatg  1320
tatgtcggga aacataaagc tggccaagta tggagagata tcaccggaaa taggtctggt  1380
accgtcacca ttaatgcaga tggttggggg aatttcactg taaacggagg ggcagtttcg  1440
gtttgggtga agcaa                                                   1455

SEQ ID NO: 18          moltype = AA  length = 485
FEATURE                Location/Qualifiers
source                 1..485
                       mol_type = protein
                       organism = Bacillus sp.
SEQUENCE: 18
HHNGTNGTMM QYFEWHLPND GNHWNRLRDD AANLKSKGIT AVWIPPAWKG TSQNDVGYGA  60
YDLYDLGEFN QKGTVRTKYG TRSQLQGAVT SLKNNGIQVY GDVVMNHKGG ADGTEMVNAV  120
EVNRSNRNQE ISGEYTIEAW TKFDFPGRGN THSNFKWRWY HFDGTDWDQS RQLQNKIYKF  180
RGTGKAWDWE VDIENGNYDY LMYADIDMDH PEVINELRNW GVWYTNTLNL DGFRIDAVKH  240
IKYSYTRDWL THVRNTTGKP MFAVAEFWKN DLAAIENYLN KTSWNHSVFD VPLHYNLYNA  300
SNSGGYFDMR NILNGSVVQK HPIHAVTFVD NHDSQPGEAL ESFVQSWFKP LAYALILTRE  360
QGYPSVFYGD YYGIPTHGVP SMKSKIDPLL QARQTYAYGT QHDYFDHHDI IGWTREGDSS  420
HPNSGLATIM SDGPGGNKWM YVGKHKAGQV WRDITGNRSG TVTINADGWG NFTVNGGAVS  480
VWVKQ                                                              485

SEQ ID NO: 19          moltype = DNA  length = 1452
FEATURE                Location/Qualifiers
source                 1..1452
                       mol_type = genomic DNA
                       organism = Bacillus licheniformis
CDS                    1..1452
SEQUENCE: 19
gcaaatctta atgggacgct gatgcagtat tttgaatggt acatgcccaa tgacggccaa  60
cattggaggc gtttgcaaaa cgactcggca tatttggctg aacacggtat tactgccgtc  120
tggattcccc cggcatataa gggaacgagc caagcggatg tgggctacgg tgcttacgac  180
ctttatgatt taggggagtt tcatcaaaaa gggacggttc ggacaaagta cggcacaaaa  240
ggagagctgc aatctgcgat caaaagtctt cattcccgcg acattaacgt ttacggggat  300
gtggtcatca accacaaagg cggcgctgat gcgaccgaag atgtaaccgc ggttgaagtc  360
gatcccgctg accgcaaccg cgtaatttca ggagaacacc taattaaagc ctggacacat  420
tttcattttc cggggcgcgg cagcacatac agcgatttta aatggcattg gtaccatttt  480
gacggaaccg attgggacga gtcccgaaag ctgaaccgca tctataagtt tcaaggaaag  540
gcttgggatt gggaagtttc caatgaaaac ggcaactatg attatttgat gtatgccgac  600
atcgattatg accatcctga tgtcgcagca gaaattaaga gatggggcac ttggtatgcc  660
aatgaactgc aattggacgg tttccgtctt gatgctgtca aacacattaa atttcttttt  720
ttgcgggatt gggttaatca tgtcagggaa aaaacgggga aggaaatgtt tacggtagct  780
gaatattggc agaatgactt gggcgcgctg gaaaactatt tgaacaaaac aaattttaat  840
cattcagtgt ttgacgtgcc gcttcattat cagttccatg ctgcatcgac acagggaggc  900
ggctatgata tgaggaaatt gctgaacggt acggtcgttt ccaagcatcc gttgaaatcg  960
gttacatttg tcgataacca tgatacacag ccggggcaat cgcttgagtc gactgtccaa  1020
acatggttta agccgcttgc ttacgctttt attctcacaa gggaatctgg ataccctcag  1080
gttttctacg gggatatgta cgggacgaaa ggagactccc agcgcgaaat tcctgccttg  1140
aaacacaaaa ttgaaccgat cttaaaagcg agaaaacagt atgcgtacgg agcacagcat  1200
gattatttcg accaccatga cattgtcggc tggacaaggg aaggcgacag ctcggttgca  1260
aattcaggtt tggcggcatt aataacagac ggacccggtg gggcaaagcg aatgtatgtc  1320
```

-continued

```
ggccggcaaa acgccggtga gacatggcat gacattaccg gaaaccgttc ggagccggtt  1380
gtcatcaatt cggaaggctg gggagagttt cacgtaaacg gcgggtcggt ttcaatttat  1440
gttcaaagat ag                                                      1452

SEQ ID NO: 20          moltype = AA  length = 483
FEATURE                Location/Qualifiers
source                 1..483
                       mol_type = protein
                       organism = Bacillus licheniformis
SEQUENCE: 20
ANLNGTLMQY FEWYMPNDGQ HWRRLQNDSA YLAEHGITAV WIPPAYKGTS QADVGYGAYD  60
LYDLGEFHQK GTVRTKYGTK GELQSAIKSL HSRDINVYGD VVINHKGGAD ATEDVTAVEV  120
DPADRNRVIS GEHLIKAWTH FHFPGRGSTY SDFKWHWYHF DGTDWDESRK LNRIYKFQGK  180
AWDWEVSNEN GNYDYLMYAD IDYDHPDVAA EIKRWGTWYA NELQLDGFRL DAVKHIKFSF  240
LRDWVNHVRE KTGKEMFTVA EYWQNDLGAL ENYLNKTNFN HSVFDVPLHY QFHAASTQGG  300
GYDMRKLLNG TVVSKHPLKS VTFVDNHDTQ PGQSLESTVQ TWFKPLAYAF ILTRESGYPQ  360
VFYGDMYGTK GDSQREIPAL KHKIEPILKA RKQYAYGAQH DYFDHHDIVG WTREGDSSVA  420
NSGLAALITD GPGGAKRMYV GRQNAGETWH DITGNRSEPV VINSEGWGEF HVNGGSVSIY  480
VQR                                                                483

SEQ ID NO: 21          moltype = DNA  length = 1455
FEATURE                Location/Qualifiers
source                 1..1455
                       mol_type = genomic DNA
                       organism = Bacillus sp.
CDS                    1..1455
SEQUENCE: 21
caccataatg gcacaaatgg aacaatgatg caatattttg aatggtattt gccaaatgac  60
ggtaatcatt ggaatagatt aagatcagat gcaagtaatc ttaaagataa agggattaca  120
gcggtttgga ttccacctgc ttggaaaggg gcttctcaaa atgatgtagg gtatggagcc  180
tatgatctgt atgatttagg agaattcaat caaaaaggaa ccgtacgtac aaagtacgga  240
acccgtaatc aattacaagc tgcagtaacc gccttaaaaa gtaatggtat tcaagtatac  300
ggagatgtcg taatgaatca taagggtgga gcggatgcca ctgagtgggt tcgagcggtt  360
gaagtgaacc caagtaatcg taatcaagaa gtctctggtg attatacgat tgaggcttgg  420
actaagtttg atttcctgg tcgaggtaat acccactcta actttaaatg gagatggtat  480
catttcgatg gtgtagattg ggatcagtca cgtcaattgc agaatcgaat ctataaattc  540
agaggagatg gaaaaggttg ggactgggaa gttgatacag agaacggaaa ctatgactat  600
ctaatgtacg cggatattga tatggatcac cctgaagtag tgaatgaact cagaaactgg  660
ggtgtatggt ataccaatac actgggggcta gacgggttca gaatagatgc ggtaaaacat  720
ataaaatata gctttactcg tgattggctt actcacgtta gaaatacgac aggtaaaaat  780
atgtttgcag ttgcagagtt ctggaagaat gacataggtg caattgaaaa ttacttaagt  840
aaaacaaatt ggaatcattc agtttttgat gtgcccctgc attataacct ttataatgca  900
tcgagaagtg gtggcaatta tgatatgagg caaatattta atggaacagt tgttcagaga  960
catcctacac atgctgtaac atttgttgat aaccatgatt cacagccgga agaagcccta  1020
gagtcatttg ttgaagagtg gttcaaaccg ttagcgtatg ctctcacact aacacgtgat  1080
caaggatatc cttccgtttt ttatggagat tattatggga ttccgacgca tggtgtacca  1140
gcaatgaaat ctaagattga tccgatttta gaagcacgtc aaaagtatgc gtacggaaaa  1200
caaaatgatt atttggatca ccataatatg attggctgga cgcgtgaagg taatacagca  1260
catcccaact caggactagc aactattatg tcggatggcc caggaggaaa taaatggatg  1320
tatgttgggc gtaataaggc tggacaagtt tggagagata ttacaggaaa tcgctcaggt  1380
acggtgacga ttaacgcaga tgggtggggt aatttttctg taaatggtgg gtctgtatct  1440
atatgggtaa ataat                                                   1455

SEQ ID NO: 22          moltype = AA  length = 485
FEATURE                Location/Qualifiers
source                 1..485
                       mol_type = protein
                       organism = Bacillus sp.
SEQUENCE: 22
HHNGTNGTMM QYFEWYLPND GNHWNRLRSD ASNLKDKGIT AVWIPPAWKG ASQNDVGYGA  60
YDLYDLGEFN QKGTVRTKYG TRNQLQAAVT ALKSNGIQVY GDVVMNHKGG ADATEWVRAV  120
EVNPSNRNQE VSGDYTIEAW TKFDFPGRGN THSNFKWRWY HFDGVDWDQS RQLQNRIYKF  180
RGDGKGWDWE VDTENGNYDY LMYADIDMDH PEVVNELRNW GVWYTNTLGL DGFRIDAVKH  240
IKYSFTRDWL THVRNTTGKN MFAVAEFWKN DIGAIENYLS KTNWNHSVFD VPLHYNLYNA  300
SRSGGNYDMR QIFNGTVVQR HPTHAVTFVD NHDSQPEEAL ESFVEEWFKP LAYALTLTRD  360
QGYPSVFYGD YYGIPTHGVP AMKSKIDPIL EARQKYAYGK QNDYLDHHNM IGWTREGNTA  420
HPNSGLATIM SDGPGGNKWM YVGRNKAGQV WRDITGNRSG TVTINADGWG NFSVNGGSVS  480
IWVNN                                                              485

SEQ ID NO: 23          moltype = DNA  length = 1452
FEATURE                Location/Qualifiers
source                 1..1452
                       mol_type = genomic DNA
                       organism = Bacillus sp.
CDS                    1..1452
SEQUENCE: 23
ggaagtgtgc cggtaaatgg cacaatgatg caatatttcg aatggtacct tccagacgat  60
ggaacactat ggacgaaagt agcaaataac gctcaatctt tagcgaatct tggcattact  120
gccctttggc ttccccctgc ctataaagga acaagcagca gtgacgttgg atatggcgtt  180
```

-continued

```
tatgatttat atgaccttgg agagtttaat caaaaaggaa ctgtccgaac aaaatacggg  240
acaaaaacac aatatatcca agcaatccaa gcggcgcata cagcagggat gcaagtatat  300
gcagatgtcg tctttaacca taaagccggt gcagatggaa cagaactagt cgatgcagta  360
gaagtaaatc cttctgaccg caatcaagaa atatcaggaa catatcaaat ccaagcgtgg  420
acaaaatttg attttcctgg tcgtggaaac acctattcta gttttaaatg gcgttggtat  480
catttcgatg gaacggactg ggatgagagt agaaaactaa atcgtattta caagttccgc  540
ggcacgggaa aagcatggga ttgggaagta gatacagaaa acgggaatta tgactatctc  600
atgtatgcag atttagatat ggatcatcca gaggttgtat ccgaactaaa aaattgggga  660
aagtggtatg taaccacaac caatatcgac ggattccgtc tggatgcagt gaagcatatt  720
aaatatagct ttttcccgga ctggctatcg tacgtacgaa cccaaacaca aaagcctctt  780
tttgccgttg gggaattttg gagctatgac attagcaagt tgcacaacta tattacaaag  840
acgaacggct ctatgtccct attcgatgcc ccgctgcata acaattttta tatagcatcg  900
aaatcaggcg gttattttga tatgcgcaca ttactcaaca acacattgat gaaagatcag  960
cctacattag cagtcacatt agtggataat cacgatactg agccagggca atctctgcag  1020
tcatgggtcg agccatggtt taaaccgtta gcttacgcat ttatcttgac ccgccaagaa  1080
ggttatcctt gcgtctttta tggagattac tatggtattc caaaatacaa cattcctgcg  1140
ctgaaaagca aacttgatcc gctgttaatt gccagaagag attatgccta tggaacacag  1200
cacgactata ttgacagtgc ggatattatc ggttggacgc gggaaggagt ggctgaaaaa  1260
gcaaattcag gactggctgc actcattacc gacgggcctg gcggaagcaa atggatgtat  1320
gttggaaaac aacacgctgg caaaacgttt tatgatttaa ccggcaatcg aagtgataca  1380
gtgacaatca atgctgatgg atggggagaa tttaaagtca atggagggtc tgtatccata  1440
tgggttccaa aa                                                      1452

SEQ ID NO: 24          moltype = AA  length = 484
FEATURE                Location/Qualifiers
source                 1..484
                       mol_type = protein
                       organism = Bacillus sp.
SEQUENCE: 24
GSVPVNGTMM QYFEWYLPDD GTLWTKVANN AQSLANLGIT ALWLPPAYKG TSSSDVGYGV  60
YDLYDLGEFN QKGTVRTKYG TKTQYIQAIQ AAHTAGMQVY ADVVFNHKAG ADGTELVDAV  120
EVNPSDRNQE ISGTYQIQAW TKFDFPGRGN TYSSFKWRWY HFDGTDWDES RKLNRIYKFR  180
GTGKAWDWEV DTENGNYDYL MYADLDMDHP EVVSELKNWG KWYVTTTNID GFRLDAVKHI  240
KYSFFPDWLS YVRTQTQKPL FAVGEFWSYD ISKLHNYITK TNGSMSLFDA PLHNNFYIAS  300
KSGGYFDMRT LLNNTLMKDQ PTLAVTLVDN HDTEPGQSLQ SWVEPWFKPL AYAFILTRQE  360
GYPCVFYGDY YGIPKYNIPA LKSKLDPLLI ARRDYAYGTQ HDYIDSADII GWTREGVAEK  420
ANSGLAALIT DGPGGSKWMY VGKQHAGKTF YDLTGNRSDT VTINADGWGE FKVNGGSVSI  480
WVPK                                                               484

SEQ ID NO: 25          moltype = DNA  length = 1455
FEATURE                Location/Qualifiers
source                 1..1455
                       mol_type = genomic DNA
                       organism = Bacillus sp.
CDS                    1..1455
SEQUENCE: 25
gctaatactg cacctattaa cgaaacaatg atgcaatatt ttgaatggga tttaccgaac  60
gatggaaccc tttggacaaa ggtgaaaaat gaagccgcaa atctttcttc gctcggtatt  120
acagcgttat ggcttcctcc agcgtataaa ggaacaagtc aaagcgatgt cggatacggc  180
gtgtacgatt tatatgacct tggggaattt aatcaaaaag gaacgattcg aacaaaatac  240
ggaacaaaaa cacaatatat tcaagccatc caagctgcca aagccgcagg gatgcaagta  300
tatgcagatg ttgtctttaa tcataaggcg ggagctgacg gcacagaatt tgtcgatgcg  360
gttgaggtag acccttctaa tcgaaatcaa gaaacatctg gaacatatca aattcaagca  420
tggacaaaat ttgattttcc cggtcggggg aacacatact cgagttttaa atggcgttgg  480
tatcattttg acggtaccga ttgggatgaa agccgaaaat taaatcggat ttacaaattc  540
cgcagtacag gaaaagcatg ggactgggaa gtcgatacag aaaacggaaa ctatgattat  600
ttaatgttcg ctgatttaga tatggatcac cctgaggttg tgacagaatt aaaaaactgg  660
ggaacgtggt acgtcaatac tacaaatatc gatggattcc gcttagatgc cgtaaaacat  720
attaaataca gcttttcccc tgactggcta acatatgtac gtaatcaaac aggaaaaaat  780
ttatttgccg ttggggaatt ttggagctat gacgtcaata agctgcataa ttacattaca  840
aaaacaaatg gatcgatgtc attatttgat gcacctttgc ataacaactt ttataccgct  900
tccaaatcga gtggatattt tgacatgcgt tatttattga ataatacatt aatgaaagat  960
caaccttcac tcgctgtgac acttgtcgat aaccacgaca cgcaaccagg gcaatcttta  1020
cagtcatggg tcgaaccttg gtttaaacca cttgcttacg cctttatttt aacgagacaa  1080
gagggatatc cttgcgtatt ttacggtgac tattatggaa tcccgaaata caatattcca  1140
ggattaaaaa gcaaaatcga cccgctttta attgctcgtc gggactatgc ctatggaaca  1200
caacgtgatt acattgacca tcaagacatt attggatgga cacgcgaagg cattgataca  1260
aaaccaaact ctggactggc ggctttaatt accgacggcc ctggcggaag caaatggatg  1320
tatgtcggta aaaaacatgc tggaaaagta ttttatgatt taaccggaaa ccgaagtgac  1380
acagtaacga ttaatgcgga tggttgggga gaatttaaag taaacggagg ctccgtttcg  1440
atttgggtgg ctaaa                                                   1455

SEQ ID NO: 26          moltype = AA  length = 485
FEATURE                Location/Qualifiers
source                 1..485
                       mol_type = protein
                       organism = Bacillus sp.
SEQUENCE: 26
ANTAPINETM MQYFEWDLPN DGTLWTKVKN EAANLSSLGI TALWLPPAYK GTSQSDVGYG  60
```

-continued

```
VYDLYDLGEF NQKGTIRTKY GTKTQYIQAI QAAKAAGMQV YADVVFNHKA GADGTEFVDA  120
VEVDPSNRNQ ETSGTYQIQA WTKFDFPGRG NTYSSFKWRW YHFDGTDWDE SRKLNRIYKF  180
RSTGKAWDWE VDTENGNYDY LMFADLDMDH PEVVTELKNW GTWYVNTTNI DGFRLDAVKH  240
IKYSFFPDWL TYVRNQTGKN LFAVGEFWSY DVNKLHNYIT KTNGSMSLFD APLHNNFYTA  300
SKSSGYFDMR YLLNNTLMKD QPSLAVTLVD NHDTQPGQSL QSWVEPWFKP LAYAFILTRQ  360
EGYPCVFYGD YYGIPKYNIP GLKSKIDPLL IARRDYAYGT QRDYIDHQDI IGWTREGIDT  420
KPNSGLAALI TDGPGGSKWM YVGKKHAGKV FYDLTGNRSD TVTINADGWG EFKVNGGSVS  480
IWVAK                                                              485
```

The invention claimed is:

1. A composition comprising a variant of a parent alpha-amylase, wherein the variant has alpha-amylase activity and comprises a substitution of a L or a Y at position 206 using the numbering according to SEQ ID NO: 6, wherein the variant has at least 90% sequence identity with the polypeptide of SEQ ID NO: 6, 8, 10, 12, 18, or 20, and further comprising at least one chelating agent, and wherein said chelating agent at a concentration below 10 mM reduces the concentration of free calcium ions from 2.0 mM to 0.10 mM when measured at 21° C. and pH 8.0.

2. An alpha-amylase variant comprising 206Y or 206L, wherein position 206 corresponds to the numbering according to SEQ ID NO: 6, and wherein the variant has alpha-amylase activity and has at least 90% sequence identity with the polypeptide of SEQ ID NO: 6.

3. The alpha-amylase variant of claim 2, further comprising a substitution at position 116.

4. The alpha-amylase variant of claim 2, further comprising a substitution at position 133.

5. The alpha-amylase variant of claim 2, further comprising a substitution at position 142.

6. The alpha-amylase variant of claim 2, further comprising a substitution at position 152.

7. The alpha-amylase variant of claim 2, further comprising a substitution at position 169.

8. The alpha-amylase variant of claim 2, further comprising a substitution at position 235.

9. The alpha-amylase variant of claim 2, further comprising a substitution at position 303.

10. The alpha-amylase variant of claim 2, further comprising a substitution at position 320.

11. The alpha-amylase variant of claim 2, further comprising a substitution at position 458.

12. The alpha-amylase variant of claim 2, further comprising a substitution at one or more positions selected from the group consisting of 197, 198, 200, 203, 210, 212, 213 and 243.

13. The alpha-amylase variant of claim 2, wherein the variant has at least 95% sequence identity with the polypeptide of SEQ ID NO: 6.

14. The alpha-amylase variant of claim 2, wherein the variant has at least 98% sequence identity with the polypeptide of SEQ ID NO: 6.

15. A composition comprising a variant of a parent alpha-amylase, wherein the variant has alpha-amylase activity and comprises a substitution of a L or a Y at position 206 using the numbering according to SEQ ID NO: 6, wherein the variant has at least 90% sequence identity with the polypeptide of SEQ ID NO: 6, and further comprising at least one chelating agent, wherein said chelating agent at a concentration below 10 mM reduces the concentration of free calcium ions from 2.0 mM to 0.10 mM when measured at 21° C. and pH 8.0.

16. An alpha-amylase variant comprising 206Y or 206L, wherein position 206 corresponds to the numbering according to SEQ ID NO: 6, and wherein the variant has alpha-amylase activity and has at least 95% sequence identity with the polypeptide of SEQ ID NO: 6.

* * * * *